US010582847B2

(12) United States Patent
Raymond et al.

(10) Patent No.: US 10,582,847 B2
(45) Date of Patent: *Mar. 10, 2020

(54) METHOD AND SYSTEM FOR EYE MEASUREMENTS AND CATARACT SURGERY PLANNING USING VECTOR FUNCTION DERIVED FROM PRIOR SURGERIES

(71) Applicant: AMO WaveFront Sciences, LLC, Albuquerque, NM (US)

(72) Inventors: Thomas D. Raymond, Edgewood, NM (US); Daniel R. Neal, Tijeras, NM (US); Richard J. Copland, Albuquerque, NM (US); Wei Xiong, Albuquerque, NM (US); Paul Pulaski, Albuquerque, NM (US); Stephen W. Farrer, Albuquerque, NM (US); Carmen Canovas Vidal, Groningen (NL); Daniel R. Hamrick, Cedar Crest, NM (US)

(73) Assignee: AMO WaveFront Sciences, LLC, Albuquerque, NM (US)

( * ) Notice: Subject to any disclaimer, the term of this patent is extended or adjusted under 35 U.S.C. 154(b) by 168 days.

This patent is subject to a terminal disclaimer.

(21) Appl. No.: 14/949,783

(22) Filed: Nov. 23, 2015

(65) Prior Publication Data
US 2016/0150952 A1  Jun. 2, 2016

Related U.S. Application Data

(63) Continuation-in-part of application No. 13/341,385, filed on Dec. 30, 2011.
(Continued)

(51) Int. Cl.
*A61F 9/008* (2006.01)
*A61B 3/00* (2006.01)
(Continued)

(52) U.S. Cl.
CPC ............ *A61B 3/0025* (2013.01); *A61B 3/103* (2013.01); *A61B 3/1015* (2013.01); *A61B 34/10* (2016.02);
(Continued)

(58) Field of Classification Search
CPC .... A61F 2/1662; A61F 9/00736; A61F 9/008; A61F 9/00825; A61F 2009/00857;
(Continued)

(56) References Cited

U.S. PATENT DOCUMENTS 4,575,373 A * 3/1986 Johnson ................ A61F 2/1613
623/6.22
4,669,466 A 6/1987 L'Esperance
(Continued)

FOREIGN PATENT DOCUMENTS

EP 1327948 A2 7/2003
EP 2232198 B1 6/2015
(Continued)

OTHER PUBLICATIONS

Koh S., et al., "Simultaneous Measurement of Tear Film Dynamics Using Wave front Sensor and Optical Coherence Tomography," Investigative Ophthalmology & Visual Science, 2010, vol. 51 (7), pp. 3441-3448.
(Continued)

*Primary Examiner* — Eric D. Bertram
(74) *Attorney, Agent, or Firm* — Johnson & Johnson Surgical Vision, Inc.

(57) ABSTRACT

Improved devices, systems, and methods for planning cataract surgery on an eye of a patient incorporate results of prior corrective surgeries into a planned cataract surgery of a particular patient by driving an effective surgery vector function based on data from the prior corrective surgeries. The exemplary effective surgery vector employs an influ-
(Continued)

ence matrix which may allow improved refractive corrections to be generated so as to increase the overall efficacy of a cataract surgery by specifying one or more parameters of an intraocular lens (IOL) to be implanted during the cataract surgery.

6 Claims, 29 Drawing Sheets

Related U.S. Application Data

(60) Provisional application No. 61/428,644, filed on Dec. 30, 2010.

(51) Int. Cl.
*A61B 34/10* (2016.01)
*A61B 3/10* (2006.01)
*A61B 3/103* (2006.01)

(52) U.S. Cl.
CPC .......... *A61F 9/008* (2013.01); *A61F 9/00804* (2013.01); *A61F 9/00827* (2013.01); *A61F 9/00829* (2013.01); *A61B 2034/102* (2016.02); *A61F 2009/0088* (2013.01); *A61F 2009/00857* (2013.01); *A61F 2009/00859* (2013.01); *A61F 2009/00872* (2013.01); *A61F 2009/00882* (2013.01); *A61F 2009/00887* (2013.01)

(58) Field of Classification Search
CPC .... A61F 2009/0087; A61F 2009/00872; A61F 2009/0088; A61F 2009/00853; A61F 2009/00859
USPC .................................. 606/5, 10–13; 623/6.11
See application file for complete search history.

(56) References Cited

U.S. PATENT DOCUMENTS

| | | | |
|---|---|---|---|
| 4,721,379 A * | 1/1988 | L'Esperance | A61F 9/00804 606/5 |
| 5,777,719 A | 7/1998 | Williams et al. | |
| 6,095,651 A | 8/2000 | Williams et al. | |
| 6,428,533 B1 | 8/2002 | Bille | |
| 6,550,917 B1 | 4/2003 | Neal et al. | |
| 6,572,230 B2 | 6/2003 | Levine | |
| 6,698,889 B2 | 3/2004 | Pettit et al. | |
| 6,908,196 B2 | 6/2005 | Herekar et al. | |
| 7,044,944 B2 * | 5/2006 | Campin | A61F 9/00806 606/10 |
| 7,455,407 B2 | 11/2008 | Neal et al. | |
| 7,553,022 B2 | 6/2009 | Neal et al. | |
| 7,926,490 B2 * | 4/2011 | Dai | A61F 9/008 606/10 |
| 7,980,699 B2 | 7/2011 | Neal et al. | |
| 7,988,292 B2 | 8/2011 | Neal et al. | |
| 8,126,246 B2 | 2/2012 | Farrer et al. | |
| 8,260,024 B2 | 9/2012 | Farrer et al. | |
| 8,430,508 B2 | 4/2013 | Weeber | |
| 8,444,267 B2 | 5/2013 | Weeber et al. | |
| 8,480,228 B2 | 7/2013 | Weeber | |
| 8,623,081 B2 | 1/2014 | Canovas Vidal et al. | |
| 8,696,119 B2 | 4/2014 | Van Der Mooren et al. | |
| 8,696,120 B2 | 4/2014 | Van Der Mooren et al. | |
| 8,746,882 B2 | 6/2014 | Canovas Vidal et al. | |
| 2003/0053030 A1 | 3/2003 | Levine | |
| 2005/0096640 A1 | 5/2005 | Dai et al. | |
| 2005/0225721 A1 * | 10/2005 | Harris | G02C 7/028 351/200 |
| 2006/0023569 A1 | 2/2006 | Agullo et al. | |
| 2006/0173644 A1 | 8/2006 | Dai et al. | |
| 2007/0142826 A1 | 6/2007 | Sacharoff | |
| 2007/0201001 A1 | 8/2007 | Dai | |
| 2009/0033867 A1 | 2/2009 | Dai | |
| 2009/0161090 A1 | 6/2009 | Campbell et al. | |
| 2012/0172854 A1 * | 7/2012 | Raymond | A61F 9/008 606/5 |
| 2013/0226294 A1 | 8/2013 | Van Der Mooren et al. | |
| 2013/0282116 A1 | 10/2013 | Van Der Mooren et al. | |
| 2013/0335701 A1 | 12/2013 | Canovas Vidal et al. | |
| 2014/0253877 A1 | 9/2014 | Li et al. | |
| 2016/0302915 A1 * | 10/2016 | Sayegh | A61F 2/1645 |

FOREIGN PATENT DOCUMENTS

| | | |
|---|---|---|
| JP | 2014530662 A | 11/2014 |
| WO | 0158339 A2 | 8/2001 |
| WO | 0207660 A2 | 1/2002 |
| WO | 03082162 A2 | 10/2003 |
| WO | 2008112292 A1 | 9/2008 |
| WO | 2008151111 A1 | 12/2008 |
| WO | 2013028992 A1 | 2/2013 |
| WO | 2013053938 A1 | 4/2013 |
| WO | 2014172621 A2 | 10/2014 |

OTHER PUBLICATIONS

Kottig F., et al., "An Advanced Algorithm for Dispersion Encoded Full Range Frequency Domain Optical Coherence Tomography," Optics Express, 2012, vol. 20 (22), pp. 24925-24948.
Liu H., et al., "Measurement of the Time Course of Optical Quality and Visual Deterioration during Tear Break-Up," Investigative Ophthalmology & Visual Science, 2010, vol. 51 (6), pp. 3318-3326.
Partial International Search Report for Application No. PCT/US2015/065713, dated Apr. 14, 2016, 9 pages.
Wojtkowski M., et al., "Full Range Complex Spectral Optical Coherence Tomography Technique in Eye Imaging," Optics Letters, 2002, vol. 27 (16), pp. 1415-1417.
International Search Report and Written Opinion for Application No. PCT/US2011/068169, dated Apr. 18, 2012, 16 pages.
Mejia-Barbosa Y., et al., "Object Surface for Applying a Modified Hartmann Test to Measure Corneal Topography," Applied Optics, 2001, vol. 40 (31), pp. 5778-5786.
Nowakowski M., et al., "Investigation of the Isoplanatic Patch and Wavefront Aberration along the Pupillary Axis Compared to the Line of Sight in the Eye," Biomedical Optics Express, 2012, vol. 3 (2), pp. 240-258.
Yang S.H., et al., "Neural Network Computer Program to Determine Photorefractive Keratectomy Nomograms," Journal of Cataract and Refractive Surgery, 1998, vol. 24 (7), pp. 917-924.
Zou W., et al., "High-accuracy Wavefront Control for Retinal Imaging with Adaptive-Influence-Matrix Adaptive Optics," Optics Express, 2009, vol. 17 (22), pp. 20167-20177.
International Search Report and Written Opinion for Application No. PCT/US2015/062225, dated Aug. 9, 2016, 10 pages.
International Preliminary Report on Patentability for Application No. PCT/US2015/062225, dated Jun. 7, 2018, 7 pages.

* cited by examiner

METHOD AND SYSTEM FOR EYE MEASUREMENTS AND CATARACT SURGERY PLANNING USING VECTOR FUNCTION DERIVED FROM PRIOR SURGERIES

CROSS REFERENCE TO RELATED APPLICATION DATA

The present application is a continuation-in-part of U.S. patent application Ser. No. 13/341,385 filed on 30 Dec. 2011, which claims the benefit under 35 USC § 119(e) of U.S. Provisional Application No. 61/428,644 filed Dec. 30, 2010. The full disclosures of the above-mentioned applications are incorporated herein in their entirety as if fully set forth.

BACKGROUND OF THE INVENTION

The present invention pertains generally to ophthalmic surgery and measurements, particularly for identification and/or correction of optical vision deficiencies. In exemplary embodiments, the present invention provides systems and methods for planning and performing cataract surgery, including selection and/or placement of an intraocular lens (IOL) within an eye.

Laser corneal shaping or corrective refractive surgeries are commonly used to treat myopia, hyperopia, astigmatism, and the like. Laser refractive procedures include LASIK and (Laser Assisted In-Situ Keratomileusis), Photorefractive Keratectomy (PRK), Epithelial Keratomileusis (LASEK or Epi-LASEK), and Laser Thermal Keratoplasty. Alternative refraction altering procedures which do not rely on lasers, and/or which do not alter the corneal shape, have also been described.

During LASIK, a surgeon makes a cut part way through a front surface of a cornea, optionally using an oscillating steel blade or microkeratome. The microkeratome automatically advances the blade through the cornea so as to create a thin flap of clear tissue on the front central portion of the eye. The flap can be folded over to expose stromal tissue for selective ablation with an excimer laser. More recently, femtosecond laser systems have been developed to form laser incision in the corneal tissue so as to cut the corneal flap without using a mechanical blade. Regardless of how the flap is prepare, the excimer laser corrects a visual defect by directing a beam of pulsed laser energy onto the exposed corneal stroma. Each laser pulse from the excimer laser removes a very small and precise amount of corneal tissue so that the total removal of stromal tissue from within the cornea alters and corrects the refractive properties of the overall eye. After removal (and more specifically, after laser ablation) of the desired stromal tissue, the flap can be folded back over the ablated surface. The flap of protective epithelial tissue quickly and naturally reattaches over the resculpted stromal tissue, and the eye retains much of the effective alteration in shape after the cornea heals.

A number of alternative laser refractive procedures have been used and/or are being developed. In one variation, rather than incising the corneal tissue for temporary displacement of an epithelial flap, the epithelium may be ablated (typically using the excimer laser) or abraded in a PRK procedure. As an alternative to resculpting the stroma using an excimer laser, it has also been proposed to form incisions within the cornea or other refractive tissues of the eye with the femtosecond laser. These femtosecond laser procedures include corneal lenticule extractions, as well as making relaxing incisions in the cornea to correct the eye's refractive properties. Still further alternatives have been described, and new procedures are being developed to further enhance the capabilities of refractive corrections using lasers and other refractive tissue altering tools.

Known corneal correction treatment methods have generally been quite successful in correcting standard vision errors, such as myopia, hyperopia, and astigmatism. However, as with all successes, still further improvements have become desirable. Toward that end, wavefront measurement systems are now available to measure the refractive characteristics of a particular patient's eye. These wavefront measurement systems allow accurate measurement of the overall aberrations of the optical system of the eye, providing quite detailed information on the high-order optical aberrations that may limit a patient's visual acuity even after the standard refractive errors have been corrected (for example, by eye glasses, contact lenses, and the like). Still additional measurement tools may provide information which is useful for such customized ablation procedures. For example, corneal topographers are commercially available that can provide quite accurate information regarding the shape of the anterior surface of the cornea, and this surface may have a significant role in the overall optical properties of the eye. Optical coherence tomographers (OCT) may provide information regarding both the anterior and interior surfaces of the eye. By combining these accurate measurement tools with the flexibility of modern scanning excimer lasers, custom refractive corrections should correct not only the standard refractive errors of the eye, but also address the specific high-order aberrations of a particular patient.

Although customized laser and other refractive treatments have provided significant benefits for many patients, the overall improvement in refractive performance of the eyes of patients treated using these new techniques has not yet achieved their full theoretical potential. A number of theories or factors have been proposed to help explain why some customized ablation procedures have not altogether eliminated high-order aberrations of the eye. Even when laser refractive corrections were limited to the standard refractive errors of myopia, hyperopia, and astigmatism, the empirical response of prior treatments led to doctors applying discrete adjustment factors or "nomograms" so as to adjust a calculated prescription before imposing the treatment on an eye of a patient. Significant efforts have gone toward increasing the benefit of both standard and customized refractive corrections by identifying analogous nomogram adjustments for high-order aberration corrections. Unfortunately, work in connection with the present invention indicates the challenges of identifying suitable nomogram adjustments for a customized refractive correction for a particular patient in a particular treatment setting may continue to limit the benefits of customized corneal ablations to significantly less than the ideal potential outcomes. In fact, a significant number of high-order refractive treatments may result in other high-order aberrations of the eye actually increasing (even where the visual acuity of the eye overall benefits from the treatment).

Cataract extraction is another frequently performed surgical procedure. A cataract is formed by opacification of the crystalline lens of the eye. The cataract scatters light passing through the lens and may perceptibly degrade vision. A cataract can vary in degree from slight to complete opacity. Early in the development of an age-related cataract, the power of the lens may increase, causing near-sightedness (myopia). Gradual yellowing and opacification of the lens may reduce the perception of blue colors as those shorter wavelengths are more strongly absorbed and scattered within the cataractous crystalline lens. Cataract formation may often progress slowly resulting in progressive vision loss.

A cataract treatment may involve replacing the opaque crystalline lens with an artificial intraocular lens (IOL). Cataract surgery can be performed using a technique termed phacoemulsification in which an ultrasonic tip with associated irrigation and aspiration ports is used to emulsify or sculpt the relatively hard nucleus of the lens to facilitate removal through an opening made in the anterior lens capsule. The nucleus of the lens is contained within an outer membrane of the lens that is referred to as the lens capsule. Access to the lens nucleus can be provided by performing an anterior capsulotomy in which a small round hole can be formed in the anterior side of the lens capsule using a femtosecond laser beam from a laser cataract surgical system. Access to the lens nucleus can also be provided by performing a manual continuous curvilinear capsulorhexis (CCC) procedure using microkeratomes. A femtosecond laser can also be used to soften and break up the cataractous lens so that less energy from phacoemulsification is required for lens extraction. An alternative to phacoemulsification is manual small incision cataract surgery (MSICS), a procedure where the entire lens is expressed out of the eye through a self-sealing scleral tunnel wound.

Regardless of how the lens nucleus is removed, after this is accomplished, a synthetic intraocular lens (IOL) is then inserted into the remaining lens capsule of the eye to replace the cataractous lens.

Planning a cataract treatment can be a challenging problem. Before performing cataract surgery, the surgeon will need to select appropriate parameters for the IOL (e.g., the refractive power of the IOL) to be implanted (much like an eyeglass prescription) to provide the patient with the desired refractive outcome.

There is significant variation from patient-to-patient (or eye-to-eye) in many important eye biometric parameters, each of which may affect surgical planning, treatment and outcome. Moreover, many patients may have biometric configurations, including for example, corneal lower order and higher order aberrations, extreme axial lengths, and/or previous corneal refractive treatments such as LASIK, which may also affect surgical planning, treatment, and outcome. For example, with respect to eye aberrations, some patients have near-sightedness (myopia), far-sightedness (hyperopia), or astigmatism. Near-sightedness occurs when light focuses in front of the retina, while far-sightedness occurs when light refracts to a focus behind the retina. Astigmatism occurs when the corneal curvature is unequal in two or more directions. Various surgical methods have been developed and used to treat these types of aberrations.

Ideally, for best results and outcome, a cataract surgeon would have access to not only ocular biometry information, but also to information on the eye's anterior corneal surface, posterior corneal surface, anterior lens surface, posterior lens surface, lens tilt, lens thickness, and lens position in order to plan cataract treatment pre-operatively, and/or to assess the post-operative refractive state of a patient's eye with the implanted IOL.

Traditionally, doctors use preoperative measurements including corneal curvature, axial length, and white to white measurements to estimate the required power of the IOL, and apply the measured data to formulas such as Hagis, Hoffer Q, Holladay 1, Holladay 2, and SRK/T to name a few, to select the appropriate power of the IOL to be implanted.

A variety of optical measurement systems have been developed, each of which provides a limited subset of the desired measurements. Hence, a cataract patient may currently be required to undergo a number of measurements performed on different devices—if the measurements are taken at all. There is a significant disadvantage in using multiple measurement devices in cataract planning because the patient's eye may be in a different position, it may have changed between measurements, or the measurements may be made under different conditions, etc. Further, there may be no way to combine or fuse the data sets from different devices to obtain a single, three-dimensional model of the patient's eye.

Studies have shown that refractive results using traditional eye measurement techniques and traditional IOL power calculation formulas leave patients within 0.5D of target (correlates to 20/25 when targeted for distance) or better in 55% of cases and within 1D (correlates to 20/40 when targeted for distance) or better in 85% of cases. Still, this means that in a significant percentage of cases, significantly less-than-optimal results are achieved and there is substantial room for improvement in the techniques employed for cataract surgery planning.

In light of the above, it would be beneficial to provide improved devices, systems, and methods for measuring, diagnosing and/or treating defects of an eye of a cataract patient. Preferably, these improved techniques would still allow physicians to input nomogram adjustments for a particular patient. It would be particularly beneficial if these improvements were able to increase the overall accuracy with which high-order aberrations of an eye could be treated, ideally without significantly increasing the cost or complexity of measurement and/or treatment systems.

In light of the above, it would also be beneficial to provide improved devices, systems, and methods for making eye measurements for diagnosing and/or treating cataracts. It would be particularly beneficial if these improvements were able to increase the overall accuracy with which intraocular lenses for cataract surgery could be specified, selected, and located within an eye, ideally without significantly increasing the cost or complexity of measurement, diagnosis, and/or treatment systems.

BRIEF SUMMARY OF THE INVENTION

The present invention generally provides, among other things, improved devices, systems, and methods for eye measurements and diagnosing, planning treatments of, and/or treating cataracts. The present invention provides a holistic approach for incorporating results of prior refractive corrections and/or surgeries into a planned cataract surgery of a particular patient by deriving an effective treatment vector function based on data from the prior eye treatments and/or refractive surgeries. This effective treatment vector function represents a multivariate feedback approach that can accommodate a large number of factors which contribute to the accuracy of intraocular lens selection and placement in cataract surgery. The exemplary effective treatment vector function employs an influence matrix analytical approach. Although many factors can contribute to induced errors, often with complex couplings between the factors and discrete optical error modes, the use of an influence matrix, (along with a relatively large number of prior eye treatments) may allow improved refractive corrections to be generated from the aberration measurement techniques that are now available. Appropriate use of an influence matrix or other effective treatment vector functions may thereby increase the overall efficacy of cataract surgery, including improved definition of an appropriate intraocular lens (IOL) to be implanted in a patient's eye.

In a first aspect, the invention provides a method for planning cataract surgery on an eye of a patient. The method comprises determining an effective treatment vector function based on a plurality of prior eye treatments. The effective treatment vector function may be determined by, for each prior eye treatment of an associated eye, defining a pre-treatment vector that characterizes measured pre-treatment high-order aberrations of that eye. A post treatment vector characterizing measured post treatment high-order aberrations of the eye is also defined. The effective treatment vector function can then be determined by deriving a correlation between the pre-treatment vectors and the associated post-treatment vectors. An input vector for a particular patient may be defined based on measured pre-treatment, high-order aberrations of the eye of the patient, and the treatment of the eye of the patient may be derived by applying the effective treatment vector function to the input vector.

The input vector may be defined by identifying a target refraction of the eye of the patient to be induced by the refractive treatment. In many cases, the target refraction for the eye of the patient may be emmetropia, such that after treatment of the patient's eye the aberrations are substantially eliminated. Note that his will not always be the case, as treatments may intentionally induce certain desirable aberrations into the eye so as to mitigate presbyopia and the like. Regardless, once the target refraction has been identified, an intended refractive correction vector (IRC) characterizing a difference between the measured pre-treatment aberrations of the eye of the patient and the target can then be determined.

The deriving of the effective treatment vector function may be performed by determining intended refractive correction vectors for each (IRCs) of the associated eyes. A surgically-induced refractive correction (SIRC) can be defined for each eye as the actual change in aberrations, for example, with each SIRC characterizing a difference between the measured pre-treatment aberrations and the post-treatment aberrations of the associated eye.

In the exemplary embodiments, the effective treatment vector function may be derived by determining an influence matrix $\vec{f}$ relating the SIRCs to the IRCs. For example, $\vec{f}$ may relate the SIRCs to the IRCs such that, for the group of associated eyes:

$$\vec{E} = \vec{SIRC} - \vec{f} \cdot \vec{IRC} \qquad \text{Eq. 1}$$

in which $\vec{E}$ is an error vector (which can be driven toward zero so as to derive $f$). The effective treatment vector function may be applied to the input vector by calculating an adjusted intended refractive correction vector (AIRC) from a vector IRC for the eye of the patient which can (in turn) optionally be defined by adjusting the IRC per a physician adjustment and/or a nomogram adjustment. The IRC' (or a vector derived therefrom) can be used as the input vector for deriving the AIRC, and/or for deriving the treatment of the eye of the patient, thereby allowing physician adjustments and nomogram adjustments when desired.

Preferably, the effective treatment vector function is derived using an influence matrix approach. More specifically, the planned treatment of the eye of the patient may be characterized by a planned treatment matrix, and the influence matrix may be derived such that a plurality of the elements of the input vector each alter a plurality of elements of the planned treatment vector. Similarly, a plurality of the planned treatment vector elements may each be altered by a plurality of elements of the input vector. In fact, the influence matrix may be derived such that every element of the input vector (at least those characterizing a refractive shape of the eye of the patient) can and/or does alter every element of the planned treatment matrix (or at least those characterizing a change in the refractive shape of the eye of the patient).

The pre-treatment aberration measurements of the input vector will typically characterize refractive aspects of the eye of the patient, including refractive (such as the standard refractive characteristics of spherical error, astigmatism power, and astigmatism angle) and high-order aberrations (such as Zernike coefficients or the like) of the eye. The input vector may also characterize non-refractive cofactors, including characteristics of the patient (such as the patient's age, gender, race, and the like) and/or the treatment settings (such as the identity of the physician or other system user, the type or specific system used for measurement and/or treatment, the humidity during measurement and/or treatment, the temperature during measurement and/or treatment, the geographical location of measurement and/or treatment, and the like.) The pre-treatment vectors and post-treatment vectors for the prior eye treatments (from which the influence matrix will be derived) may include similar elements.

An exemplary method for deriving the treatment of the eye of the patient may be to multiply the influence matrix of the effective treatment vector function by the input vector so as to define a conditioned input vector. A refractive treatment may be planned using matrix elements of the conditioned input vector.

In another aspect, the invention provides a method for planning a refractive treatment of an eye of a patient. The method comprises deriving an influence matrix from a plurality of prior eye treatments. For a particular eye and an associated particular treatment, an intended refractive correction vector (IRC) may be determined, with the IRC characterizing a difference between measured pre-treatment high-order aberrations and a target refraction. Similar IRC vectors may be prepared for each of the prior eye treatments. A surgically induced refractive correction vector (SIRC) may similarly be determined for each previously treated eye, with each SIRC characterizing a difference between the measured pre-treatment aberrations and measured post-treatment aberrations of that eye. The influence matrix can then be derived so as to provide a correlation between the IRCs and the SIRCs. A patient IRC vector can be defined characterizing a difference between measured pre-treatment high-order aberrations of the eye of the patient, and a target refraction of the eye of the patient. The patient IRC vector can then be adjusted to produce an adjusted IRC based on the influence matrix. In many embodiments, the patient will be treated based on the adjusted IRC.

In another aspect, the invention provides a method for planning a treatment of an eye of a patient. An influence matrix will preferably have been derived from a plurality of prior eye treatments. The influence matrix may be derived by determining a target refraction of each eye along with an intended refractive correction vector (IRC) characterizing a difference between pre-treatment high-order aberrations and the target. A surgically induced refraction correction vector (SIRC) will also be determined for each eye, with the SIRC characterizing a difference between the measured pre-treatment aberrations and measured post-treatment aberrations. The influence matrix will be derived so as to provide a correlation between the IRCs and the SIRCs. The method comprises receiving a patient IRC vector characterizing a difference between measured pre-treatment high-order aberrations of the eye of the patient and a target refraction of the eye of the patient. The IRC vector is adjusted based on the influence matrix. In many embodiments, the patient will then be treated based on the adjusted IRC.

In another aspect, the invention provides a system for planning a treatment of an eye of a patient. The system comprises an input for receiving pre-treatment high-order aberrations of the eye of the patient. A processor is coupled to the input. The processor derives the treatment of the eye of the patient in response to the high-order aberrations of the eye of the patient by applying an effective treatment vector function. The effective treatment vector function is derived from the correlation between pre-treatment vectors characterizing high-order aberrations and post-treatment vectors characterizing post-treatment high-order aberrations for each of a plurality of previously treated eyes. An output is coupled to the processor so as to transmit the treatment to facilitate improving refraction of the eye of the patient.

The processor will often comprise software in the form of tangible media embodying machine readable instructions for deriving the treatment. In exemplary embodiments, the processor is configured to generate and/or store an input vector for the eye of the patient in response to a target refraction that is desired to be induced by the treatment. The input vector can be generated by determining an intended refractive correction vector (IRC) characterizing a difference between pre-treatment measured aberrations of the eye and the target. Exemplary embodiments may include one or more aberrometer (such as a wavefront sensor) coupled to the input. The processor may be configured to derive the effective treatment vector function from a plurality of prior treatments using intended refractive correction vectors (IRCs) of the associated eyes to determine surgically induced refraction correction vectors (SIRCs) of the associated eyes, with each SIRC characterizing a difference between the measured pre-treatment aberrations and the post-treatment aberrations of the associated eye. Particularly preferred embodiments derive the effective treatment vector function using an influence matrix $\vec{\mathcal{F}}$ relating the SIRCs to the IRCs. $\vec{\mathcal{F}}$ can be derived such that for the associated eyes:

$$\vec{E} = \overrightarrow{SIRC} - \vec{\mathcal{F}} \cdot \overrightarrow{IRC}$$

in which $\vec{E}$ is an error vector. The effective treatment function can be applied to the input vector by calculating an adjusted intended refractive correction vector (AIRC) such that:

$$\overrightarrow{AIRC} = \vec{\mathcal{F}}^{-1} \cdot \overrightarrow{IRC}$$

in which $\vec{\mathcal{F}}^{-1}$ is an inverse of $\vec{\mathcal{F}}$, and in which IRC' is based on the IRC of the eye of the patient (optionally so as to incorporate physician input, nomograms, and/or the like). Advantageously, the processor may have an input for receiving physician adjustments to the IRC, nomogram adjustments to the IRC, and/or the like. The processor can define an IRC' for the eye of the patient by applying, to the IRC of the eye of the patient, these adjustments. The input vector can then be based on the IRC'.

Typically, the effective treatment vector function is based on an influence matrix. The planned treatment of the eye will typically comprise a planned treatment vector, and a plurality of the elements of the input vector can each alter a plurality of elements of the planned treatment vector. In other embodiments, a plurality of the planned treatment vector elements may each be altered by a plurality of the elements of the input vector. In fact, all of the refractive elements of the input vector may impact every element of the planned treatment vector through use of the exemplary influence matrix derivation approach.

In another aspect, the invention provides a system for planning a refractive treatment of an eye of a patient. The system comprises a processor having an input for receiving data regarding a plurality of prior eye treatments. The processor is configured so as to derive an influence matrix from the prior eye treatment data. The influence matrix may be derived by determining an intended refractive correction vector (IRC) characterizing a difference between measured pre-treatment high-order aberrations and target refractions of each eye associated with a prior eye treatment. A surgically induced refraction correction vector (SIRC) of each eye is determined by characterizing a difference between the measured pre-treatment aberrations and measured post-treatment aberrations, with a vector being determined for each associated eye. The influence matrix will generally comprise a correlation between the IRCs and the SIRCs. The system has an input for receiving a patient IRC vector characterizing a difference between measured pre-treatment high-order aberration of the eye of the patient and a target refraction of the eye of that patient. An output is coupled to the processor for transmitting a treatment. The processor is configured to derive the treatment by adjusting the patient IRC vector based on the influence matrix.

In yet another aspect, the invention provides a system for a refractive treatment of an eye of the patient. An influence matrix will have been derived from a plurality of prior eye treatments. The influence matrix is derived by, for each prior eye treatment of an associated eye, determining a target refraction of the associated eye along with an intended refractive correction vector characterizing the difference between measured pre-treatment high-order aberrations of the associated eye and the target. A surgically induced refraction correction vector (SIRC) is also determined for each eye, with the SIRC characterizing a difference between measured pre-treatment aberrations and measured post-treatment aberrations of that eye. The influence matrix is derived so as to provide a correlation between the IRCs and the SIRCs. The system comprises an input for receiving a patient IRC vector characterizing a difference between measured pre-treatment high-order aberrations of the eye of the patient and a target refraction of the eye of the patient. A processor is coupled to the input. The processor is configured for adjusting the patient IRC vector based on the influence matrix. Optionally, the adjusted IRC vector may be output to a high-order refraction correcting apparatus, such as a laser eye surgery system, the custom IOL lens fab system, a refractive femtosecond laser system, or the like.

In one aspect, embodiments of the present invention encompass methods for planning a refractive treatment of an eye of a patient. Exemplary methods may include determining an effective treatment vector function based on a plurality of prior eye treatments by, for each prior eye treatment of an associated eye, defining a pre-treatment vector characterizing measured pre-treatment optical properties of the associated eye, defining a post-treatment vector characterizing measured post treatment optical properties of the associated eye, and deriving the effective treatment vector function using a correlation between the pre-treatment vectors and the post-treatment vectors. Methods may also include defining an input vector based on measured pre-treatment optical properties of the eye of the patient, and deriving the treatment of the eye of the patient by applying the effective treatment vector function to the input vector. In some cases, the measured pre-treatment optical properties include a member selected from the group consisting of a low order aberration, a high order aberration, a corneal topography measurement, an optical coherence tomography measurement, and a corneal keratometry value. In some cases, the refractive treatment includes a member selected from the group consisting of an excimer laser treatment, a femtosecond laser treatment, an intraocular lens treatment, a contact lens treatment, and a spectacle treatment. In some cases, the process of defining the input vector includes identifying a target refraction of the eye of the patient to be induced by the refractive treatment, and determining an intended refractive correction vector (IRC) characterizing a difference between the measured pre-treatment aberrations of the eye of the patient and the target. The process of deriving the effective treatment vector function from prior treatments may include determining intended refractive correction vectors (IRCs) of the associated eyes, and determining surgically induced refractive correction vectors (SIRCs) of the associated eyes, where each SIRC characterizes a difference between the measured pre-treatment aberrations and the post-treatment aberrations of an associated eye. In some cases, the process of deriving the effective treatment vector function includes determining an influence matrix relating the SIRCs to the IRCs. In some cases, methods may include defining an IRC' for the eye of the patient by applying, to the IRC of the eye of the patient, at least one adjustment selected from the group consisting of physician adjustments to the IRC, and nomogram adjustments to the IRC. The input vector can be based on the IRC'. In some cases, the effective treatment vector function may be derived using an influence matrix. In some cases, the planned treatment of the eye of the patient is characterized by a planned treatment vector, and the influence matrix is derived such that a plurality of the elements of the input vector each alter a plurality of elements of the planned treatment vector. In some cases, the planned treatment of the eye of the patient is characterized by a planned treatment vector, and the influence matrix is derived such that a plurality of the planned treatment vector elements are each altered by a plurality of elements of the input vector. In some cases, the planned treatment of the eye of the patient is characterized by a planned treatment vector, and the influence matrix is derived such that every element of the input vector characterizing a refractive shape of the eye of the patient can alter every element of the planned treatment vector characterizing a change in the refractive shape of the eye of the patient. In some cases, the pre-treatment vectors and the input vector characterize refraction, non-refractive cofactors characterizing the patient and/or the treatment setting, and the optical properties of the eyes. In some cases, the treatment of the eye of the patient is derived by multiplying the influence matrix of the effective treatment vector function by the input vector so as to define a conditioned input vector, and by planning a refractive treatment with matrix elements of the conditioned input vector.

In another aspect, embodiments of the present invention encompass methods for planning a treatment of an eye of a patient. Exemplary methods may include deriving an influence matrix from a plurality of prior eye treatments by, for each prior eye treatment of an associated eye, determining an intended refractive correction vector (IRC) characterizing a difference between measured pre-treatment high-order aberrations of the associated eye and a target refraction of the associated eye, and determining a surgically induced refractive correction vector (SIRC) of the associated eye characterizing a difference between the measured pre-treatment aberrations and measured post-treatment aberrations of the associated eye. The influence matrix can be derived so as to provide a correlation between the IRCs and the SIRCs. Methods may also include defining a patient IRC vector characterizing a difference between measured pre-treatment high-order aberrations of the eye of the patient and a target refraction of the eye of the patient, and adjusting the patient IRC vector based on the influence matrix. In some cases, for each prior eye treatment of the associated eye, the IRC can be further determined so as to characterize a difference between measured pre-treatment low order aberrations and target low order aberrations, and so as to characterize a difference between measured pre-treatment corneal topography and target corneal topography, and the SIRC is further determined so as to characterize a difference between the measured pre-treatment low order aberrations and measured post-treatment aberrations, and so as to characterize a difference between measured the pre-treatment corneal topography and measured post-treatment corneal topography. The patient IRC vector can be further defined so as to characterize a difference between measured pre-treatment low order aberrations and the target refraction, and so as to characterize a difference between measured pre-treatment topography of the eye and target topography. In some cases, methods may include treating the patient based on the adjusted IRC.

In another aspect, embodiments of the present invention encompass methods for planning a refractive treatment of an eye of a patient. An influence matrix may have been derived from a plurality of prior eye treatments by, for each prior eye treatment of an associated eye, determining a target refraction of the associated eye, determining an intended refractive correction vector (IRC) characterizing a difference between measured pre-treatment optical properties of the associated eye and the target, and determining a surgically induced refractive correction vector (SIRC) of the associated eye characterizing a difference between the measured pre-treatment optical properties and measured post-treatment optical properties of the associated eye. The influence matrix can be derived so as to provide a correlation between the IRCs and the SIRCs. Methods may include receiving a patient IRC vector characterizing a difference between measured pre-treatment optical properties of the eye of the patient and a target refraction of the eye of the patient, and adjusting the patient IRC vector based on the influence matrix.

In still another aspect, embodiments of the present invention encompass systems for planning a refractive treatment of an eye of a patient. Exemplary systems may include an input for receiving pre-treatment optical properties of the eye of the patient, and a processor coupled to the input, the processor deriving the treatment of the eye of the patient in response to the optical properties of the eye of the patient by applying an effective treatment vector function. The effective treatment vector function can be derived from, for each of a plurality of prior eye treatments, a correlation between a pre-treatment vector characterizing optical properties of the associated eye before treatment, and a post-treatment vector characterizing post-treatment optical properties of the associated eye. Systems can also include an output coupled to the processor so as to transmit the treatment to facilitate improving refraction of the eye of the patient. In some cases, the pre-treatment optical properties of the eye of the patient can include at least one member selected from the group consisting of a low order aberration, a high order aberration, a corneal topography measurement, an optical coherence tomography measurement, and a corneal keratometry value. In some cases, for each of the plurality of prior eye treatments, the pre-treatment vector can characterize optical properties of the associated eye before treatment, and the optical properties may include one or more member selected from the group consisting of a low order aberration, a high order aberration, a corneal topography measurement, an optical coherence tomography measurement, and a corneal keratometry value. In some cases, the post-treatment vector may characterize optical properties of the associated eye before treatment, and the optical properties may include one or more member selected from the group consisting of a low order aberration, a high order aberration, a corneal topography measurement, an optical coherence tomography measurement, and a corneal keratometry value. In some cases, the output is configured to facilitate a refractive treatment including a member selected from the group consisting of an excimer laser treatment, a femtosecond laser treatment, an intraocular lens treatment, a contact lens treatment, and a spectacle treatment. In some cases, the processor includes tangible media embodying machine readable instructions for implementing the derivation of the treatment. In some cases, the processor is configured to generate an input vector for the eye of the patient in response to a target refraction of the eye of the patient to be induced by the refractive treatment by determining an intended refractive correction (IRC) characterizing a difference between measured pre-treatment aberrations of the eye of the patient and the target. In some cases, systems may include an aberrometer coupled to the input, the aberrometer sensing the low order aberrations of the eye and the high-order aberrations of an eye and transmitting the low and high-order aberrations to the processor. In some cases, the aberrometer is configured to sense corneal topography and to transmitting the corneal topography to the processor. In some cases, systems may include an optical coherence tomography measurement apparatus coupled to the input, the optical coherence tomography measurement apparatus sending the optical properties of an eye and transmitting the optical properties to the processor. In some cases, systems may include a keratometry apparatus coupled to the input, the keratometry apparatus sensing the optical properties of an eye and transmitting the optical properties to the processor. In some cases, the processor can be configured to derive the effective treatment vector function from prior treatments in response to intended refractive correction vectors (IRCs) of the associated eyes and to determine surgically induced refractive correction vectors (SIRCs) of the associated eyes, each SIRC characterizing a difference between the measured pre-treatment aberrations and the post-treatment aberrations of an associated eye. In some cases, the effective treatment vector function can be based on an influence matrix relating the SIRCs to the IRCs. In some cases, systems may include an additional input coupled to the processor for receiving at least one adjustment selected from the group consisting of physician adjustments to the IRC, and nomogram adjustments to the IRC. The processor can be configured to define an IRC' for the eye of the patient by applying, to the IRC of the eye of the patient, the at least one adjustment, the input vector being based on the IRC'. In some cases, the effective treatment vector function can be based on an influence matrix. In some cases, the planned treatment of the eye of the patient may include a planned treatment vector, and a plurality of the elements of the input vector may each alter a plurality of elements of the planned treatment matrix, and/or a plurality of the planned treatment vector elements may each be altered by a plurality of elements of the input vector. In some cases, an input vector includes refractive elements characterizing refraction of the eye of the patient, non-refractive co-factors characterizing the patient and/or the treatment setting, and elements characterizing the optical properties of the eye. In some cases, elements characterizing the optical properties of the eye can include a member selected from the group consisting of a high order element characterizing a high order aberration of the eye, a low order element characterizing a low order aberration of the eye, a corneal topography measurement element characterizing a corneal topography measurement of the eye, an optical coherence tomography measurement element characterizing an optical coherence topography measurement of the eye, and a corneal keratometry value element characterizing a corneal keratometry value of the eye. In some cases, a processor can be configured to derive the treatment of the eye of the patient by multiplying the influence matrix of the effective treatment vector function by the input vector.

In yet another aspect, embodiments of the present invention encompass systems for planning a refractive treatment of an eye of a patient. Exemplary systems may include a processor having an input for receiving data regarding a plurality of prior eye treatments and for deriving an influence matrix therefrom by, for each prior eye treatment of an associated eye, determining an intended refractive correction vector (IRC) characterizing a difference between measured pre-treatment high-order aberrations of the associated eye and a target refraction of the associated eye, and determining a surgically induced refractive correction vector (SIRC) of the associated eye characterizing a difference between the measured pre-treatment aberrations and measured post-treatment aberrations of the associated eye. In some cases, the influence matrix can include a correlation between the IRCs and the SIRCs. In some cases, systems may also include another input for receiving a patient IRC vector characterizing a difference between measured pre-treatment high-order aberrations of the eye of the patient and a target refraction of the eye of the patient. In some cases, systems may also include an output coupled to the processor for transmitting a treatment, the processor configured to derive the treatment by adjusting the patient IRC vector based on the influence matrix. In some cases, pre-treatment optical properties of the eye of the patient can include at least one member selected from the group consisting of a low order aberration, a high order aberration, a corneal topography measurement, an optical coherence tomography measurement, and a corneal keratometry value. In some cases, for each of the plurality of prior eye treatments, the pre-treatment vector may characterize optical properties of the associated eye before treatment, and the optical properties may include one or more member selected from the group consisting of a low order aberration, a high order aberration, a corneal topography measurement, an optical coherence tomography measurement, and a corneal keratometry value. In some cases, a post-treatment vector may characterize optical properties of the associated eye before treatment. Optical properties may include one or more member selected from the group consisting of a low order aberration, a high order aberration, a corneal topography measurement, an optical coherence tomography measurement, and a corneal keratometry value. In some cases, measured pre-treatment optical properties of the eye of the patient may include a member selected from the group consisting of a low order aberration, a high order aberration, a corneal topography measurement, an optical coherence tomography measurement, and a corneal keratometry value. In some cases, a refractive treatment may include a member selected from the group consisting of an excimer laser treatment, a femtosecond laser treatment, an intraocular lens treatment, a contact lens treatment, and a spectacle treatment. In some cases, systems may also include a laser eye surgery apparatus coupled to the output, where the surgery apparatus generates a laser beam for treating the patient based on the adjusted IRC.

In another aspect, embodiments of the present invention encompass systems for planning a treatment of an eye of a patient. An influence matrix may have been derived from a plurality of prior eye treatments by, for each prior eye treatment of an associated eye, determining a target refraction of the associated eye, determining an intended refractive correction vector (IRC) characterizing a difference between measured pre-treatment optical properties of the associated eye and the target, and determining a surgically induced refractive correction vector (SIRC) of the associated eye characterizing a difference between the measured pre-treatment aberrations and measured post-treatment aberrations of the associated eye. The influence matrix may also be derived so as to provide a correlation between the IRCs and the SIRCs. The system may include an input for receiving a patient IRC vector characterizing a difference between measured pre-treatment optical properties of the eye of the patient and a target refraction of the eye of the patient. In some cases, the system may include a processor coupled to the input, where the processor is configured for adjusting the patient IRC vector based on the influence matrix. In some cases, the measured pre-treatment optical properties of the associated eye may include a member selected from the group consisting of a low order aberration, a high order aberration, a corneal topography measurement, an optical coherence tomography measurement, and a corneal keratometry value. In some cases, the measured pre-treatment optical properties of the eye of the patient may include a member selected from the group consisting of a low order aberration, a high order aberration, a corneal topography measurement, an optical coherence tomography measurement, and a corneal keratometry value. In some cases, the refractive treatment may include a member selected from the group consisting of an excimer laser treatment, a femtosecond laser treatment, an intraocular lens treatment, a contact lens treatment, and a spectacle treatment. In some cases, the influence matrix can be based on a correlation between a pre-treatment cylinder value, a post-treatment sphere value, and a pre-treatment keratometry value of the associated eye. In some cases, the influence matrix can be based on a correlation between a pre-treatment keratometry value of the associated eye and a high order aberration of the associated eye, for example a pre-treatment high order aberration, or a post-treatment aberration.

In yet another aspect, embodiments of the present invention encompass systems for planning a treatment of an eye of a patient having an eye with a natural lens. Exemplary systems may include an input for receiving pre-treatment optical properties of the eye of the patient with the natural lens, and a processor coupled to the input, where the processor derives the treatment of the eye of the patient in response to the optical properties of the eye of the patient by applying an effective treatment vector function, where the effective treatment vector function is derived from, for each of a plurality of prior eye treatments, a correlation between a pre-treatment vector characterizing optical properties of the associated eye with an associated lens therein, and a post-treatment vector characterizing post-treatment optical properties of the associated eye after removal of the natural lens and implantation of an associated intraocular lens. Systems may also include an output coupled to the processor so as to transmit the treatment to facilitate improving refraction of the eye of the patient.

In one aspect, embodiments of the present invention encompass systems for treating an eye of a patient, where the eye has an anterior surface. Exemplary systems may include an input for receiving pre-treatment optical properties of the eye of the patient, and a processor coupled to the input. The processor can be configured to derive the treatment of the eye of the patient in response to the optical properties of the eye of the patient by applying an effective treatment vector function, where the effective treatment vector function is derived from, for each of a plurality of prior eye treatments, a correlation between a pre-treatment vector characterizing optical properties of the associated eye before treatment, and a post-treatment vector characterizing post-treatment optical properties of the associated eye. Systems may also include a femtosecond laser system coupled to the processor so as to focus a pattern of femtosecond laser energy through the anterior surface of the eye of the patient such that the refractive treatment is effected within the eye of the patient.

In a further aspect, embodiments of the present invention encompass methods for planning a cataract surgery on an eye of a patient. Exemplary methods may include: determining an effective treatment vector function based on a plurality of prior corrective surgeries by: for each prior corrective surgery on an associated eye: defining a pre-surgery vector characterizing measured pre-surgery high-order aberrations of the associated eye; defining a post-surgery vector characterizing measured post-surgery high-order aberrations of the associated eye; deriving the effective surgery vector function using a correlation between the pre-surgery vectors and the post-surgery vectors; defining an input vector based on measured pre-surgery high-order aberrations of the eye of the patient; and deriving one or more parameters of an intraocular lens (IOL) to be implanted into the eye of the patient by applying the effective surgery vector function to the input vector.

In yet a further aspect, embodiments of the present invention encompass methods for planning a cataract surgery on an eye of a patient. Exemplary methods may include: deriving an influence matrix from a plurality of prior surgeries by, for each prior corrective surgery on an associated eye: determining an intended refractive correction vector (IRC) characterizing a difference between measured pre-surgery high-order aberrations of the associated eye and a target refraction of the associated eye; and determining a surgically induced refractive correction vector (SIRC) of the associated eye characterizing a difference between the measured pre-surgery aberrations and measured post-surgery aberrations of the associated eye, wherein the influence matrix is derived so as to provide a correlation between the IRCs and the SIRCs; defining a patient IRC vector characterizing a difference between measured pre-surgery high-order aberrations of the eye of the patient and a target refraction of the eye of the patient; and adjusting the patient IRC vector based on the influence matrix.

In a still further aspect, embodiments of the present invention encompass methods for planning a cataract surgery on an eye of a patient, where an influence matrix has been derived from a plurality of prior surgeries by, for each prior corrective surgery of an associated eye, determining a target refraction of the associated eye, determining an intended refractive correction vector (IRC) characterizing a difference between measured pre-surgery high-order aberrations of the associated eye and the target, and determining a surgically induced refractive correction vector (SIRC) of the associated eye characterizing a difference between the measured pre-surgery aberrations and measured post-surgery aberrations of the associated eye, the influence matrix derived so as to provide a correlation between the IRCs and the SIRCs. Exemplary methods may include: receiving a patient IRC vector characterizing a difference between measured pre-surgery high-order aberrations of the eye of the patient and a target refraction of the eye of the patient; and adjusting the patient IRC vector based on the influence matrix.

In yet still a further aspect, embodiments of the present invention encompass systems for planning a cataract surgery on an eye of a patient. Exemplary systems may include: an input for receiving pre-surgery high-order aberrations of the eye of the patient; a processor coupled to the input, the processor deriving one or more parameters of an intraocular lens (IOL) to be implanted into the eye of the patient in response to the high-order aberrations of the eye of the patient by applying an effective surgery vector function, wherein the effective surgery vector function is derived from, for each of a plurality of prior corrective surgeries, a correlation between a pre-surgery vector characterizing high-order aberrations of the associated eye before surgery, and a post-surgery vector characterizing post-surgery high-order aberrations of the associated eye; and an output coupled to the processor so as to transmit the one or more parameters of the IOL to be implanted into the eye of the patient.

In an additional aspect, embodiments of the present invention encompass systems for planning cataract surgery on an eye of a patient. Exemplary systems may include: a processor having: an input for receiving data regarding a plurality of prior corrective surgeries, and for deriving an influence matrix therefrom by, for each prior corrective surgery of an associated eye: determining an intended refractive correction vector (IRC) characterizing a difference between measured pre-surgery high-order aberrations of the associated eye and a target refraction of the associated eye; and determining a surgically induced refractive correction vector (SIRC) of the associated eye characterizing a difference between the measured pre-surgery aberrations and measured post-surgery aberrations of the associated eye; wherein the influence matrix comprises a correlation between the IRCs and the SIRCs; and another input for receiving a patient IRC vector characterizing a difference between measured pre-surgery high-order aberrations of the eye of the patient and a target refraction of the eye of the patient; and an output coupled to the processor for transmitting a one or more parameters of an intraocular lens (IOL) to be implanted into the eye of the patient in the cataract surgery on the eye of the patient, the processor configured to derive one or more parameters of the IOL to be implanted into the eye of the patient by adjusting the patient IRC vector based on the influence matrix.

In yet an additional aspect, embodiments of the present invention encompass systems for planning a cataract surgery on an eye of a patient where an influence matrix has been derived from a plurality of prior corrective surgeries by, for each prior corrective surgery on an associated eye, determining a target refraction of the associated eye, determining an intended refractive correction vector (IRC) characterizing a difference between measured pre-surgery high-order aberrations of the associated eye and the target, and determining a surgically induced refractive correction vector (SIRC) of the associated eye characterizing a difference between the measured pre-surgery aberrations and measured post-surgery aberrations of the associated eye, the influence matrix derived so as to provide a correlation between the IRCs and the SIRCs. Exemplary systems may include: an input for receiving a patient IRC vector characterizing a difference between measured pre-surgery high-order aberrations of the eye of the patient and a target refraction of the eye of the patient; and a processor coupled to the input, the processor configured for adjusting the patient IRC vector based on the influence matrix.

In still another additional aspect, embodiments of the present invention encompass methods for planning a cataract surgery on an eye of a patient. Exemplary methods may include: determining an effective surgery vector function based on a plurality of prior eye treatments by: for each prior eye treatment of an associated eye: defining a pre-surgery vector characterizing measured pre-surgery optical properties of the associated eye; defining a post-surgery vector characterizing measured post-surgery optical properties of the associated eye; deriving the effective surgery vector function using a correlation between the pre-surgery vectors and the post-surgery vectors; defining an input vector based on measured pre-surgery optical properties of the eye of the patient; and deriving the treatment of the eye of the patient by applying the effective surgery vector function to the input vector.

In a yet further aspect, embodiments of the present invention encompass methods for planning a cataract surgery on an eye of a patient. Exemplary methods may include: deriving an influence matrix from a plurality of prior corrective surgeries by, for each prior surgery on an associated eye: determining an intended refractive correction vector (IRC) characterizing a difference between measured pre-surgery high-order aberrations of the associated eye and a target refraction of the associated eye; and determining a surgically induced refractive correction vector (SIRC) of the associated eye characterizing a difference between the measured pre-surgery aberrations and measured post-surgery aberrations of the associated eye, wherein the influence matrix is derived so as to provide a correlation between the IRCs and the SIRCs; defining a patient IRC vector characterizing a difference between measured pre-surgery high-order aberrations of the eye of the patient and a target refraction of the eye of the patient; and adjusting the patient IRC vector based on the influence matrix.

In another additional aspect, embodiments of the present invention encompass methods for planning a cataract surgery on an eye of a patient, where an influence matrix has been derived from a plurality of prior corrective surgeries by, for each prior corrective surgery on an associated eye, determining a target refraction of the associated eye, determining an intended refractive correction vector (IRC) characterizing a difference between measured pre-surgery optical properties of the associated eye and the target, and determining a surgically induced refractive correction vector (SIRC) of the associated eye characterizing a difference between the measured pre-surgery optical properties and measured post-surgery optical properties of the associated eye, the influence matrix derived so as to provide a correlation between the IRCs and the SIRCs. Exemplary methods may include: receiving a patient IRC vector characterizing a difference between measured pre-surgery optical properties of the eye of the patient and a target refraction of the eye of the patient; and adjusting the patient IRC vector based on the influence matrix.

In yet another additional aspect, embodiments of the present invention encompass systems for planning a cataract surgery on an eye of a patient. Exemplary systems may include: an input for receiving pre-surgery optical properties of the eye of the patient; a processor coupled to the input, the processor deriving one or more parameters of an intraocular lens (IOL) to be implanted into the eye of the patient in the cataract surgery on the eye of the patient in response to the optical properties of the eye of the patient by applying an effective surgery vector function, wherein the effective surgery vector function is derived from, for each of a plurality of prior corrective surgeries, a correlation between a pre-surgery vector characterizing optical properties of the associated eye before surgery, and a post-surgery vector characterizing post-surgery optical properties of the associated eye; and an output coupled to the processor so as to transmit the one or more parameters of the IOL to be implanted into the eye of the patient in the cataract surgery.

In still another additional aspect, embodiments of the present invention encompass systems for planning a cataract surgery on an eye of a patient. Exemplary systems may include: a processor having an input for receiving data regarding a plurality of prior corrective surgeries and for deriving an influence matrix therefrom by, for each prior corrective surgery on an associated eye: determining an intended refractive correction vector (IRC) characterizing a difference between measured pre-surgery high-order aberrations of the associated eye and a target refraction of the associated eye, and determining a surgically induced refractive correction vector (SIRC) of the associated eye characterizing a difference between the measured pre-surgery aberrations and measured post-surgery aberrations of the associated eye, wherein the influence matrix comprises a correlation between the IRCs and the SIRCs, and another input for receiving a patient IRC vector characterizing a difference between measured pre-surgery high-order aberrations of the eye of the patient and a target refraction of the eye of the patient; and an output coupled to the processor for transmitting tone or more parameters of an intraocular lens (IOL) to be implanted into the eye of the patient in the cataract surgery, the processor configured to derive the one or more parameters of the IOL by adjusting the patient IRC vector based on the influence matrix.

In an additional further aspect, embodiments of the present invention encompass systems for planning a cataract surgery on an eye of a patient, where an influence matrix has been derived from a plurality of prior corrective surgeries by, for each prior corrective surgery on an associated eye, determining a target refraction of the associated eye, determining an intended refractive correction vector (IRC) characterizing a difference between measured pre-surgery optical properties of the associated eye and the target, and determining a surgically induced refractive correction vector (SIRC) of the associated eye characterizing a difference between the measured pre-surgery aberrations and measured post-surgery aberrations of the associated eye, the influence matrix derived so as to provide a correlation between the IRCs and the SIRCs. Exemplary systems include: an input for receiving a patient IRC vector characterizing a difference between measured pre-surgery optical properties of the eye of the patient and a target refraction of the eye of the patient; and a processor coupled to the input, the processor configured for adjusting the patient IRC vector based on the influence matrix.

DETAILED DESCRIPTION OF THE INVENTION

Figure 1:
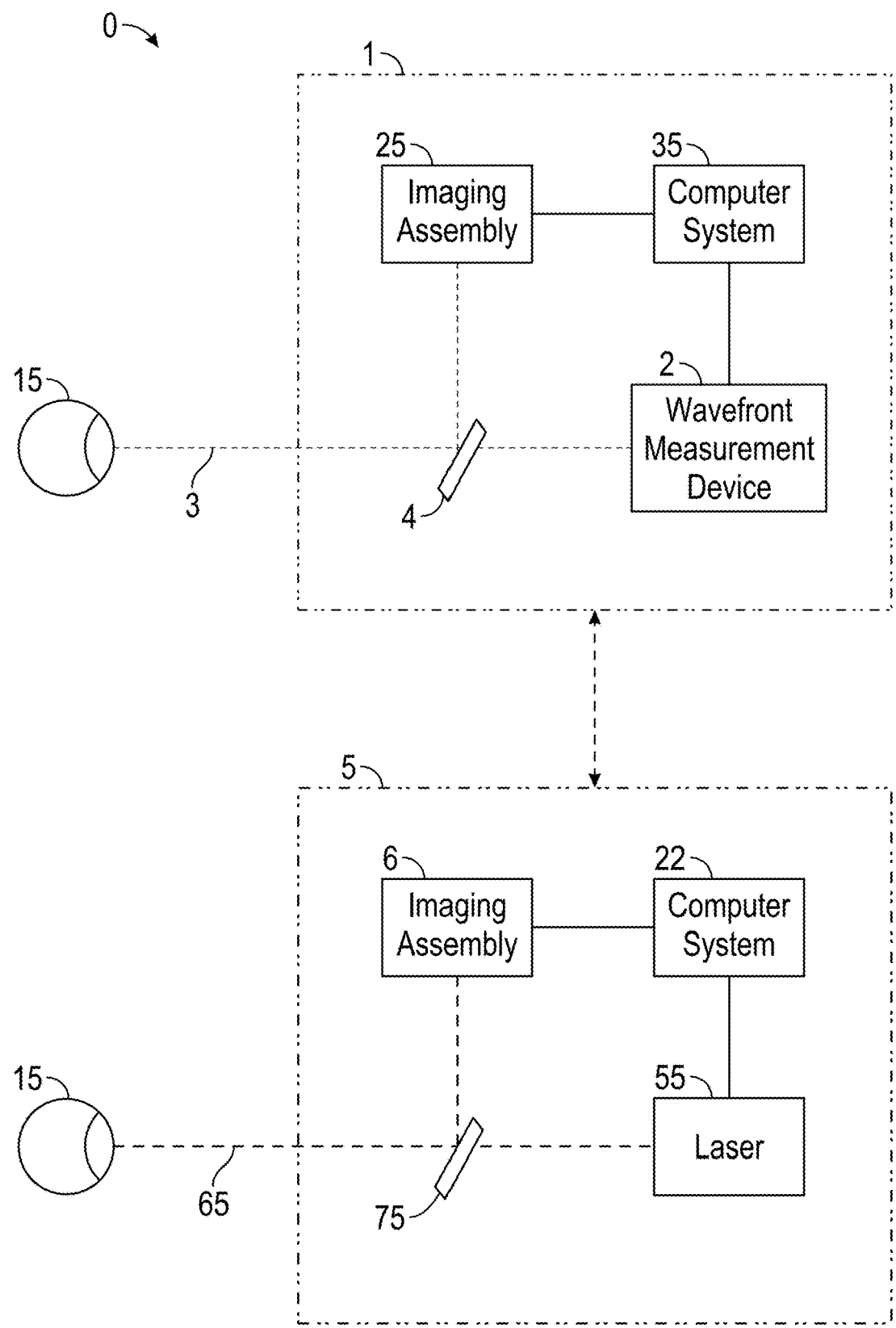
FIG. 1 schematically illustrates a system and method for measurement and treatment of refractive defects of an eye of a patient.

The present invention generally provides improved devices, systems, and methods for diagnosing, planning treatments of, and/or treating the refractive structures of an eye of a patient. Exemplary embodiments of the invention make use of recent developments in measurement of refractive properties of the eye, and particularly the tools now available (and/or now being developed) to identify and characterize high-order aberrations of the eye of human patients. Along with the now widely used Hartmann-Shack and other wavefront sensors used to measure aberrations throughout the optical system of the eye, the measurement data and systems employed by embodiments of the invention may include topography, pachymetry, pupilometry, keratometry, refractometry, biometry, and/or the like. The optical tissue treatment modalities employed by the methods and systems described herein will often include ablative laser treatments (typically with an excimer or solid-state laser), but may alternatively employ intra-tissue photoaltering technologies such as intrastromal femtosecond laser treatments to form incisions so as to alter the shape of the cornea, or the like. Still further alternative therapies may be directed to altering the effective shape or function of optical tissues of the eye other than the cornea, such as by altering or replacing the lens, altering the structure of the capsular bag, and the like. Hence, a wide variety of measurement and/or treatment modalities may be employed in various embodiments of the invention.

Embodiments of the inventions described herein will go beyond prior attempts to identify and characterize specific couplings between optical refractive treatment shapes and potential inducement of an associated high-order aberration. Exemplary embodiments may identify and accurately characterize complex cross-relationships between pre-treatment refractive error modes of the eye and related post-prescriptive shape modifications that enhance overall viewing capabilities of a patient. These aberration/treated eye inter-mode relationships may be, at least in part, specific to an eye treatment modality (such as to ablative resculpting of the eye with a laser eye surgery system), specific to a particular treatment implementation hardware structure (for example, to a specific excimer laser geometry and assembly design, optical train, scanning mechanism, or the like) or even to a specific treatment controlling software package (such as to a shot-pattern generating software package which identifies excimer laser shots so as to produce an approximation to the desired overall refractive resculpting treatment shape). The couplings may also relate to healing effects of the eye, so that compensation for aberration/treated eye couplings may benefit from prior experience with the gradual changes in the tissues that take place in the hours, weeks, and/or ideally months after the treatment is completed.

So as to more effectively gauge and characterize the actual effect of an overall prescription, embodiments of the invention will often make use of measurements from a number of different prior treatments. Preferably, the prior treatments will have employed measurement and/or treatment systems sharing common components, technologies, and the like with the refractive treatment to be planned on a particular patient's eye. In many cases, at least some of the prior treatments from which information will be derived may have been diagnosed and/or treated with treatment components, techniques, and/or under circumstances which differ from those of the refractive treatment to be planned. Nonetheless, by gathering accurate data from the prior treatments, the overall accuracy of the treatment to be planned may be enhanced. More specifically, along with obtaining accurate pre-treatment data characterizing the eyes, embodiments of the methods and systems described herein will benefit significantly from high-order aberration measurements obtained after the treatment of a plurality of eyes, with the post-treatment data ideally being obtained a sufficient time after the treatment has been imposed so as to allow the eye to substantially stabilize and refraction-altering healing response of the treated tissues to substantially terminate. Vector analysis of the pre-treatment high-order aberration measurements and the post-treatment high-order aberration measurements, ideally using an influence matrix approach, allows complex couplings between intended refractive treatments and the overall effective refractive treatments to be identified and used for the future planned treatment of a particular patient's eye.

Along with the pre-treatment measurements and the post-treatment measurements, a variety of co-factors may also be included in the vector analysis and calculations employed in many embodiments of the present invention. Tissue response and healing effects may be influenced by biometric co-factors, such as the patient's age, gender, race, and/or the like. Specific identification of the measurement and/or treatment system components may be included among the co-factors by identification of a treatment laser system model, a measurement system type identifier, a specific measurement system identification, the identification of the diagnosing and/or treating physician, treatment and/or measurement ambient room temperatures and humidities, measurement or treatment times during the day, patient apprehension levels, and the like. Exemplary embodiments may still allow physicians to input adjustment factors and nomogram adjustments so as to alter the overall refractive prescription per a physician's experience. Advantageously, the ablation shot tissue removal basis and data used in calculating the shot numbers and locations so as to approximate an overall desired refractive prescription shape need not be altered to take advantage of the improvements provided by the inventions described herein. Additionally, the holistic vector function approach described herein is compatible with more specific analysis of factors which influence specific couplings between an intended change in the refractive properties of a patient's eye and the resultant high-order changes, so that analysis of the components of the influence function (or other matrix analysis components) can be performed and values may even be prophetically revised to reflect new changes in the overall measurement and/or treatment components.

FIG. 1 schematically illustrates a simplified system 0 according to an embodiment of the invention. System 0 includes a measurement device 1 used during a measurement procedure and a laser surgery system 5 used during a treatment procedure. The measurement and diagnostic procedure for a particular eye may precede the treatment the procedure on that eye by minutes, hours, days, or weeks. A timed series of measurements may be taken, with times between measurements optionally being quite short, though in some cases being several days or weeks apart so that stability of the measurements can be checked. Measurements will also often be acquired after the treatment is complete, with at least some of the measurements ideally being acquired a significant time after treatment so as to allow healing and any other tissue responses to the treatment to fully progress and for the treated eye to return to a substantially stabilized refractive system.

Exemplary measurement system 1 includes a wavefront measurement device 2 such as a Hartmann-Shack wavefront aberrometer. An imaging assembly 25 is also included to capture an image of the eye at substantially the same time (so that the eye does not move between the image and the measurement) that wavefront measurement device 2 directs a beam 3 toward the eye 15 of a patient in a measurement procedure. Directing of the laser beam 3, acquisition of the measurement data, capturing of the image and other measurement parameters are under the direction of an overall computer system 35 of the system 0. As the wavefront measurement and image are substantially contemporaneous, and as the structures of the imaging assembly in the measurement device are optically and/or mechanically coupled, the location information included in the image and the measurement can be associated.

In some embodiments, the computer system 35 of the image capture device 1 may also generate and save additional treatment information, such as a planned ablation profile or desired laser resculpting. Such treatment information can be generated from the data acquired by wavefront measurement device 2, and may be downloaded from measurement system 1 to a processor 22 of laser treatment device 5. Suitable measurement systems may include structures such as (or based on) the WaveScan Wavefront® system commercial available from Abbott Medical Optics, Inc. (AMO) of Santa Ana, Calif.; the Zyoptix® measurement workstation commercial available from Bosch and Lomb of Rochester, N.Y., and others. Exemplary measurement systems may include integrated wavefront and topographic systems such as those being developed for commercial and clinical use by TopCon Corporation of Japan, such as the iDesign System developed by Abbott Medical Optics of California, and the like. Hence, along with overall measurement of the aberrations throughout the optical system of the eye, the aberration data may more specifically identify the source of the aberrations, such as through topographic measurements of the anterior surface of the cornea, measurements of the posterior surface of the cornea (via optical coherence tomography, OCT) measurements of the size, shape, and aberrations of the crystalline lens, and the like.

The laser system 5 includes a laser 55 such as an excimer laser, a femtosecond laser, or the like. An imaging assembly 6 obtains an image of the eye, and as the images can be acquired substantially contemporaneously with refractive treatment of the eye using laser 55, registration of the treatment images from imaging assembly 6 and measurement images from imaging assembly 25 allow the therapeutic laser beam 65 to be accurately directed to eye 15. Registration of the images and directing of the laser beam are performed by processor 22. In the exemplary embodiment, processor 22 directs pulses of excimer laser energy toward stromal tissue of the cornea so as to effect volumetric reshaping of the cornea. Alternative refractive laser systems may employ femtosecond pulses to form an incision, and in some embodiments, separate lasers may be employed to first cut a flap in the cornea to expose the stroma underlying the epithelial tissue, and thereafter volumetrically resculpt the exposed stroma so as to alter the refractive characteristics of eye 15. In some embodiments, the ablation profile generated by other components of processor 22 for calculation of a desired refractive correction in the components of treatment system 5. Hence, the overall computer system of the combined devices may generally be referred to as a single computer system 35, of which processor 22 is a component. Specific processing tasks may be performed by any of a wide variety of processors, and/or by software organized into a wide variety of subroutines.

Figure 1A:
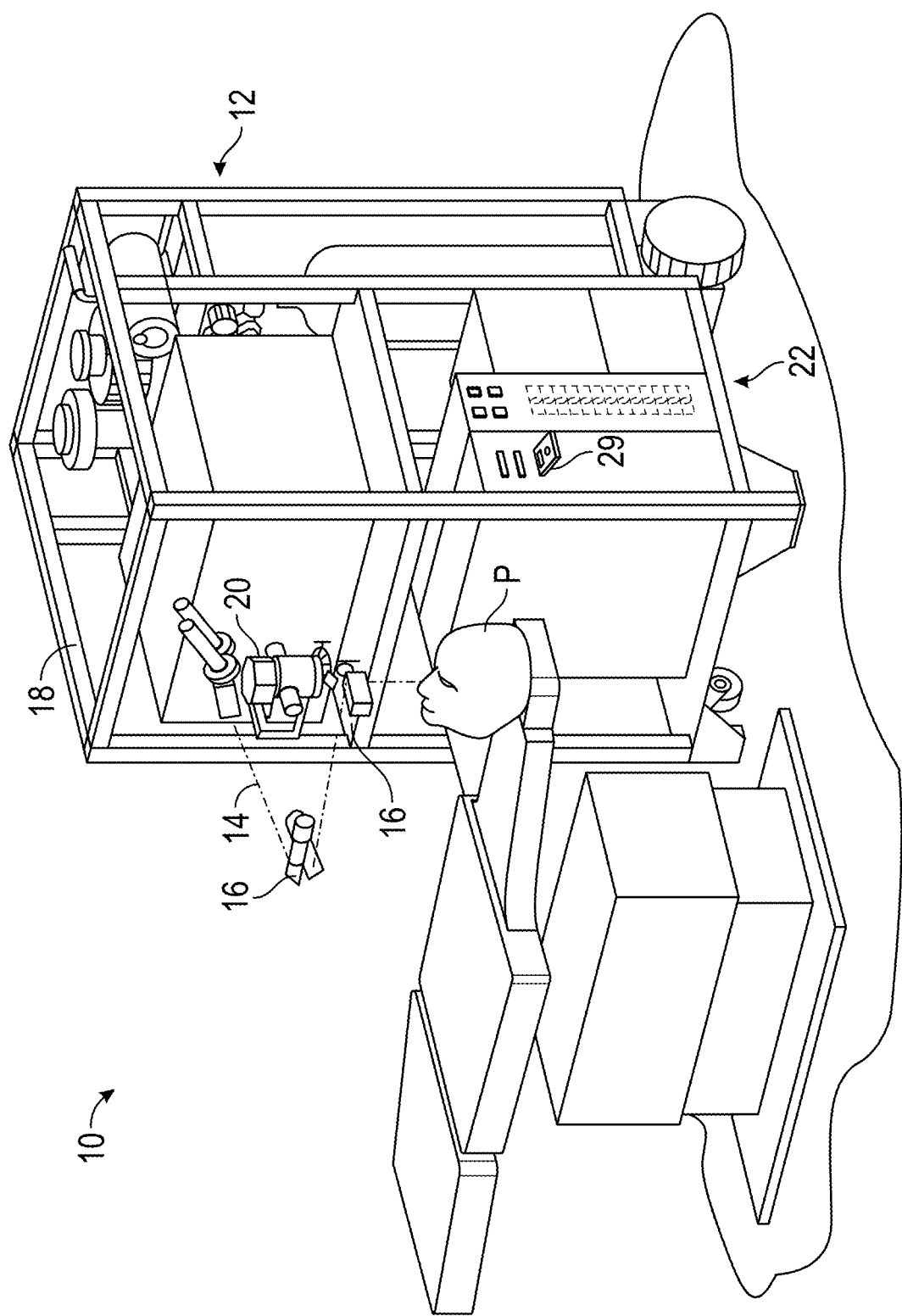
FIG. 1A is a perspective view schematically illustrating a refractive treatment of an eye of a patient using a laser eye surgery system, as may be included in the system of FIG. 1.

Referring now to FIG. 1A, a laser eye surgery system 10 may be employed as treatment system 5 in the schematic of FIG. 1. Laser eye surgery system 10 includes a laser 12 that produces a laser beam 14. Laser 12 is optically coupled to a laser delivery optic system 16, which directs laser beam 14 to an eye of patient P. The delivery optics support structure (not shown here for clarity) extends from a frame 18 supporting laser 12. A microscope 20 is mounted on the delivery optics support structure, the microscope often being used to image the cornea of the eye.

Processor 22 of laser system 10 may comprise (or interface with) a conventional PC system including the standard user interface devices such as a keyboard, a display monitor, and the like. Processor 22 will typically include an input device such as a magnetic or optical disk drive, an internet connection, or the like. Such input devices will often be used to download a computer executable code from a tangible storage media 29 embodying any of the methods of the present invention. Tangible storage media 29 may take the form of a floppy disk, an optical disk, a data tape, a volatile or non-volatile memory, RAM, or the like, and the processor 22 will include the memory boards and other standard components of modern computer systems for storing and executing this code. Tangible storage media 29 may also optionally embody wavefront sensor data, wavefront gradients, a wavefront elevation map, a treatment map, a corneal elevation map, and/or an ablation table. While tangible storage media 9, will often by used directly in cooperation with an input device of processor 22, the storage media may also be remotely operatively coupled with processor by means of network connections such as the internet, and by wireless methods such as infrared, Bluetooth, or the like. Many other hardware system architectures could also be implemented.

Laser 12 and delivery optics 16 will generally direct laser beam 14 to the eye of patient P under the direction of processor 22. Processor 22 will often selectively adjust laser beam 14 to expose portions of the cornea to the pulses of laser energy so as to effect a predetermined sculpting of the cornea and alter the refractive characteristics of the eye. In many embodiments, both laser beam 14 and the laser delivery optical system 16 will be under computer control of processor 22 to effect the desired laser sculpting process, with the processor effecting (and optionally modifying) the pattern of laser pulses. The pattern of pulses may by summarized in machine readable data of tangible storage media 29 in the form of a treatment table.

Laser beam 14 may be adjusted to produce the desired sculpting using a variety of alternative mechanisms. The laser beam 14 may be selectively limited using one or more variable apertures. The laser beam may also be tailored by varying the size and offset of the laser spot from an axis of the eye. Still further alternatives are possible, including scanning of the laser beam over the surface of the eye and controlling the number of pulses and/or dwell time at each location; using masks in the optical path of laser beam 14 which ablate to vary the profile of the beam incident on the cornea; hybrid profile-scanning systems in which a variable size beam (typically controlled by a variable width slit and/or variable diameter iris diaphragm) is scanned across the cornea; or the like. The optical and electromechanical computer programs, hardware, and control methodology for these laser pattern tailoring techniques are well described in the patent literature.

Additional components and subsystems may be included with laser system 10, as should be understood by those of skill in the art. For example, spatial and/or temporal integrators may be included to control the distribution of energy within the laser beam. Optional ablation effluent evacuators/filters, aspirators, and other ancillary components of the laser surgery system are known in the art. Suitable systems may also include commercially available refractive laser systems manufactured and/or sold by Abbott Medical Optics, Alcon, Bausch & Lomb, Nidek, WaveLight, LaserSight, Schwind, Carl Zeiss Meditec AG, and the like.

Figure 2:
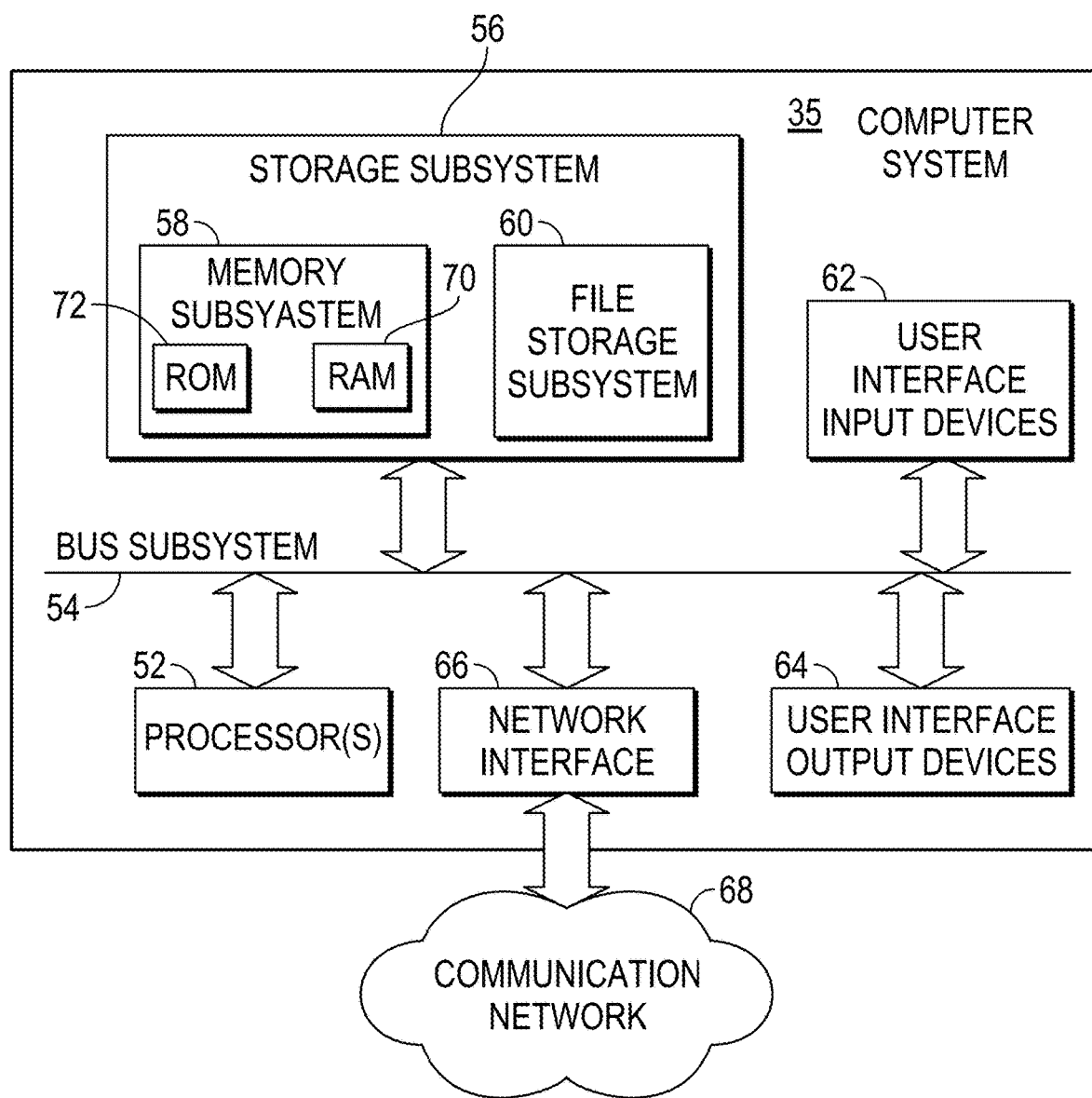
FIG. 2 schematically illustrates components of a simplified computer system for use in the measurement and/or treatment components of the system of FIG. 1.

FIG. 2 is a simplified block diagram of exemplary overall computer system 35 that may be used by the system 0 (see FIGS. 1 and 1A) of the present invention. Computer system 35 typically includes at least one processor 52 (and, optionally, processor 22) which may communicate with a number of peripheral devices via a bus subsystem 54. These peripheral devices may include a storage subsystem 56, comprising a memory subsystem 58 and a file storage subsystem 60, user interface input devices 62, user interface output devices 64, and a network interface subsystem 66. Network interface subsystem 66 provides an interface to outside networks 68 and/or other devices, such as the wavefront measurement system 30.

User interface input devices 62 may include a keyboard, pointing devices such as a mouse, trackball, touch pad, or graphics tablet, a scanner, foot pedals, a joystick, a touch-screen incorporated into the display, audio input devices such as voice recognition systems, microphones, and other types of input devices. User input devices 62 will often be used to download a computer executable code from a tangible storage media 29 embodying any of the methods of the present invention. In general, use of the term "input device" is intended to include a variety of conventional and proprietary devices and ways to input information into computer system 35.

User interface output devices 64 may include a display subsystem, a printer, a fax machine, or non-visual displays such as audio output devices. The display subsystem may be a cathode ray tube (CRT), a flat-panel device such as a liquid crystal display (LCD), a projection device, or the like. The display subsystem may also provide a non-visual display such as via audio output devices. In general, use of the term "output device" is intended to include a variety of conventional and proprietary devices and ways to output information from computer system 35 to a user.

Storage subsystem 56 can store the basic programming and data constructs that provide the functionality of the various embodiments of the present invention. For example, a database and modules implementing the functionality of the methods of the present invention, as described herein, may be stored in storage subsystem 56. These software modules are generally executed by processor 52, and/or by processor 22 (see FIGS. 1 and 1A). In a distributed environment, the software modules may be separated and stored on a plurality of computer systems 22, 35 and executed by processors of the plurality of computer systems. Storage subsystem 56 typically comprises memory subsystem 58 and file storage subsystem 60.

Memory subsystem 58 typically includes a number of memories including a main random access memory (RAM) 70 for storage of instructions and data during program execution and a read only memory (ROM) 72 in which fixed instructions are stored. File storage subsystem 60 provides persistent (non-volatile) storage for program and data files, and may include tangible storage media 29 (FIG. 1A) which may optionally embody wavefront sensor data, wavefront gradients, a wavefront elevation map, a treatment map, and/or an ablation table. File storage subsystem 60 may include a hard disk drive, a floppy disk drive along with associated removable media, a Compact Digital Read Only Memory (CD-ROM) drive, an optical drive, DVD, CD-R, CD-RW, solid-state removable memory, and/or other removable media cartridges or disks. One or more of the drives may be located at remote locations on other connected computers at other sites coupled to computer system 35. The modules implementing the functionality of the present invention may be stored by file storage subsystem 60.

Bus subsystem 54 provides a mechanism for letting the various components and subsystems of computer system 35 communicate with each other as intended. The various subsystems and components of computer system 35 need not be at the same physical location but may be distributed at various locations within a distributed network. Although bus subsystem 54 is shown schematically as a single bus, alternate embodiments of the bus subsystem may utilize multiple busses.

Computer system 35 itself can be of varying types including a personal computer, a portable computer, a workstation, a computer terminal, a network computer, a control system in a wavefront measurement system or laser surgical system, a mainframe, or any other data processing system. Due to the ever-changing nature of computers and networks, the description of computer system 35 depicted in FIG. 2 is intended only as an example for purposes of illustrating one embodiment of the present invention. Many other configurations of computer system 35 are possible having more or less components than the computer system depicted in FIG. 2.

Figure 3:
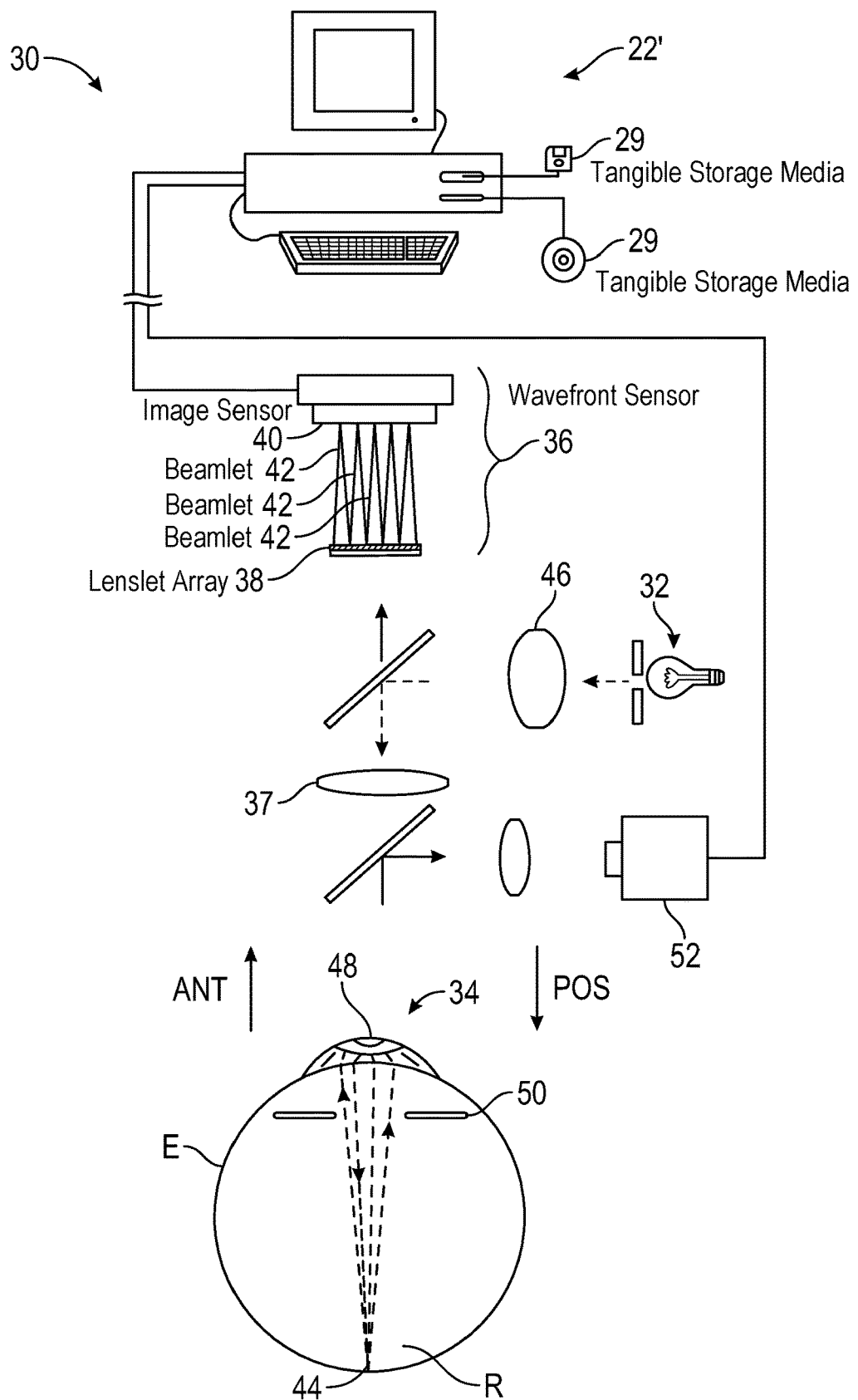
FIGS. 3 and 4 illustrate other wavefront measurement systems for use in the system of FIG. 1.

Referring now to FIG. 3, one embodiment of a wavefront measurement system 30 is schematically illustrated in simplified form. In very general terms, wavefront measurement system 30 is configured to sense local slopes of a gradient map exiting the patient's eye. Devices based on the Hartmann-Shack principle generally include a lenslet array to sample the gradient map uniformly over an aperture, which is typically the exit pupil of the eye. Thereafter, the local slopes of the gradient map are analyzed so as to reconstruct the wavefront surface or map.

More specifically, one wavefront measurement system 30 includes an image source 32, such as a laser, which projects a source image through optical tissues 34 of eye E so as to form an image 44 upon a surface of retina R. The image from retina R is transmitted by the optical system of the eye (e.g., optical tissues 34) and imaged onto a wavefront sensor 36 by system optics 37. The wavefront sensor 36 communicates signals to a process 22' for measurement of the optical errors in the optical tissues 34 and/or determination of an optical tissue ablation treatment program. Process 22' may be incorporated in the overall computer system 35, and may optionally make use of the same or similar hardware as the processor 22 and/or 52 illustrated in FIGS. 1, 1A and 2. Processor 22' may be in communication with processor 22 that directs the laser surgery system 10, or some or all of the components of computer system 35 of the wavefront measurement system 30 and laser surgery system 10 may be combined or separate. If desired, data from wavefront sensor 36 may be transmitted to a laser processor 22 via tangible media 29, via an I/O port, via an networking connection 66 such as an intranet or the Internet, or the like.

Wavefront sensor 36 generally comprises a lenslet array 38 and an image sensor 40. As the image from retina R is transmitted through optical tissues 34 and imaged onto a surface of image sensor 40 and an image of the eye pupil P is similarly imaged onto a surface of lenslet array 38, the lenslet array separates the transmitted image into an array of beamlets 42, and (in combination with other optical components of the system) images the separated beamlets on the surface of sensor 40. Sensor 40 typically comprises a charged couple device or "CCD," and senses the characteristics of these individual beamlets, which can be used to determine the characteristics of an associated region of optical tissues 34. In particular, where image 44 comprises a point or small spot of light, a location of the transmitted spot as imaged by a beamlet can directly indicate a local gradient of the associated region of optical tissue.

Eye E generally defines an anterior orientation ANT and a posterior orientation POS. Image source 32 generally projects an image in a posterior orientation through optical tissues 34 onto retina R as indicated in FIG. 3. Optical tissues 34 again transmit image 44 from the retina anteriorly toward wavefront sensor 36. Image 44 actually formed on retina R may be distorted by any imperfections in the eye's optical system when the image source is originally transmitted by optical tissues 34. Optionally, image source projection optics 46 may be configured or adapted to decrease any distortion of image 44.

In some embodiments, image source optics 46 may decrease lower order optical errors by compensating for spherical and/or cylindrical errors of optical tissues 34. Higher order optical errors of the optical tissues may also be compensated through the use of an adaptive optic element, such as a deformable mirror (described below). Use of an image source 32 selected to define a point or small spot at image 44 upon retina R may facilitate the analysis of the data provided by wavefront sensor 36. Distortion of image 44 may be limited by transmitting a source image through a central region 48 of optical tissues 34 which is smaller than a pupil 50, as the central portion of the pupil may be less prone to optical errors than the peripheral portion. Regardless of the particular image source structure, it will be generally be beneficial to have a well-defined and accurately formed image 44 on retina R.

In one embodiment, the wavefront data may be stored in computer readable medium 29 or a memory of the wavefront sensor system 30 in two separate arrays containing the x and y wavefront gradient values obtained from image spot analysis of the Hartmann-Shack sensor images, plus the x and y pupil center offsets from the nominal center of the Hartmann-Shack lenslet array, as measured by the pupil camera 51 (FIG. 3) image. Such information may be sufficient to reconstruct the wavefront or any desired portion of it. The data space to store the gradient array is not large. For example, to accommodate an image of a pupil with an 8 mm diameter, an array of a 20×20 size (i.e., 400 elements) is often sufficient. As can be appreciated, in other embodiments, the wavefront data may be stored in a memory of the wavefront sensor system in a single array or multiple arrays.

While the methods of the present invention will generally be described with reference to sensing of an image 44, a series of wavefront sensor data readings may be taken. For example, a time series of wavefront data readings may help to provide a more accurate overall determination of the ocular tissue aberrations. As the ocular tissues can vary in shape over a period of time, a plurality of temporally separated wavefront sensor measurements can avoid relying on a single snapshot of the optical characteristics as the basis for a refractive correcting procedure. Still further alternatives are also available, including taking wavefront sensor data of the eye with the eye in differing configurations, positions, and/or orientations. For example, a patient will often help maintain alignment of the eye with wavefront measurement system 30 by focusing on a fixation target. By varying a position of the fixation target as described in that reference, optical characteristics of the eye may be determined while the eye accommodates or adapts to image a field of view at a varying distance.

The location of the optical axis of the eye may be verified by reference to the data provided from a pupil camera 52. In the exemplary embodiment, a pupil camera 52 images pupil 50 so as to determine a position of the pupil for registration of the wavefront sensor data relative to the optical tissues.

Figure 4:
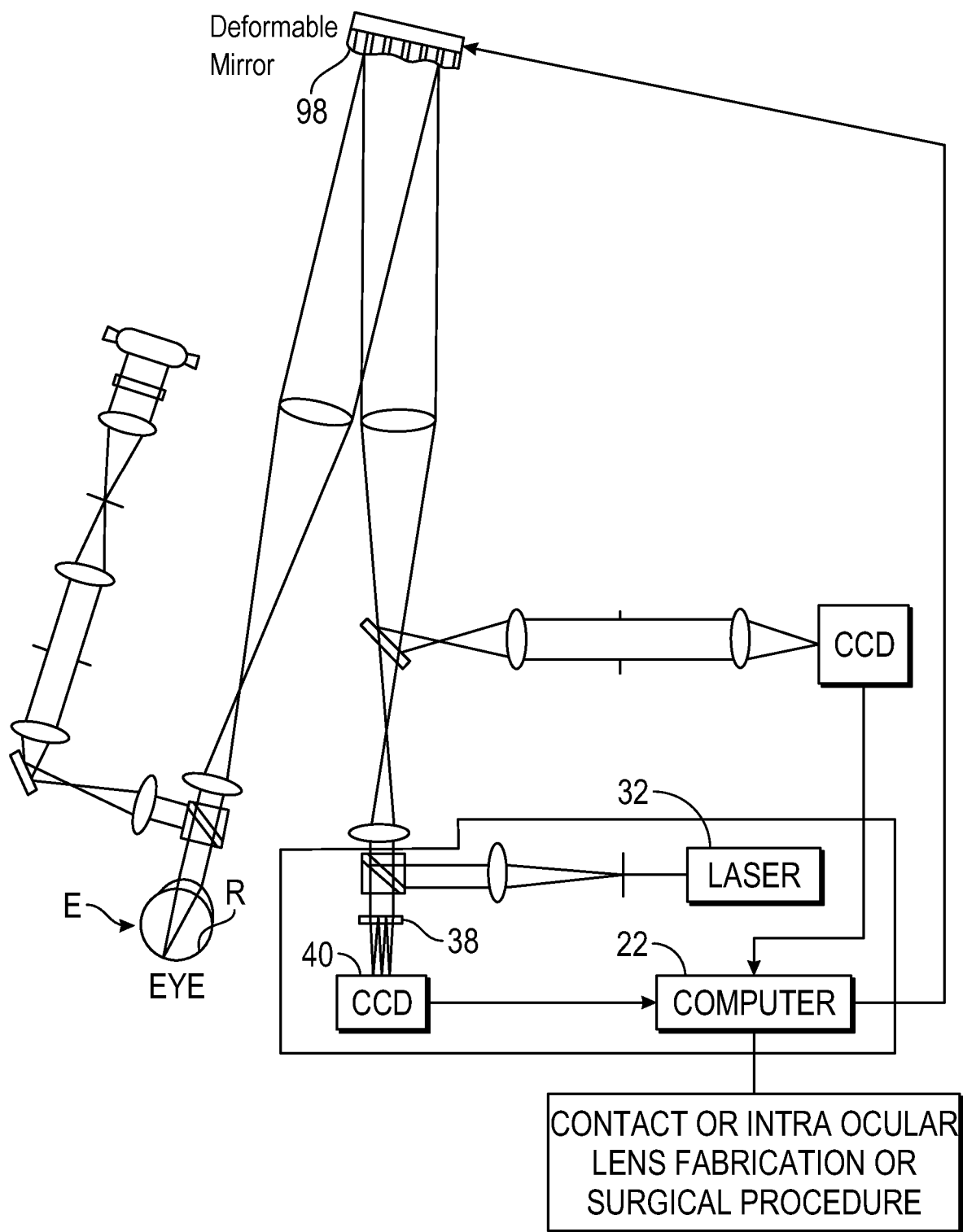

An alternative embodiment of a wavefront measurement system is illustrated in FIG. 4. The major components of the system of FIG. 4 are similar to those of FIG. 3. Additionally, FIG. 4 includes an adaptive optical element 53 in the form of a deformable mirror. The source image is reflected from deformable mirror 98 during transmission to retina R, and the deformable mirror is also along the optical path used to form the transmitted image between retina R and imaging sensor 40. Deformable mirror 98 can be controllably deformed by processor 22 to limit distortion of the image formed on the retina or of subsequent images formed of the images formed on the retina, and may enhance the accuracy of the resultant wavefront data. The structure and use of the system of FIG. 4 are more fully described in U.S. Pat. No. 6,095,651, the full disclosure of which is incorporated herein by reference.

The components of an embodiment of a wavefront measurement system for measuring the eye and ablations may comprise elements of a WaveScan system, available from ABBOTT MEDICAL OPTICS of California. It is appreciated that other wavefront aberrometers could be employed with the present invention. Relatedly, embodiments of the present invention encompass the implementation of any of a variety of optical instruments provided by WaveFront Sciences, Inc., including the COAS wavefront aberrometer, the ClearWave contact lens aberrometer, the CrystalWave IOL aberrometer, the iDesign System, and the like.

Figure 5A:
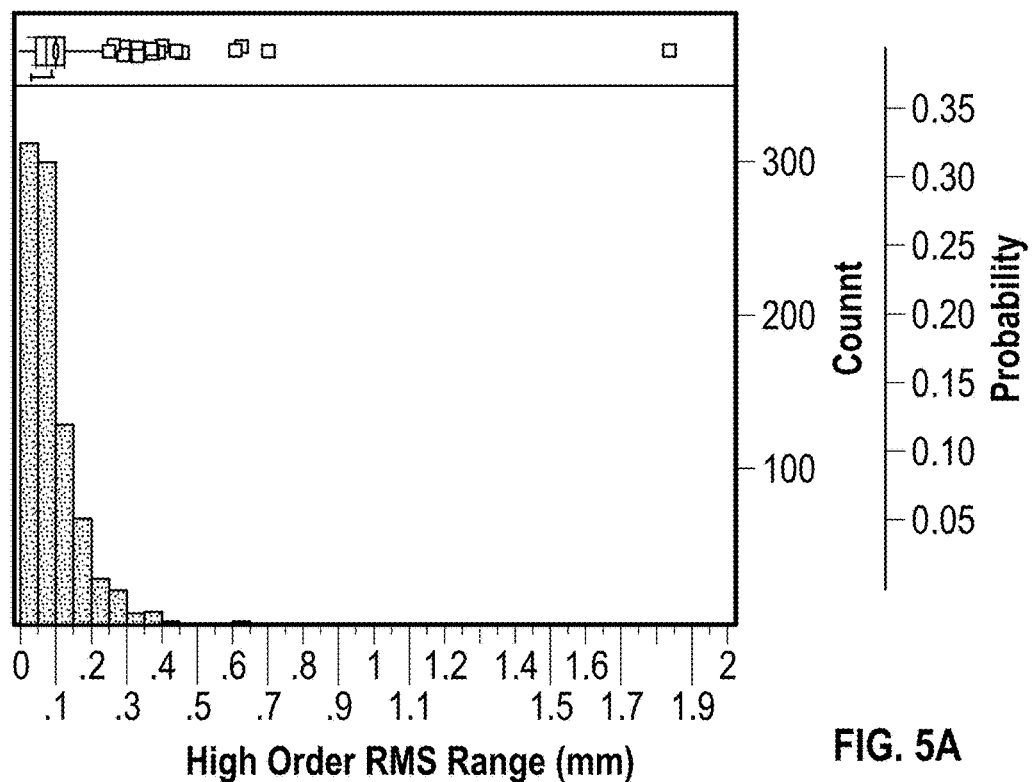
FIGS. 5A and 5B graphically illustrate a statistical range of pre-treatment high-order aberration (HOA) measurements, showing an accuracy of these measurements.
Figure 5B:
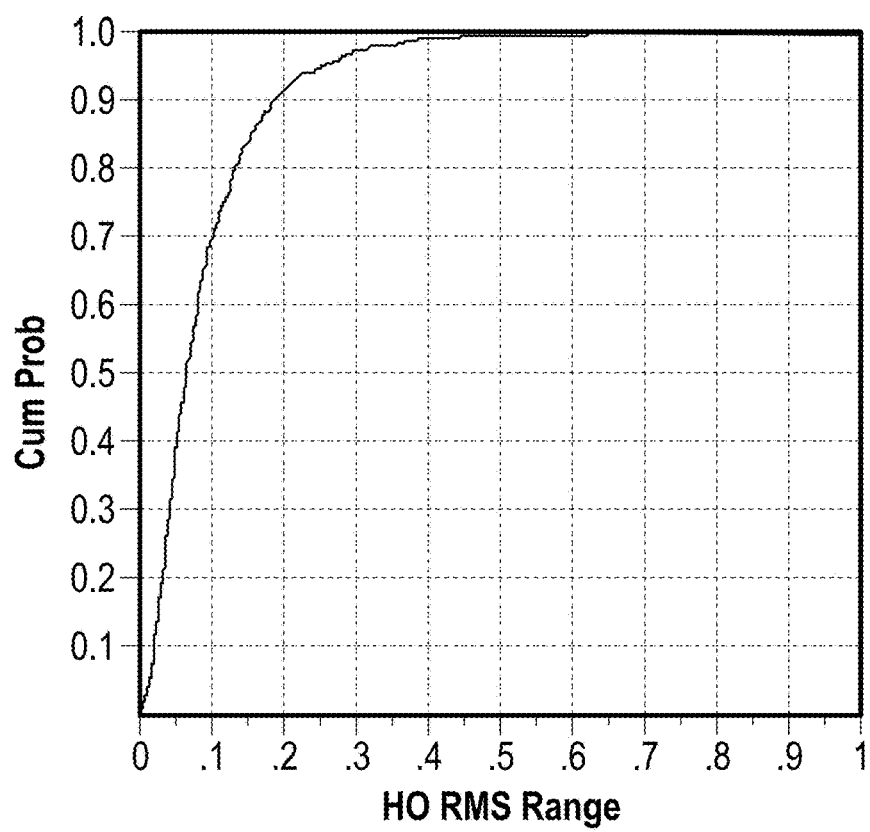

Referring now to FIGS. 5A and 5B, known laser eye surgical system treatments have not always been as effective at reducing or eliminating high-order optical aberrations of the eye as has been expected. The accuracy with which high-order optical aberrations can be measured may ultimately determine the precision with which treatment plans may be derived. Fortunately, known wavefront aberration systems are capable of measurement of the human eye with quite good accuracy. FIG. 5A shows a count and probability plot (along the vertical axis) for differing high-order root mean square (RMS) ranges for pre-treatment measurements of eyes in a series of studies. The mean range of pre-treatment measurements was about 93 microns. As illustrated by the cumulative distribution function plot of FIG. 5B, this relatively low measurement error was fairly consistent throughout the several hundred eyes of the studies. Hence, if overall treatment accuracy were limited solely by measurement accuracy, treatment should be very effective at decreasing or eliminating high-order aberrations.

To more fully analyze the interaction between eye measurements, planned treatments, the treatment that is actually performed on the eye, and the subsequent effects of healing (including epithelial regrowth, recovering from fluid-induced swelling or hydration effects, and the like), it is beneficial to measure a total effective treatment that has been rendered to an eye. The effective treatment may be defined as follows:

Treatment=Post Op−Pre Op in which Treatment here refers to a vector characterizing an effective treatment or change in refractive properties (including high-order aberrations), in which "Post Op" refers to a high-order vector characterization (typically including a wavefront measurement) after the refractive treatment to an eye and after the eye has been allowed to stabilize, and in which "Pre Op" refers to a high-order vector characterization (typically including a measurement of the wavefront) before refractive treatment of the eye.

Ideally, the Treatment should not correlate to the Pre Op measurement, as there will ideally be zero Post Op aberration. Unfortunately, known laser eye surgery measurement and treatment systems have not uniformly provided this ideal outcome.

Figure 6A:
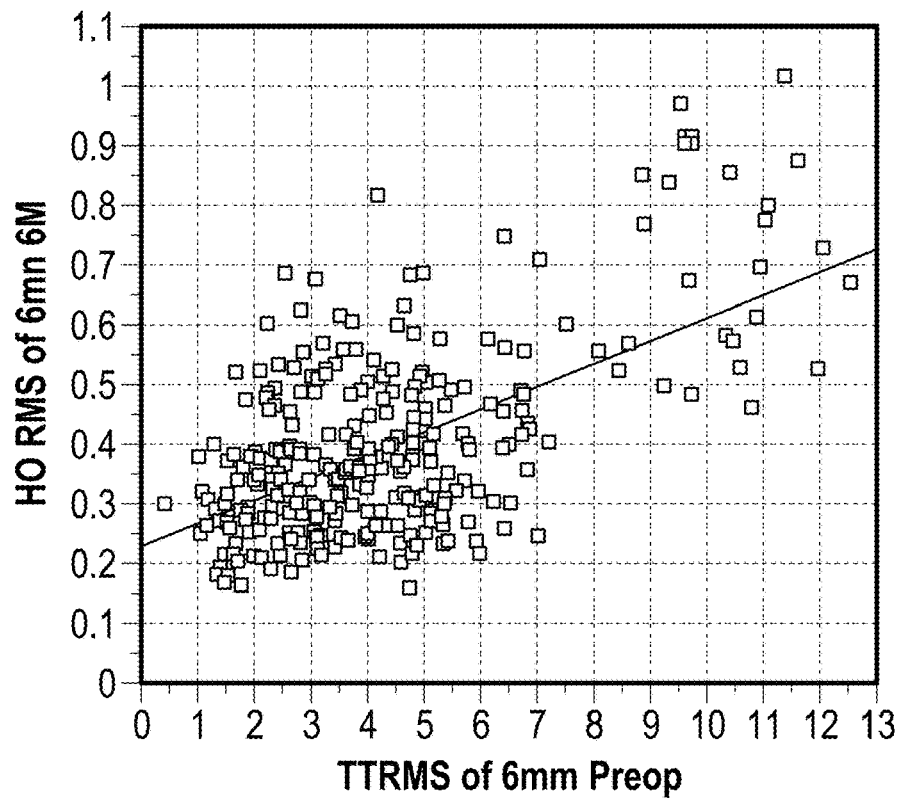
FIG. 6A illustrates a data plot of post-treatment high-order aberrations versus total pre-treatment aberrations.

Referring now to FIG. 6A, a plot of post-treatment high-order optical aberrations (along the vertical axis) against total measured pre-treatment aberrations (along the horizontal axis) for each of a plurality of previously treated eyes shows a significant correlation. Since the total aberration is dominated by the standard low-order refraction terms, there appears to be a significant undesirable coupling between the refraction or low-order aberration terms of eyes before treatment and high-order aberrations of the eyes after treatment. Note that the data FIG. 6A shows data from eyes that were measured before treatment using wavefront measurement systems such as those described above. The eyes were then treated using refractive laser eye surgery systems, with customized refractions being derived for each eye based on the measured aberrations (including both standard refractive errors and high-order aberrations) for that eye. Post-treatment measurements of the eye were performed a significant amount of time (such as 6 months) after the treatments so that healing is largely completed and the refractive properties of the eye have substantially stabilized.

Figure 6B:
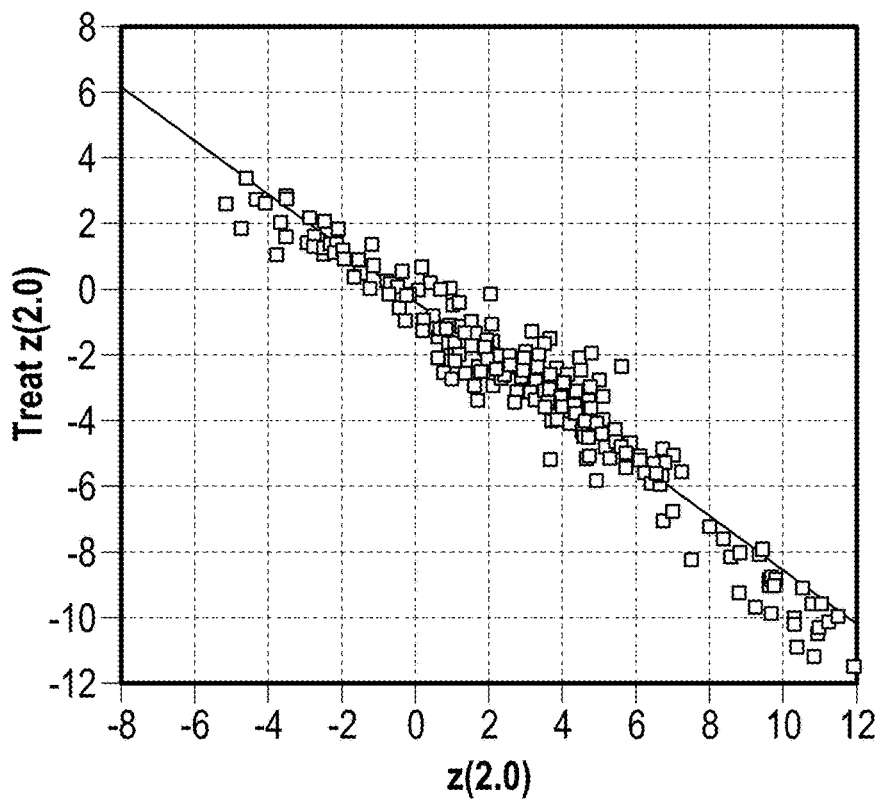
FIG. 6B is a data plot showing a strong correlation between an effective spherical defocus treatment and a pre-treatment measured spherical defocus, indicating effective treatment of low-order errors.

Referring now to FIG. 6B, existing laser eye surgery systems do a quite good job at correcting standard refractive errors. Individual components of the eye aberrations may be referenced using their standard Zernike coefficient numbers, as seen in the table below. The defocus term Z (2,0) of the effective treatment is plotted along the vertical axis, and the same coefficient for the Pre Op eye is plotted along the horizontal axis. A slope near −1 indicates that for each unit of defocus of the eye before treatment, the effective treatment substantially removed that same amount of error from the eye. Hence per this data, existing laser eye surgical systems (including their associated measurement systems) can do a good job in correcting standard refractive errors of the eye.

TABLE

| j = index | n = order | m = frequency | $Z_a^{\ -}(\rho, \theta)$ |
|---|---|---|---|
| 0 | 0 | 0 | 1 |
| 1 | 1 | −1 | $2\rho \sin\theta$ |
| 2 | 1 | 1 | $2\rho \cos\theta$ |
| 3 | 2 | −2 | $\sqrt{6}\,\rho^2 \sin 2\theta$ |
| 4 | 2 | 0 | $\sqrt{3}\,(2\rho^2 - 1)$ |
| 5 | 2 | 2 | $\sqrt{6}\,\rho^2 \cos 2\theta$ |
| 6 | 3 | −3 | $\sqrt{8}\,\rho^3 \sin 3\theta$ |
| 7 | 3 | −1 | $\sqrt{8}\,(3\rho^3 - 2\rho)\sin\theta$ |
| 8 | 3 | 1 | $\sqrt{8}\,(3\rho^3 - 2\rho)\cos\theta$ |
| 9 | 3 | 3 | $\sqrt{8}\,\rho^3 \cos 3\theta$ |
| 10 | 4 | −4 | $\sqrt{10}\,\rho^4 \sin 4\theta$ |
| 11 | 4 | −2 | $\sqrt{10}\,(4\rho^4 - 3\rho^2)\sin 2\theta$ |
| 12 | 4 | 0 | $\sqrt{5}\,(6\rho^4 - 6\rho^2 + 1)$ |
| 13 | 4 | 2 | $\sqrt{10}\,(4\rho^4 - 3\rho^2)\cos 2\theta$ |
| 14 | 4 | 4 | $\sqrt{10}\,\rho^4 \cos 4\theta$ |
| 15 | 5 | −5 | $\sqrt{12}\,\rho^5 \sin 5\theta$ |
| 16 | 5 | −3 | $\sqrt{12}\,(5\rho^5 - 4\rho^3)\sin 3\theta$ |
| 17 | 5 | −1 | $\sqrt{12}\,(10\rho^5 - 12\rho^3 + 3\rho)\sin\theta$ |
| 18 | 5 | 1 | $\sqrt{12}\,(10\rho^5 - 12\rho^3 + 3\rho)\cos\theta$ |
| 19 | 5 | 3 | $\sqrt{12}\,(5\rho^5 - 4\rho^3)\cos 3\theta$ |
| 20 | 5 | 5 | $\sqrt{12}\,\rho^5 \cos 5\theta$ |
| 21 | 6 | −6 | $\sqrt{14}\,\rho^6 \sin 6\theta$ |
| 22 | 6 | −4 | $\sqrt{14}\,(6\rho^6 - 5\rho^4)\sin 4\theta$ |
| 23 | 6 | −2 | $\sqrt{14}\,(15\rho^6 - 20\rho^4 - 6\rho^2)\sin 2\theta$ |
| 24 | 6 | 0 | $\sqrt{7}\,(20\rho^6 - 30\rho^4 + 12\rho^2 - 1)$ |
| 25 | 6 | 2 | $\sqrt{14}\,(15\rho^6 - 20\rho^4 + 6\rho^2)\cos 2\theta$ |
| 26 | 6 | 4 | $\sqrt{14}\,(6\rho^6 - 5\rho^4)\cos 4\theta$ |
| 27 | 6 | 6 | $\sqrt{14}\,\rho^6 \cos 6\theta$ |
| 28 | 7 | −7 | $4\rho^7 \sin 7\theta$ |
| 29 | 7 | −5 | $4\,(7\rho^7 - 6\rho^5)\sin 5\theta$ |
| 30 | 7 | −3 | $4\,(21\rho^7 - 30\rho^5 + 10\rho^3)\sin 3\theta$ |
| 31 | 7 | −1 | $4\,(35\rho^7 - 60\rho^5 + 30\rho^3 - 4\rho)\sin\theta$ |
| 32 | 7 | 1 | $4\,(35\rho^7 - 60\rho^5 + 30\rho^3 - 4\rho)\cos\theta$ |
| 33 | 7 | 3 | $4\,(21\rho^7 - 30\rho^5 + 10\rho^3)\cos 3\theta$ |
| 34 | 7 | 5 | $4\,(7\rho^7 - 6\rho^5)\cos 5\theta$ |
| 35 | 7 | 7 | $4\rho^7 \cos 7\theta$ |

Figure 7A:
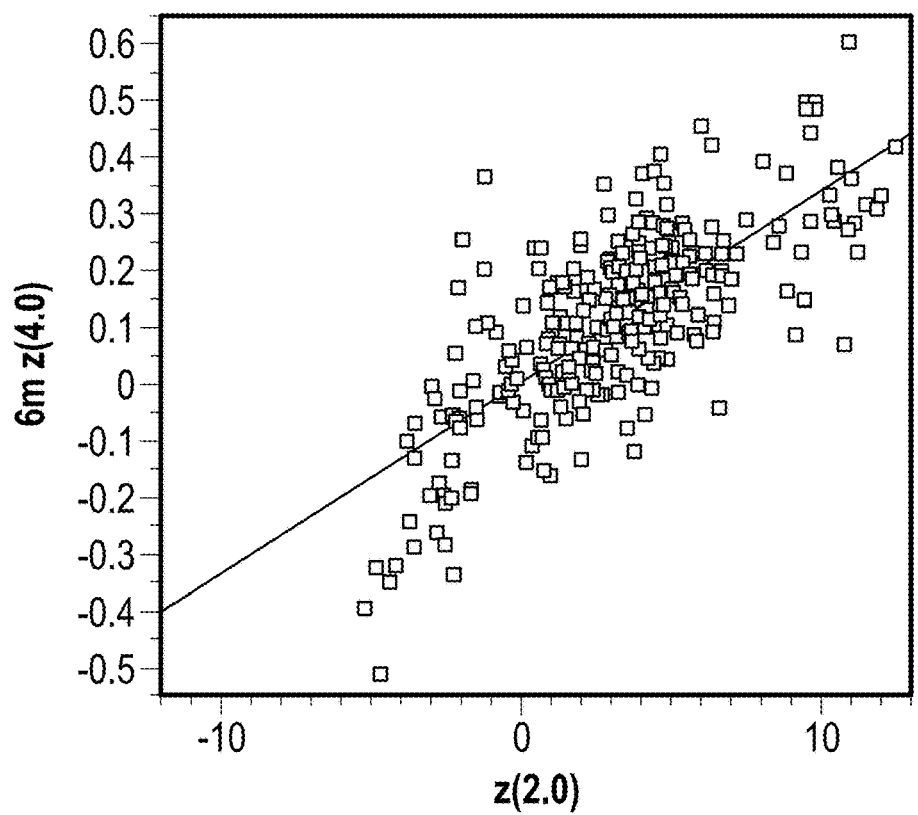
FIGS. 7A and 7B illustrate data plots analogous to FIG. 6B, but showing correlations between pre-treatment aberrations and post-treatment high-order aberrations that indicate potential inducement of some high-order aberrations.
Figure 7B:
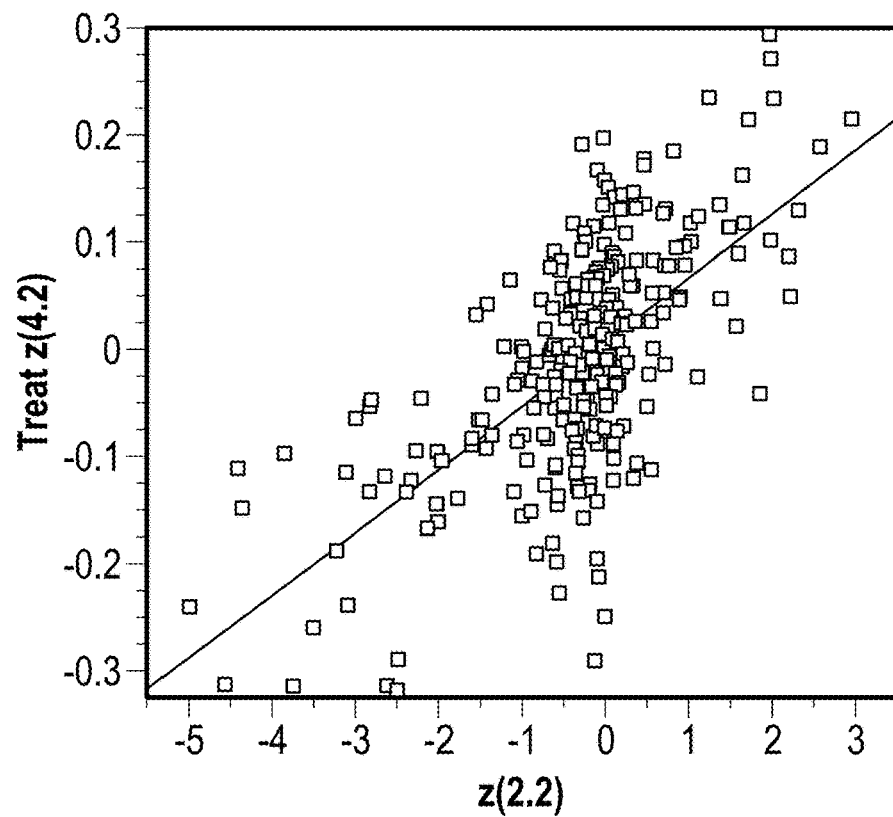

Referring to FIGS. 7A and 7B, the total response of the eyes to the measurement and treatment may be more complex when individual high-order aberrations are analyzed. For example, as illustrated in FIG. 7A, a measured Post Op aberration in the Z (4,0) term (plotted on the vertical axis) has a positive correlation relative to measured pre-treatment defocus on Z (2,0) (plotted o the horizontal axis). In other words, the positive slope of the graph of FIG. 7A indicates the Z (4,0) high-order spherical aberration term may be induced in proportion to the amount of defocus that is being corrected. This discrete relationship may optionally be used to develop a specific adjustment or nomogram for future eyes, thereby seeking to avoid inducing such errors. Unfortunately, the total number of such correlations between high-order aberrations are sufficiently complex that seeking to adjust the treatments using such discrete nomograms for each identified correlation may be both challenging and, in the end, less than ideally effective. For example, as illustrated in FIG. 7B, a significant pre-treatment error in the Z (2,2) high-order aberration term may be coupled to a significant treatment Z (4,2) term. Given enough of these discrete correlations, a nomogram adjustment approach may end up resolving some errors while inducing others, particularly where knowledge regarding all of the discrete couplings is less than perfect.

Figure 8A:
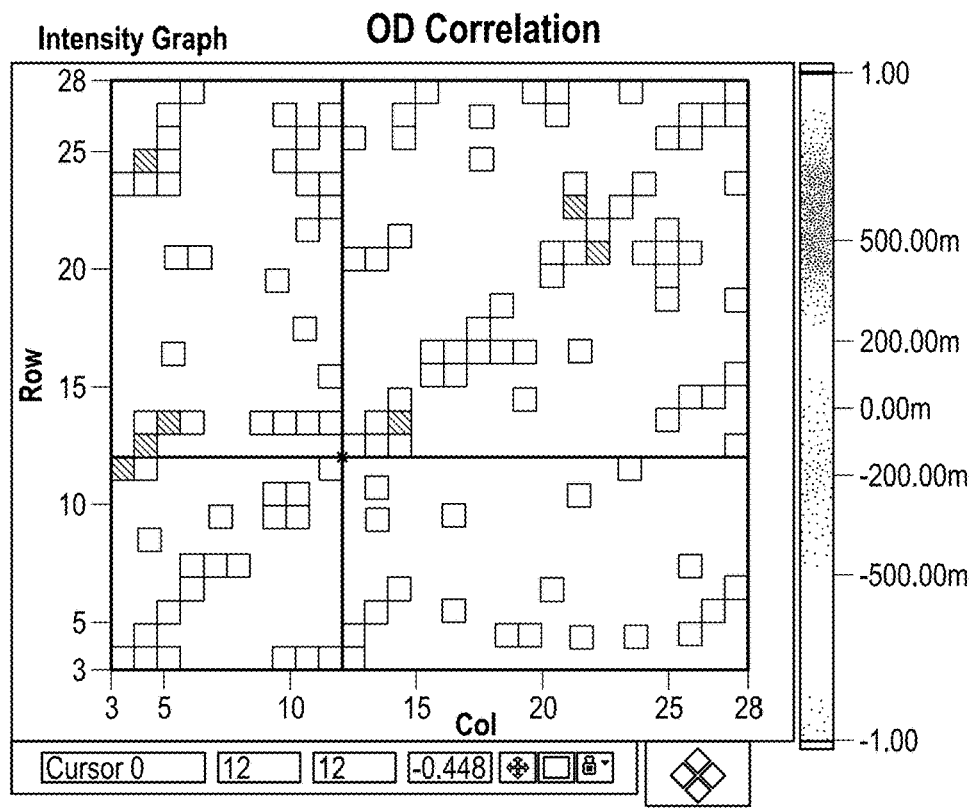
FIGS. 8A and 8B graphically illustrate correlations between effective treatment high-order aberrations and measured pre-treatment high-order aberrations for the right eye and left eye, respectively.
Figure 8B:
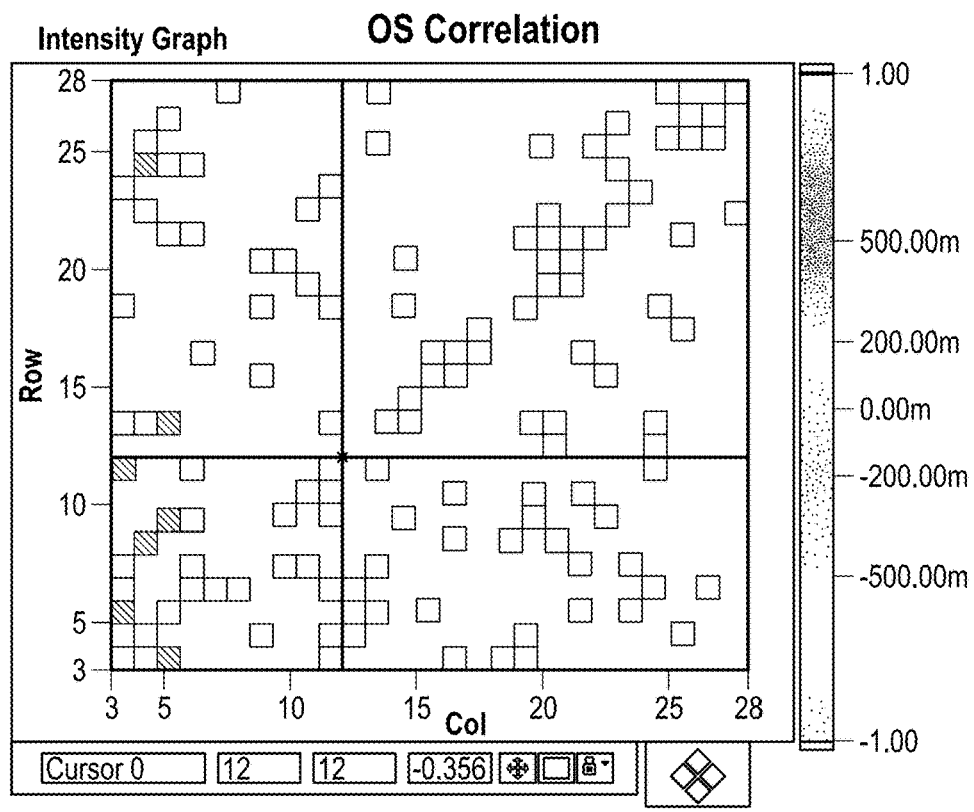
Figure 8C:
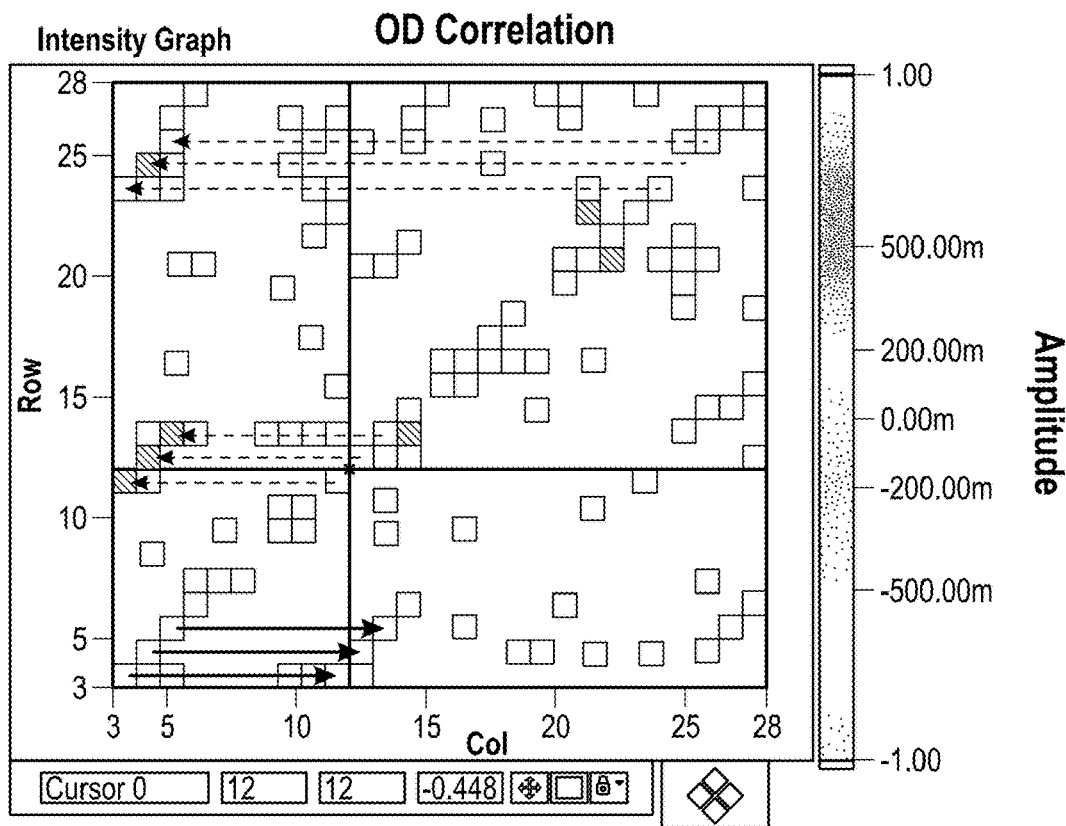
FIG. 8C identifies a few selected exemplary couplings between induced high-order aberrations and pre-treatment measured high-order aberrations.

Referring now to FIGS. 8A and B, a graphical representation of a correlation matrix between the treatment and pre-op wavefront measurements indicates the large number and intensities of correlations between differing Zernike globally Zernike—Zernike terms. Each axis number illustrated in FIGS. 8A and 8B corresponds to a specific Zernike coefficient, starting with Z(−2,2) (Zernike #3) through Z(6, 6). If planned treatments altered the target aberrations in the amounts desired (and imposed no other induced aberrations, i.e., had no couplings to other aberration modes), the values along the diagonal extending from 3,3 to 28,28 would all be negative 1, and all values other than those along the diagonal would be 0. As indicated in FIGS. 8A and 8C, existing measurement and treatment systems do not provide this idealized result. Instead, there are significant correlations for many of the Zernike terms between the effective treatment and the pre-treatment aberration measurements off the diagonal.

The correlations between pre-operative measurements and effective treatment coefficients are relatively high for the refractive term numbers 3 through 5. Unfortunately, many of the diagonal elements are significantly different than the ideal 1 value, and many of the off-diagonal elements are significantly different than the ideal 0 value. Note that differences in sign and values of the correlations may be associated with the different eyes, with the right eye having significantly different values then the left eye. For example, horizontal aberration terms for Zernike 7 and 8 are different.

Referring now to FIG. 8C, selected terms have been highlighted with relatively low angular or even radial coefficients. Specifically, pre-operative measurement identifying defocus (Zernike #4) induces spherical aberration (Zernike #12) in the treatment, as indicated by the sign of the correlation. Similarly, second order astigmatism is induced in the effective treatment when correcting for measured pre-operative astigmatism. Some crossover coupling between the astigmatism terms is also evident (between Zernike #3 and Zernike #5) within the second radial order. These may be among the most significant terms of the couplings matrix, because the refraction terms are generally the far largest measured pre-operative aberrations in an eye. Nonetheless, most or even all other off-diagonal elements will contribute to aberrations (in other words, inducing at least some aberrations after treatment) at some (typically lesser) level. Some of the more important couplings identified in the correlation matrix are graphically illustrated in FIG. 9.

Figure 10:
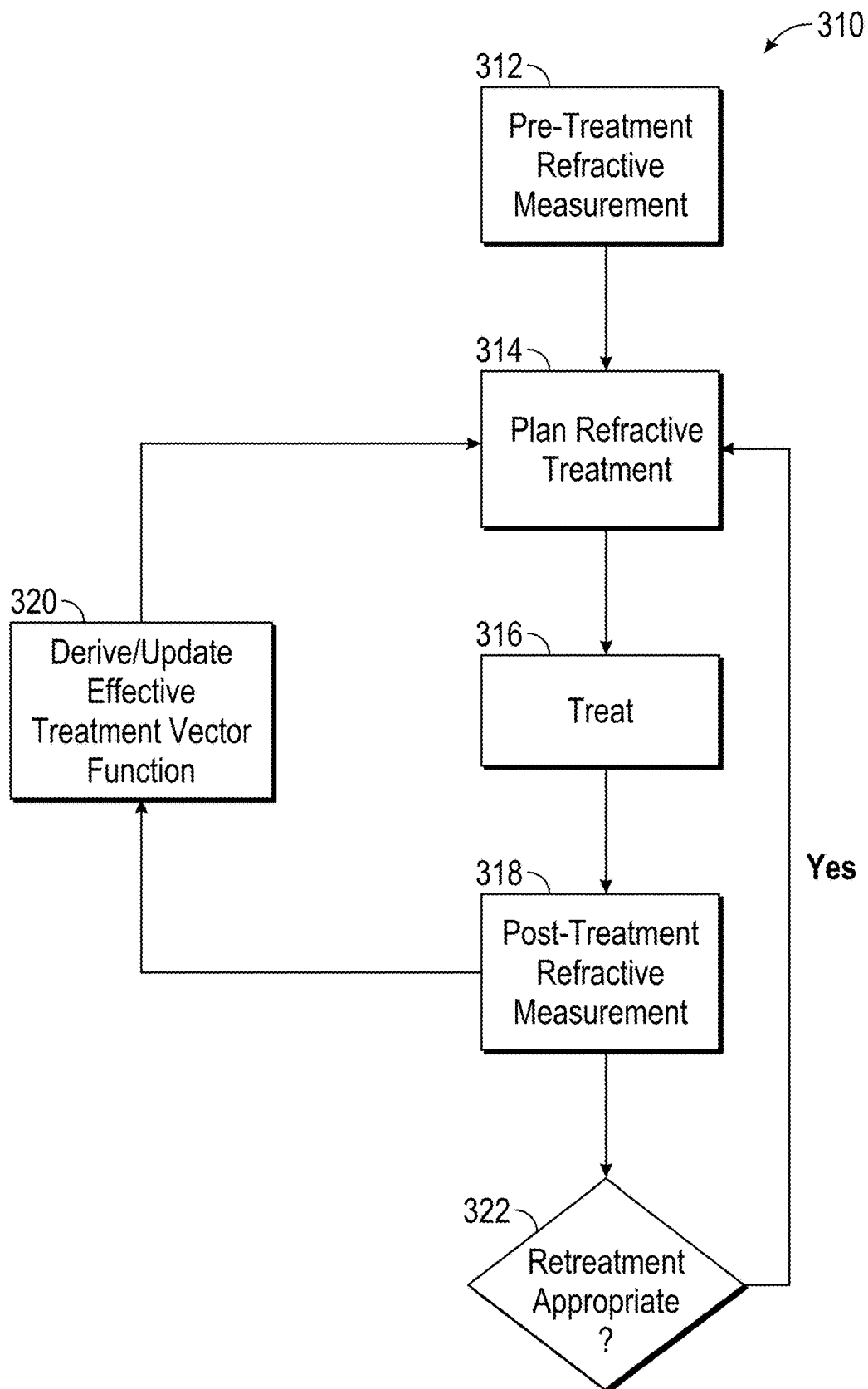
FIGS. 10 and 10A are functional block diagrams schematically illustrating processing components and methods for eye treatments, including relationships between measurement and treatment parameters.

Referring now to FIG. 10, an overview of an improved treatment and treatment improvement methodology 310 begins for a particular patient with a pre-treatment refractive measurement 312. A refractive treatment plan is developed 314, and the patient is treated 316 so as to correct refractive defects identified in the measurement 312. After treatment, a post-treatment refractive measurement of the treated eye is taken 318.

Post-treatment measurement 318 has at least 2 distinct advantages. First, it verifies that the intended refractive change has been imposed on the patient's eye, thereby giving information regarding that specific patient. In addition, the post-treatment measurement 318 provides feedback information which can be used for development of refractive treatment plans 314 for treatment of other eyes in the future. In exemplary embodiments of the methods described herein, the feedback from prior treatments is affected by deriving and/or updating an effective treatment vector function 320.

Regarding the use of post-treatment measurements 318 for the treated patient, these measurements may provide an indication whether retreatment is appropriate 322. For example, if the post-treatment measurement differs from an expected characterization of the eye by more than a threshold amount, retreatment of the eye (such as a new repeated LASIK treatment or the like) may be planned 314 and then implemented 316. Target refractive measurements and associated variation thresholds may be established for one or more specific time intervals after treatment 316. For example, an immediate post-treatment refractive measurement 318 on the day of treatment 316 may have one expected set of refractive properties and range of acceptable variations, while a two-week or six-month follow up post-treatment refractive measurement 318 may each have differing values. Hence, post-treatment measurement 318 may comprise a series of measurements. The retreatment decision 322 may also occur repeatedly over the days, weeks, months, or even years after treatment 316.

Figure 9:
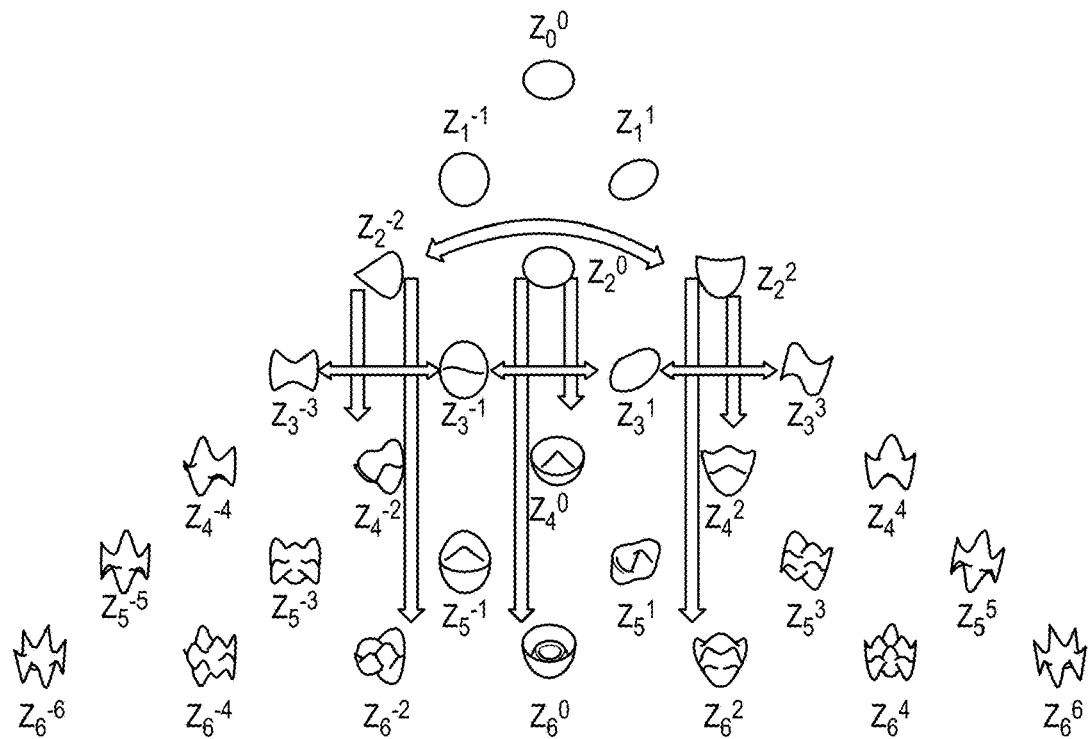
FIG. 9 schematically illustrates selected couplings.

More detailed understanding of the information displayed in FIGS. 8A through 9 can be obtained through defining and more rigorously analyzing some of the terms. A Surgically-Induced Refractive Correction (SIRC) may be defined as the actual change in measured wavefront induced by the surgery. The vector SIRC may thus be defined mathematically as follows:

SIRC=Post Op−Pre Op

The vector elements may here include a described number of Zernike coefficients. Another vector, the Intended Refractive Correction (IRC) is the change in refractive properties that is the goal of the treatment. When the intended outcome of the treatment is an emmetropic eye, we may calculate IRC as being effectively equal to the negative of the pre-treatment aberration measurement Pre Op vector as follows:

IRC=Pre Op

Note that emmetropia is not necessarily the goal of many treatments. For example, it may be desirable to leave (or even induce) a small amount of myopia in one eye of a patient while the other eye is rendered emmetropic so as to provide sufficient monovision for mitigation of presbyopia. Alternatively, a variety of multifocal or aspherical presbyopic shapes may be desirable in the eyes of patients who have or will lose some or all of their ability to accommodate. When emmetropia is not the goal, we can calculate the IRC vector based on the measured pre-treatment aberrations and a vector characterizing the final resultant desired shape of the eye, Target, as follows:

IRC=Pre Op+Target

To provide the desired outcomes, it is beneficial for SIRC to approach or be equal to IRC, within physical optic limitations and clinical tolerances.

Applying our vector definitions to the overall treatment plan 310, pre-treatment refractive measurement 312 will generally result in definition of a Pre Op vector characterizing high-order aberrations of a particular patient's eye prior to receiving any treatment. Planning of the refractive treatment 314 defines the IRC intended refractive correction vector, with the IRC reflecting the Target vector when emmetropia is not the goal. Alternatively, when emmetropia is the goal, the target can be defined as an emmetropic target vector.

After treatment 316, post-treatment refractive measurements 318 provide, for each previously treated eye, a Post Op vector characterizing high-order aberrations of the eye. For each prior treatment, a surgically induced refractive correction SIRC can be defined as the difference between the Post Op vector and the Pre Op vector for that associated eye. The set of SIRC vectors can then be used to derive an effective treatment vector function 320. Where the effective treatment vector function 320 has previously been defined, new eye treatments (and their associated pre- and post-treatment measurements) can be used to update the effective treatment vector function. Hence, the effective treatment vector function 320 provides a feedback loop for planning refractive treatments 314 of new patients based on prior measurements and treatments of a number of eyes.

Figure 10A:
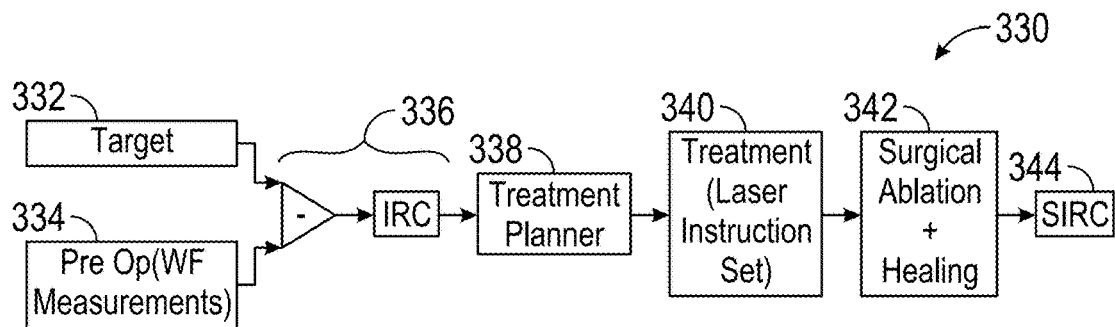

Referring now to FIG. 10A, a simplified block diagram schematically illustrates the input and output vector relationships for a particular patient, and also schematically provides a description of software modules associated with the vector elements described above. A target module 332 defines a Target vector or desired high-order characterization of the eye after treatment. Note that target module 332 may allow a physician and/or patient to select from a variety or range of target treatments. For example, a relatively young patient who seeks the best possible distance vision may desire emmetropia in both eyes, while patients of sufficient age to exhibit presbyopia may select a desired amount of myopia in one eye or an aspherical or multifocal refractive shape so as to provide a desired level of near vision for reading or the like. A Pre Op input module 334 accepts the wavefront or other measurements which characterize the high-order refractive properties of the eye. Hence, the Pre Op measurement input 334 will often be coupled to a wavefront aberrometer, topographer, and/or the like. An intended refractive correction IRC vector module 336 will calculate and store the intended refractive correction vector. Like the Target module 332 and Pre Op measurement module 334, IRC module 336 will typically be implemented via software and/or hardware of computer system 35 (see FIG. 1).

Continuing on with the simplified functional block diagram 330 of FIG. 10A, a treatment planning module 338 will derive a set of instructions corresponding to the Treatment vector for the refractive laser or other treatment structure to be used, and the Treatment instruction 340 will be stored for use. The Treatment instructions will typically include shot locations and numbers in a table, and the table will often be ordered so as to minimize thermal damage, expedite the speed of the procedure, and the like. Surgical ablation will be performed using a laser control module 342 (generally including many of the components described above regarding processor 22 of FIGS. 1 and 1A). The surgical ablation itself, along with post-treatment healing, will alter the final shape of the eye. Post-treatment measurements, together with the pre-treatment measurements can then be used to define the overall effective treatment SIRC in a surgically induced refractive correction treatment module 344.

Treatment planner 338 will often use basis data defining ablation depths for the target laser fluence(s) and spot size(s). This basis data will often have been measured on porcine and/or cadaver eyes, and use of this data may be tightly controlled by regulatory agencies such as the Food and Drug Administration. Note that the basis data need not exactly match ablation rates in in-vivo human eyes. For example, no healing may be included during measurement of the basis data. Nonetheless, the basis data can form an important foundation of regulatory approval for LASIK and other refractive correction procedures, particularly for previously approved refractive laser treatment systems. Advantageously, the basis data need not be altered so as to take advantage of the feedback methodology and systems improvements described herein.

An improved functional block diagram 350 and associated method include many of the components described above regarding FIG. 10A. However, rather than directly making use of the IRC vector, adjustments to the IRC are implemented so as to define an adjusted intended refractive correction vector AIRC for storage in an adjusted correction module 352.

A variety of discrete and/or systemic adjustments can be made to the IRC. For example, physicians using existing refractive laser treatment systems have experience at inputting physician adjustments into a physician adjustment module 354 based on their experiences, practices, and the like. Similarly, a number of nomogram adjustments are input 356 so as to alter treatments based on qualitative or quantitative factors for a specific patient. These inputs effectively close the loop between clinical outcomes and desired corrections to a particular patient's eye for certain aspects of the treatment, but do not necessarily comprehensively alter the treatment, particularly where couplings between alterations in one mode of high-order optical aberrations errors is intertwined with a number of potentially induced high-order optical aberrations in the treated eye. Still further adjustments to the IRC may also be incorporated, including adjusting of the planned treatment so as to compensate for reduced ablation depths at increasing angles of laser incidence upon the corneal tissue surface. The so-called cosine corrections and other adjustments (including chromatic adjustments) may be included in a chromatic and cosine correction module 358. Additionally, adjustments may be allowed based on still other factors. For example, measurements of manifest refraction or low-order aberrations may be input into a pre-treatment K input module 368.

Figure 10B:
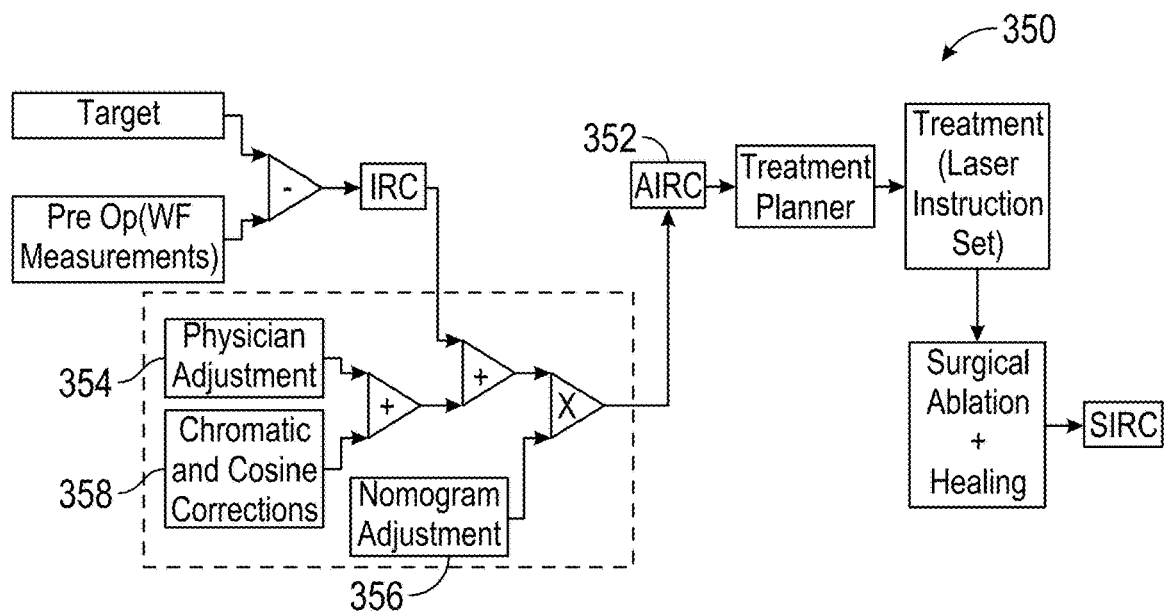
FIG. 10B is an improved functional block diagram schematically illustrating development of treatment plan parameters for improving clinical outcomes.
Figure 10C:
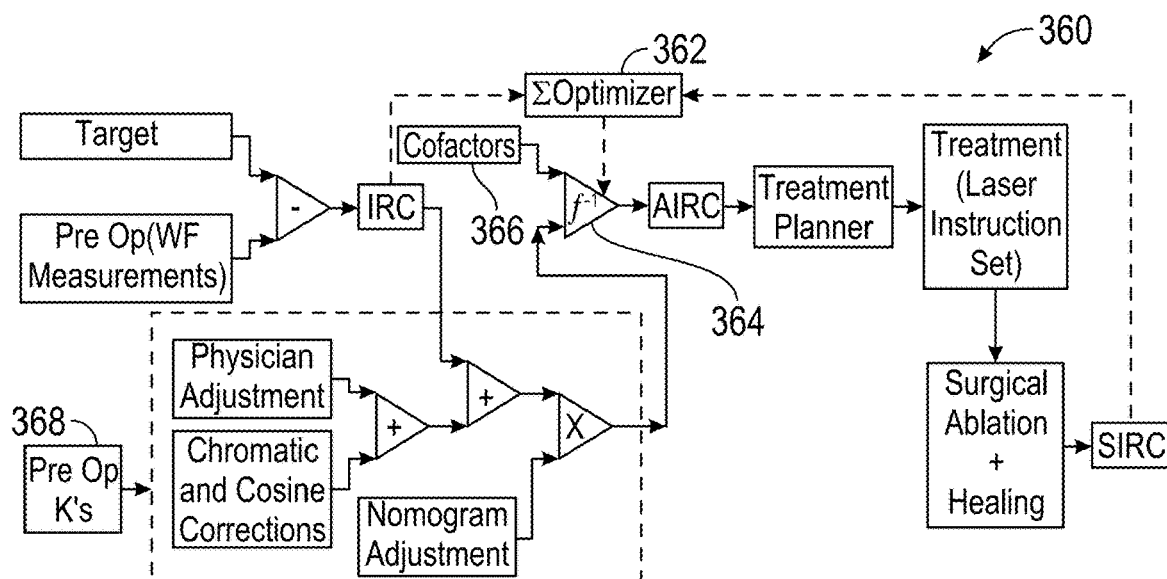
FIG. 10C is an improved functional block diagram illustrating an exemplary treatment plan solution to iteratively improve outcomes for successive patients by adjusting the treatment based on the effective treatments generated from prior treatments so as to mitigate induced high-order aberrations of the eye.

To more robustly make use of feedback from prior treatments, the functional block diagram 360 of FIG. 10C provides a more general solution that will improve outcomes, ideally via intermittent, regular, or continuous process improvements. Many of the method steps and associated modules are similar to those described above. However, the relationship between IRC and AIRC may be substantially more sophisticated. More specifically, rather than merely adjusting the low-order aberrations between the IRC and AIRC, the methodology of FIG. 10C will result in significant changes to the higher-order aberrations of the treatment to be performed. Improvements in the treatment may be performed by feeding back results of prior treatments via SIRC data from high-order aberration measurements into an effective treatment vector function deriving module 362 so as to generate an effective treatment vector function or adjustment function $f^{-1}$ 364. Note that the physician retains the ability to adjust treatments on an individual basis as described above regarding FIG. 10B. As generally described above, the effective treatment vector function $f^{-1}$ may also make use of co-factors (such as patient age, gender, race, measurement and/or treatment humidity, measurement and/or treatment physician identify, measurement and/or treatment system model number or identity, and the like). A co-factor module 366 may be used to input these co-factors into the processor module running the effective Treatment vector function 364.

Determination of the appropriate effective treatment vector function module 362 may optionally be described as an optimization. Note that the derivation of the appropriate function need not be an absolute optimization, but that the resulting vector function will preferably alter the IRC vector so as to result in significantly better vision after treatment and healing than would be provided without adjustment.

A number of mathematical approaches may be applied by module 362 to derive an appropriate adjustment vector function $f^{-1}$ and an associated function $f$. In the example below, a relatively simple linear algebra and multivarient regression approach are applied for deriving an influence matrix defining $f$. Note that more complex non-linear approaches could also be used.

As described above, the SIRC and IRC are expressed as vectors containing components with values that represent surgically-induced and intended refractive correction wavefront surfaces. SIRC vector also incorporates the Pre Op wavefront measurement surfaces prior to treatment in this exemplary embodiment. The vector elements may include Zernike coefficients that best describe the SIRC and IRC wavefront aberrations. The SIRC and IRC vectors may further contain keratometry values. Optional components of these vectors may include co-factor parameters that are known or suspected of influencing the SIRC, such as age, gender, humidity, water content of the cornea, and the like. The total number of components in each of these vectors may be designated as N.

It is generally desired to predict the SIRC produced by the system given an IRC. Toward this end, it can be assumed that the SIRC and IRC vectors are related through an influence matrix $f$ and an error vector E as follows:

$$\vec{E} = \overrightarrow{SIRC} - \bar{f} \cdot \overrightarrow{IRC}$$

Advantageously, this mathematical model allows each component in the IRC to potentially contribute to every component in the SIRC, in the exemplary embodiment, in a linear fashion;

$$E_i = SIRC_i - \sum_j f_{ij} IRC_j$$

The components of $f$ may be identified or fit by taking clinical measurements of the SIRC and IRC optical aberration components as described above. Assuming there are m pairs of measurements of SIRC and IRC, each designated by the subscript k, a global merit function $\psi$ may be defined as follows:

$$\psi = \sum_{i,k} e_{ik}^2 = \sum_{i,k} \left( SIRC_{ik} - \sum_j f_{ij} IRC_{jk} \right)^2$$

In the merit function $\psi$, each unknown component of $f$ has an associated designation $f_{ij}$. We may minimize $\psi$ with respect to each unknown component of $f$ by generating $m^2$ equations, one for each unknown (provided m is greater than or equal to n). For example:

$$\frac{\partial \psi}{\partial f_{lm}} = 0 = 2 \sum_{i,k} \left( SIRC_{ik} - \sum_j f_{ij} IRC_{jk} \right) \left( -\sum_j \frac{\partial f_{ij}}{\partial f_{lm}} IRC_{jk} \right)$$

$$0 = \sum_{i,k} \left( SIRC_{ik} - \sum_j f_{ij} IRC_{jk} \right) \left( \sum_j \delta_{il} \delta_{jm} IRC_{jk} \right)$$

$$0 = \sum_k \left( SIRC_{lk} - \sum_j f_{lj} IRC_{jk} \right) (IRC_{mk})$$

$$\sum_k SIRC_{lk} IRC_{mk} = \sum_j f_{lj} \sum_k IRC_{jk} IRC_{mk}$$

The solution for $f$ can be obtained through linear algebra as follows. The resultant set of $M^2$ equations can be written in more succinct matrix form and solved as follows:

$$\sum_k SIRC_{lk} IRC_{mk} = \sum_j f_{lj} \sum_k IRC_{jk} IRC_{mk}$$

$$\overline{A} = \overline{f} \cdot \overline{B}$$

where A and B are matrices with components $$A_{lm} = \sum_k SIRC_{lk} IRC_{mk}$$

$$B_{jm} = \sum_k IRC_{jk} IRC_{mk}$$

hence we may solve for $\bar{f}$ $$\bar{f} = \overline{A} \cdot \overline{B}^{-1}$$

provided the inverse of $\overline{B}$ exists.
Finally, $$\bar{f}^{-1} = \overline{A} \cdot \overline{B}^{-1}$$

Having determined a best fit value for $f$, that matrix can be used to evaluate the quality of the model and generate the AIRC as follows:

$$\vec{E} = \overrightarrow{SIRC} - f \cdot \overrightarrow{IRC}$$

In the above, E represents an error vector for $f$. The basic model evaluation can be applied to additional paired measurements to validate our solution for $f$. The quality of the model can be evaluated by evaluating E for each additional measurement, and by comparing it to the desired physical optics and clinical tolerances of the overall system.

In order to adjust the IRC so as to result in the desired SIRC, we can use $f^{-1}$ so as to generate the AIRC. Hence, when input into the treatment planner, the AIRC will produce the desired treatment for the system:

$$\overrightarrow{AIRC} = \bar{f}^{-1} \cdot \overrightarrow{SIRC} = \bar{f}^{-1} \cdot \overrightarrow{IRC}.$$

The adjustment in this embodiment produces a AIRC based on a linear combination of the IRC and the co-factors.

The combination of wavefront IRC components is generally a cross-coupling which can have physical origins in a number of factors, potentially including the low spatial frequency filtering effects of the flap, the biomechanical and healing effects, tissue transition zone offsets, and the like. Co-factors may represent variables that don't directly enter into the treatment planner module 338 (see FIG. 10A), but which may still have an influence over the outcome. Exemplary co-factors are described above. Adjustments may tend to be highly specific. For example, adjustments may relate to individual physicians or clinics, or sub-populations (for example, high myopes).

Figure 11:
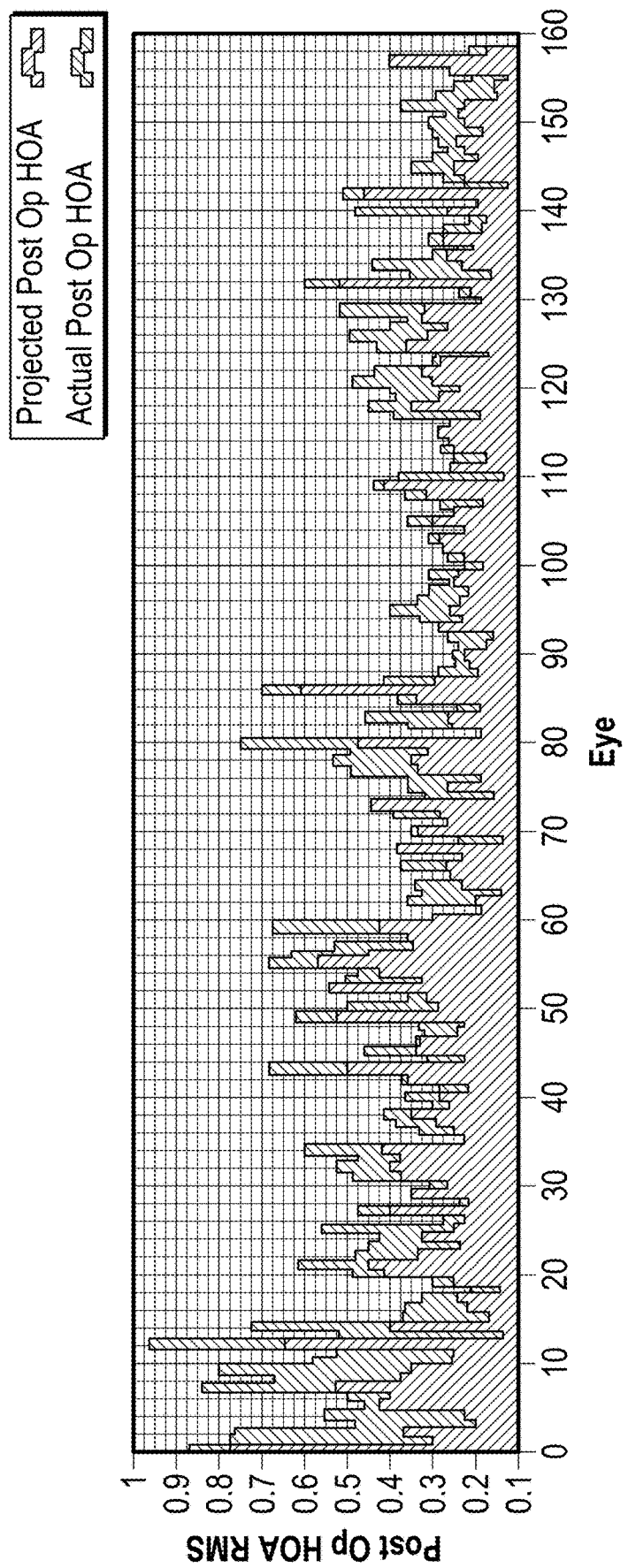
FIG. 11 graphically indicates the surprising benefits in optical accuracy that may be provided by the systems and methods described herein.

Referring now to FIG. 11, modeling based on studies of prior eye treatments indicates surprisingly significant reductions may be provided by the methods and systems described herein. Most, almost all (over 95%) and/or substantially all (over 90%) eyes are projected to exhibit a significant reduction in High-Order Aberations (HOA).

Figure 12:
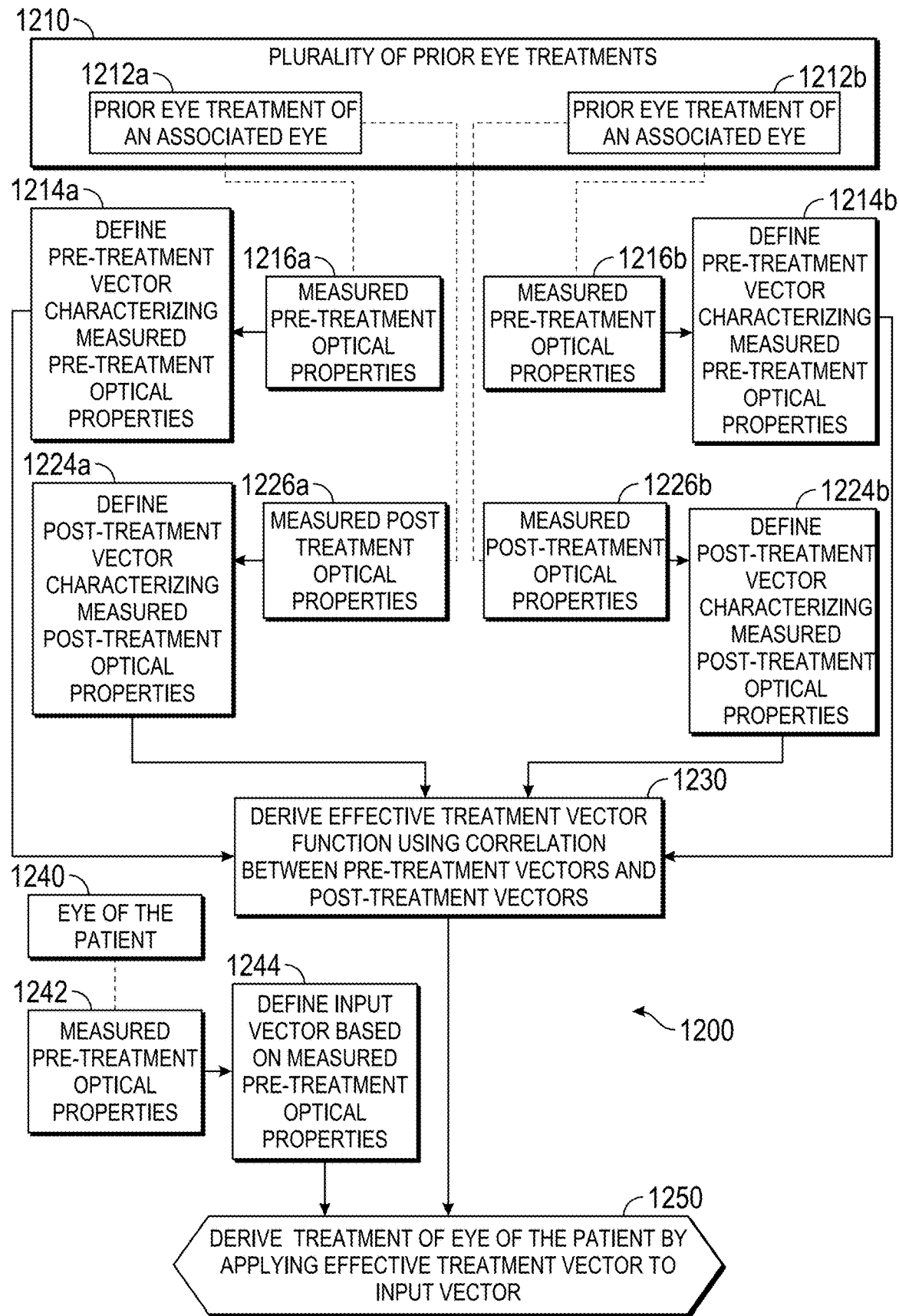
FIG. 12 depicts exemplary aspects of systems and methods according to embodiments of the present invention.

FIG. 12 depicts aspects of a method 1200 for planning a refractive treatment of an eye of a patient, according to embodiments of the present invention. As shown here, method 1200 includes determining an effective treatment vector function based on a plurality of prior eye treatments 1210. As shown here, for individual prior eye treatments of an associated eye 1212a, 1212b (of the plurality of prior eye treatments 1210), exemplary methods involve defining a pre-treatment vector, as depicted by steps 1214a, 1214b, characterizing measured pre-treatment optical properties of the associated eye 1216a, 1216b, respectively. Relatedly, for individual prior eye treatments of an associated eye 1212a, 1212b (of the plurality of prior eye treatments 1210), exemplary methods involve defining a post-treatment vector, as depicted by steps 1224a, 1224b, characterizing measured post-treatment optical properties of the associated eye 1226a, 1226b, respectively. Further, for the plurality of prior eye treatments 1210, the method includes deriving an effective treatment vector function using a correlation between the pre-treatment vectors and the post-treatment vectors, as indicated by step 1230. Method 1200 also includes defining an input vector based on measured pre-treatment optical properties 1242 of the eye of the patient 1240, as depicted by step 1244. Further, method 1200 includes deriving a treatment of the eye of the patient by applying the effective treatment vector function to the input vector, as depicted by step 1250. In some instances, a pre-treatment vector, a post-treatment vector, an effective treatment vector, and/or an input vector can characterize a refraction, a non-refractive cofactor characterizing the patient and/or the treatment setting, and/or optical properties of the eyes.

In some instances, a measured pre-treatment optical property (e.g. 1216a, 1216b, and/or 1242) may include a low order aberration, a high order aberration, a corneal topography measurement, an optical coherence tomography measurement, a corneal keratometry value, or the like. In some instances, a refractive treatment as derived in step 1250 may be for an excimer laser treatment, a femtosecond laser treatment, an intraocular lens treatment, a contact lens treatment, or a spectacle treatment. In some cases, methods further include administering the treatment to the eye of the patient.

In some instances, prior eye treatments 1212a, 1212b, may correspond to a first patient and a second patient, respectively. In some cases, prior eye treatments 1212a, 1212b may correspond to a right eye (OD) and a left eye (OS), respectively. As such, right eyes (or groups of right eyes) and left eyes (or groups of left eyes) can be analyzed separately. Relatedly, data for right eyes (or groups of right eyes) and left eyes (or groups of left eyes) can be transformed to be analyzed simultaneously. In some instances, prior eye treatments 1212a, 1212b may correspond to right eyes only, or alternatively, to left eyes only. Hence, an effective treatment vector function can be derived from on multiple treatments (or information therefrom). In some cases, each prior eye treatment of a plurality of prior eye treatments corresponds to a separate individual. In some cases, each prior eye treatment of a plurality of prior eye treatments corresponds to a previously treated right eye. In some cases, each prior eye treatment of a plurality of prior eye treatments corresponds to a previously treated left eye. Relatedly, when evaluating the eye of the patient 1240, the selected eye (e.g. OD or OS) can correspond to the analyzed eyes from which the effective treatment vector function is derived (e.g. OD or OS). Similarly, the derived treatment can also correspond to the appropriate eye of the patient (e.g. OD or OS).

Figure 13:
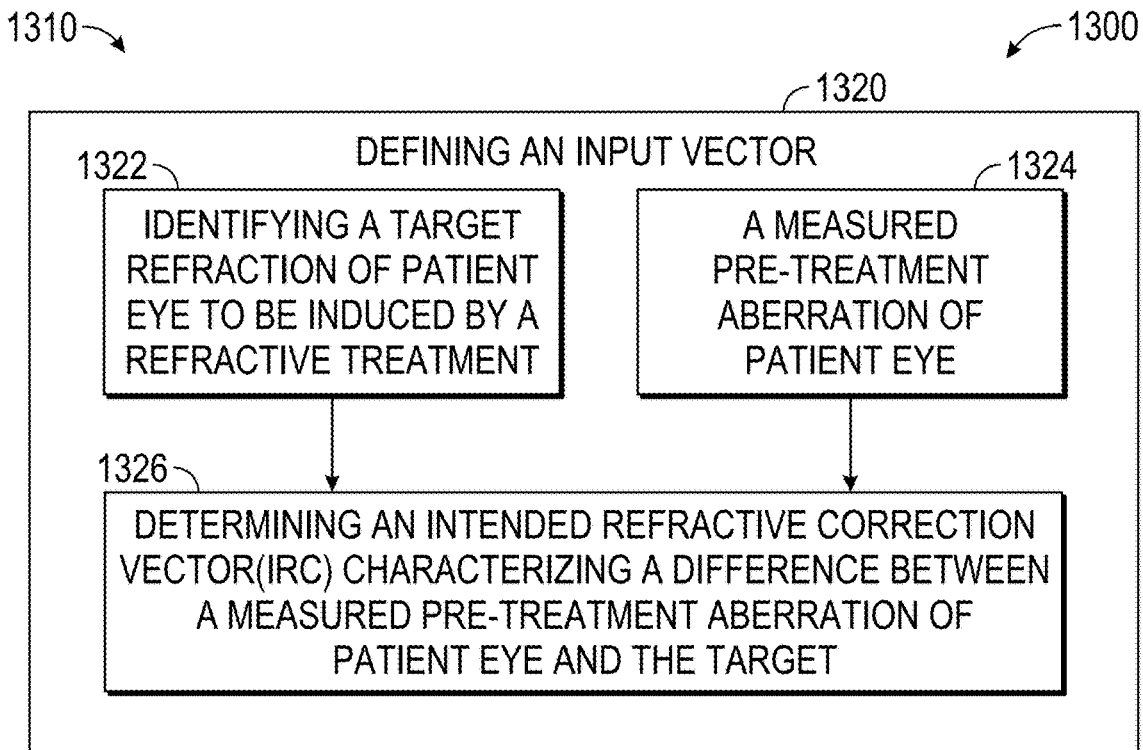
FIG. 13 depicts exemplary aspects of systems and methods according to embodiments of the present invention.
Figure 13:
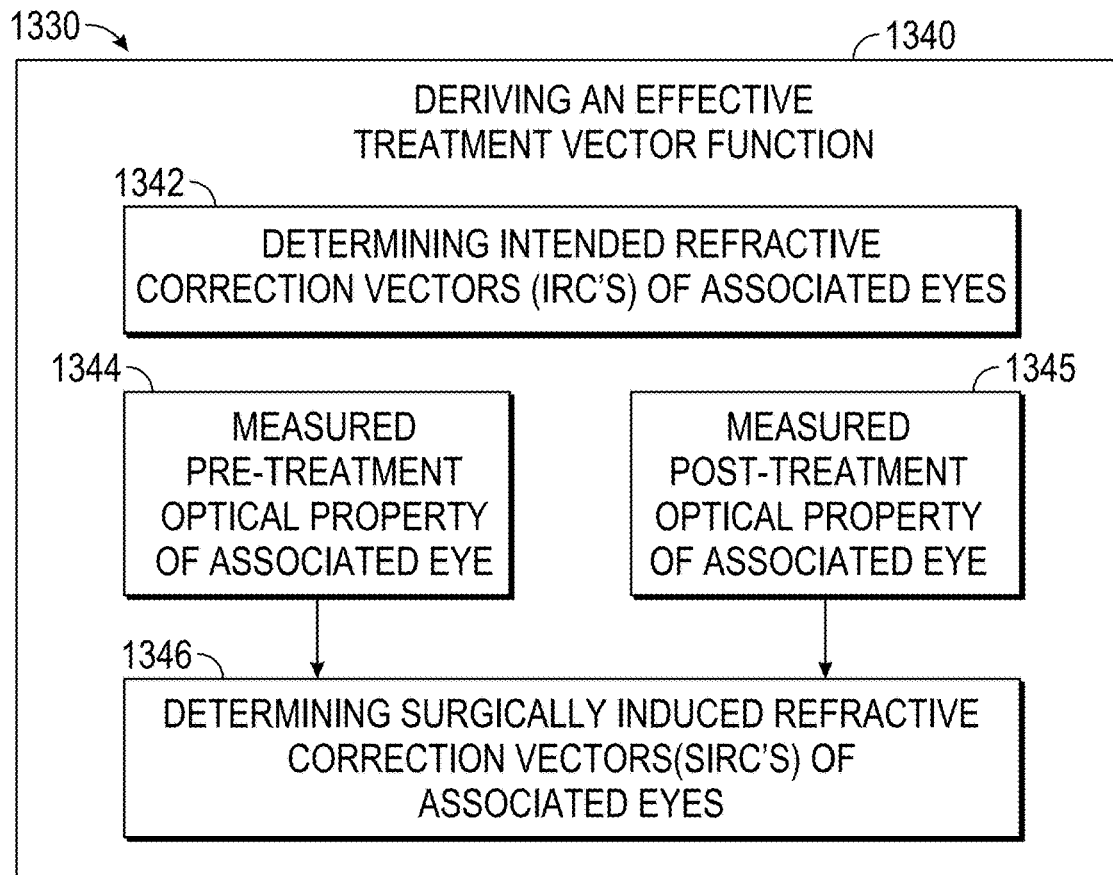

FIG. 13 depicts additional aspects of a process 1310 for defining an input vector 1320, as well as a process 1330 for deriving the effective treatment vector function 1340. As shown here, a procedure for defining an input vector may include identifying a target refraction of the eye of the patient to be induced by the refractive treatment, as indicated by step 1322, and determining an intended refractive correction vector (IRC) characterizing a difference between a measured pre-treatment optical property 1324 of the eye of the patient and the target, as indicated by step 1326. Further, as shown here, a procedure 1330 for deriving the effective treatment vector function from prior treatments may include determining intended refractive correction vectors (IRCs) of associated eyes (e.g. of a plurality of associated eyes), as indicated by step 1342, and determining surgically induced refractive correction vectors (SIRCs) of the associated eyes, as indicated by step 1346. According to some embodiments, each SIRC can characterize a difference between measured pre-treatment optical properties 1344 and post-treatment optical properties 1345 of an associated eye. In some instances, optical properties, SIRCs, and/or IRCs can contain keratometry values, K-values, optical coherence tomography values, corneal topography values, anterior chamber length or depth values, posterior corneal curvature values, axial length values, crystalline lens thickness values, radii of curvature values, tilt values, and the like.

Figure 14:
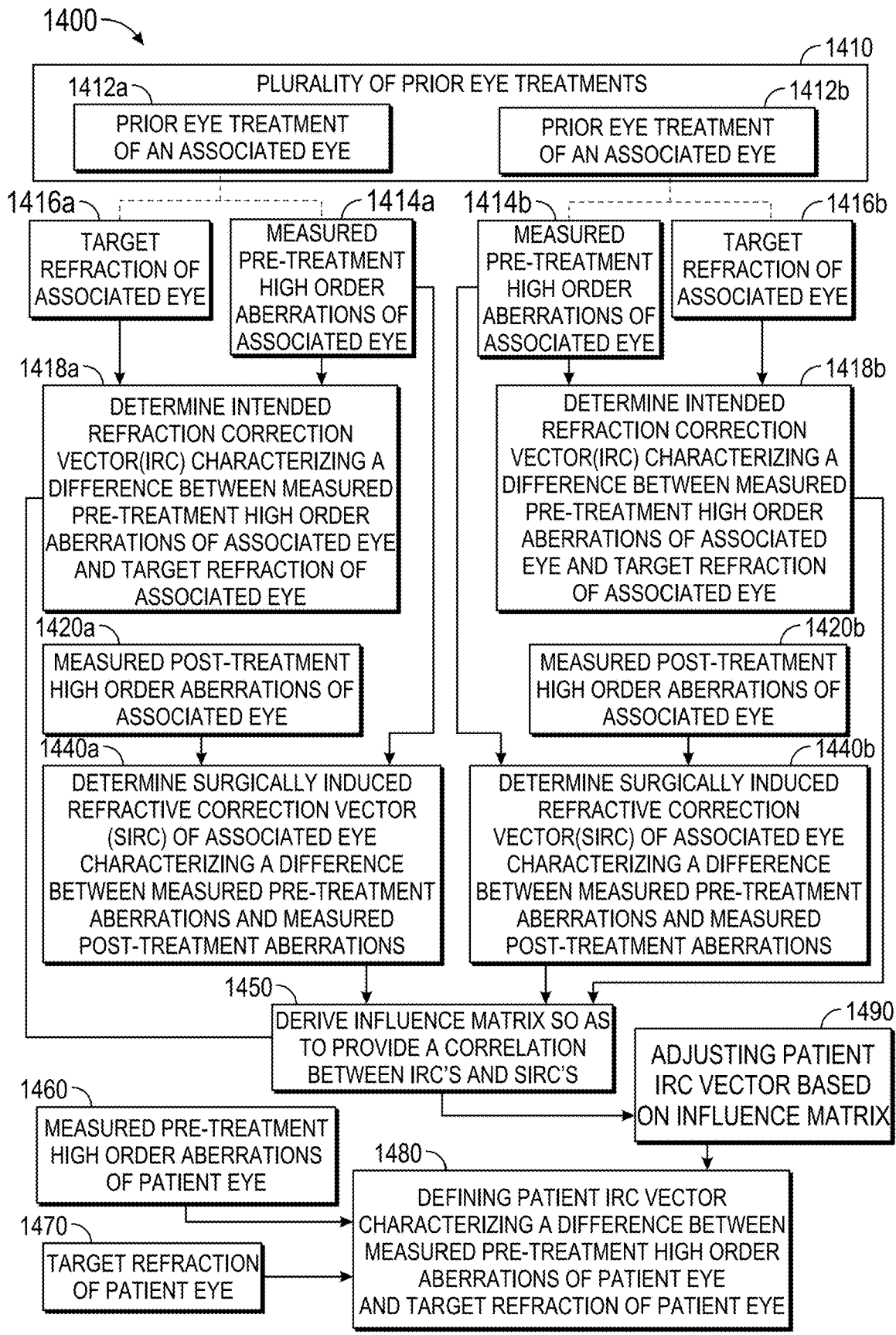
FIG. 14 depicts exemplary aspects of systems and methods according to embodiments of the present invention.

FIG. 14 depicts aspects of a method 1400 for planning a refractive treatment of an eye of a patient, according to embodiments of the present invention. As shown here, method 1400 includes deriving an influence matrix from previously treated eyes, or from a plurality of prior eye treatments 1410. For each prior eye treatment of an associated eye 1412a, 1412b, it is possible to determine an intended refractive correction vector (IRC) and a surgically induced refractive correction vector (SIRC), as follows. As shown here, the method 1400 includes determining an intended refractive correction vector (IRC) characterizing a difference between measured pre-treatment high-order aberrations (or optical properties) 1414a, 1414b of the associated eye and a target refraction of the associated eye 1416a, 1416b as indicated by steps 1418a, 1418b, respectively. Further, the method 1400 includes determining a surgically induced refractive correction vector (SIRC) of the associated eye characterizing a difference between the measured pre-treatment aberrations (or optical properties) 1414a, 1414b and measured post-treatment aberrations (or optical properties) of the associated eye 1420a, 1420b, as indicated by steps 1440a, 1440b, respectively. Methods may also include deriving an influence matrix so as to provide a correlation between the IRCs and the SIRCs, as indicated by step 1450. What is more, methods may include defining a patient IRC vector characterizing a difference between measured pre-treatment high-order aberrations (or optical properties) 1460 of the eye of the patient and a target refraction 1470 of the eye of the patient (e.g. intended surgically induced correction or outcome), as indicated by step 1480. In some cases, a target refraction 1470 may correspond to an emmetropic target. In some cases, a target refraction may correspond to a non-emmetropic target. Further, methods may include adjusting the patient IRC vector based on the influence matrix, as indicated by step 1490. In some cases, an optical property (e.g. 1414a, 1414b, 1420a, 1420b, 1460) may include a low order aberration, a high order aberration, a corneal topography measurement, an optical coherence tomography measurement, and/or a corneal keratometry value. In some cases, methods further include administering a treatment to the eye of the patient based on the patient IRC vector. In some cases, for each prior eye treatment of the associated eye, the IRC can be further determined so as to characterize a difference between measured pre-treatment low order aberrations and target low order aberrations, and so as to characterize a difference between measured pre-treatment corneal topography and target corneal topography. In some cases, for each prior eye treatment of the associated eye, the SIRC can be further determined so as to characterize a difference between the measured pre-treatment low order aberrations and measured post-treatment aberrations, and so as to characterize a difference between measured the pre-treatment corneal topography and measured post-treatment corneal topography. In some cases, a patient IRC vector can be further defined so as to characterize a difference between measured pre-treatment low order aberrations and the target refraction, and so as to characterize a difference between measured pre-treatment topography of the eye and target topography.

In some instances, prior eye treatments 1412a, 1412b, may correspond to a first patient and a second patient, respectively. In some cases, prior eye treatments 1412a, 1412b may correspond to a right eye (OD) and a left eye (OS), respectively. As such, right eyes (or groups of right eyes) and left eyes (or groups of left eyes) can be analyzed separately. Relatedly, data for right eyes (or groups of right eyes) and left eyes (or groups of left eyes) can be transformed to be analyzed simultaneously. In some instances, prior eye treatments 1412a, 1412b may correspond to right eyes only, or alternatively, to left eyes only. Hence, an influence matrix (or SIRC) can be derived from on multiple treatments (or information therefrom). In some cases, each prior eye treatment of a plurality of prior eye treatments corresponds to a separate individual. In some cases, each prior eye treatment of a plurality of prior eye treatments corresponds to a previously treated right eye. In some cases, each prior eye treatment of a plurality of prior eye treatments corresponds to a previously treated left eye. Relatedly, when evaluating the eye of the patient 1460, the selected eye (e.g. OD or OS) can correspond to the analyzed eyes from which the influence matrix (or SIRC) is derived (e.g. OD or OS). Similarly, the adjusted patient IRC vector can also correspond to the appropriate eye of the patient (e.g. OD or OS).

Figure 15:
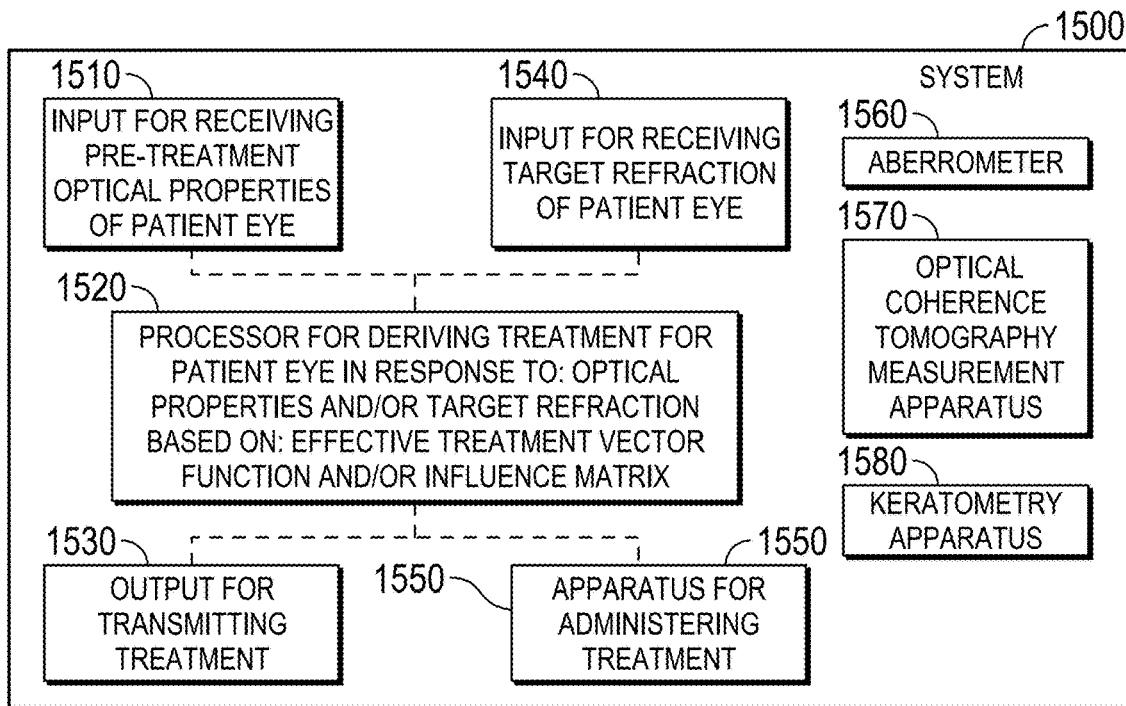
FIG. 15 depicts exemplary aspects of systems and methods according to embodiments of the present invention.

FIG. 15 depicts aspects of a system 1500 for planning or deriving a refractive treatment of an eye of a patient, according to embodiments of the present invention. As shown here, system 1500 includes an input 1510 for receiving pre-treatment optical properties of the eye of the patient, a processor 1520 coupled to the input, and an output 1530 coupled to the processor. In some instances, the processor 1520 is configured to derive the treatment of the eye of the patient in response to the optical properties of the eye of the patient, by applying an effective treatment vector function. In some cases, the effective treatment vector function can be derived from, for each of a plurality of prior eye treatments, a correlation between a pre-treatment vector characterizing optical properties of the associated eye before treatment, and a post-treatment vector characterizing post-treatment optical properties of the associated eye. In some instances, the output 1530 can be configured to transmit the treatment to facilitate improving refraction of the eye of the patient.

According to some embodiments, system 1500 may include an input 1540 for receiving a target refraction of a patient eye. In some embodiments, system 1500 may include or be coupled with an apparatus 1550, such as a laser delivery system, for administering a treatment to a patient. As shown here, system 1500 may also include, or be coupled with, an aberrometer 1560. In some cases, the aberrometer 1560 may be configured to sense low order aberrations of the eye and the high-order aberrations of an eye. Such low and high-order aberrations may be transmitted to or received by the processor 1520. In some cases, the aberrometer 1560 may be configured to sense corneal topography of the eye. Such corneal topography can be transmitted to or received by the processor 1520. System 1500 may also include, or be coupled with, an optical tomography measurement apparatus 1570. In some cases, the optical tomography measurement apparatus 1570 can be configured to detect optical properties of the eye. Such optical properties may be transmitted to or received by the processor 1520. System 1500 may also include, or be coupled with, a keratometry apparatus 1580. In some cases, the keratometry apparatus 1580 can be configured to detect optical properties of the eye. Such optical properties may be transmitted to or received by the processor 1520.

Typically, the keratometry apparatus 1580 can be used to measure or evaluate the radius of curvature of the cornea. The keratometry apparatus 1580 may be, for example, a keratometer or ophthalmometer that measures the curvature of the anterior corneal surface. In a keratometry technique, the anterior corneal surface can be considered as a specular reflector. A ring can be placed in front of the eye, and the cornea, in reflection, can form a virtual image of the ring below its surface, such that the virtual image is the first Purkinje image of the ring. The size of this image can be related to the corneal radius of curvature (R), according to the equation $R=2dy/h$, where h is the radius of the ring object, y is the radius of the ring image, and d is the distance between the object and image. Using a keratometric index of refraction, it is possible to convert the corneal radius to corneal power. In this way, keratometry can be used to evaluate corneal power an anterior corneal surface measurement. In some cases, the ring is an elliptical shape having major and minor axes (e.g. where corneal astigmatism is present). Keratometry can be measured along the two orthogonal meridians, to provide maximum and minimum corneal power, and such extrema can be presented as corneal K's, or K-values. In some aspects, K-values can be used to quantify the central steepness of the cornea. Hence, systems may optionally include or use information obtained by keratometry devices (e.g. curvature values) and/or topography devices (e.g. elevation values). In some cases, topography information may be used to determine or approximate K-values.

Figure 16:
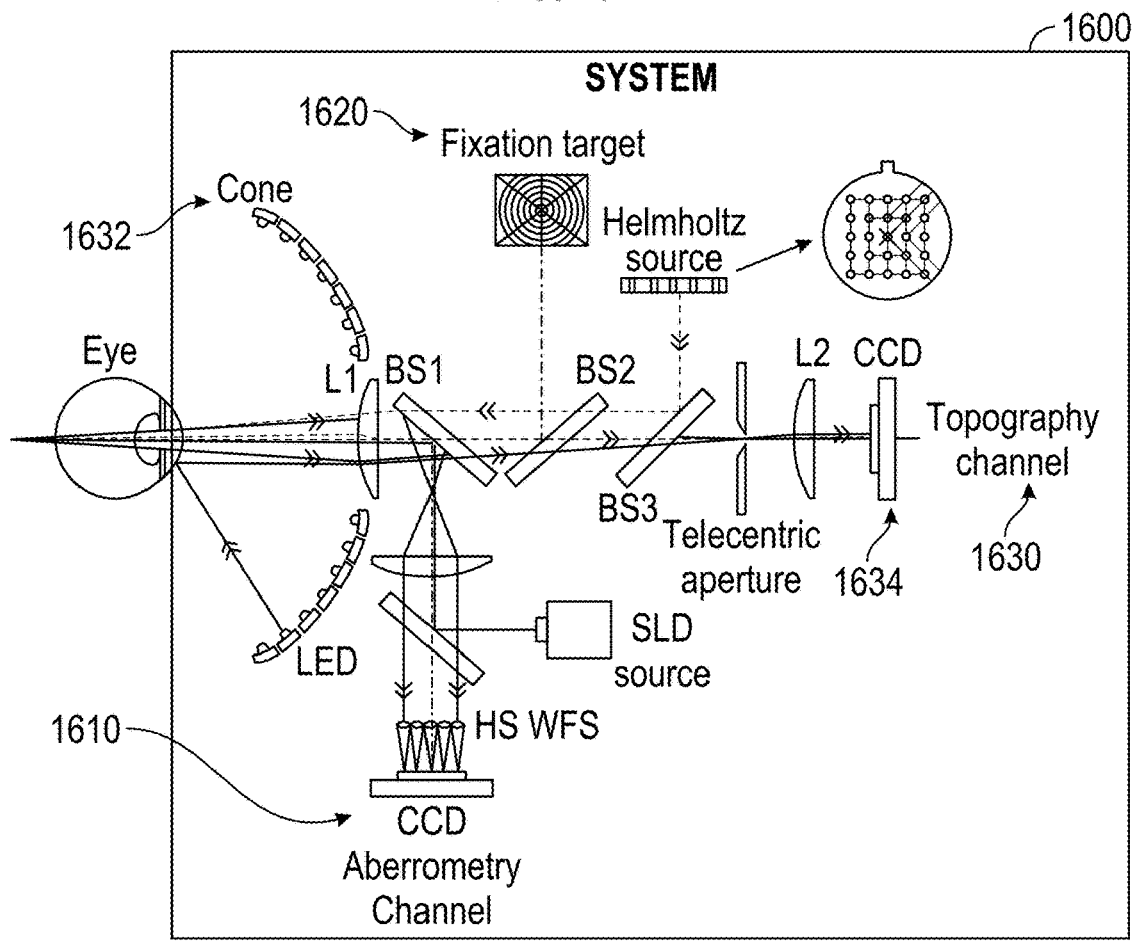
FIG. 16 depicts exemplary aspects of systems and methods according to embodiments of the present invention.

FIG. 16 depicts aspects of a system or apparatus 1600 for administering a refractive treatment to an eye of a patient, according to embodiments of the present invention. As shown here, system 1600 combines aberrometry and corneal topography measurements. System 1600 includes a wavefront sensor component 1610, which may be a Hartmann-Shack (HS WFS) type aberrometer. In some cases, wavefront sensor component 1610 includes a high definition wavefront aberrometer, such as the COAS-HD™ Model 2800. System 1600 also includes a fixation target 1620, which may be generated by a microdisplay. As shown here, system 1600 also includes a corneal topography apparatus 1630. In some instances, topography apparatus 1630 may be used to obtain K-values. Operation of the corneal topography apparatus 1630 may involve measuring the position of Purkinje I reflections on an array of light sources appropriately spaced on a cone-like surface 1632. The optical arrangement can create a grid of rectangularly and uniformly spaced Purkinje I reflections, that can be observed by a CCD detector 1634 (e.g. topography channel), for example when a calibration surface of average corneal dimensions is measured. The cone-like surface 1632 can be back illuminated by a Lambertian reflectance screen using 780 nm LEDs. This uniform light field can then be masked by an optically thick screen with appropriately spaced and angled fenestrations. This produces sources with a narrow forward emission primarily directed towards the focal plane of the anterior cornea and improves photometric efficiency of the instrument. The corneal gradient at each sample point can be determined by analyzing the translation of the spot position in two (x and y) directions. Translation of the spot position can allow calculation of the ray angle with respect to the surface normal at the sample location. As the ingoing ray angle is known from the instrument geometry, the gradient of the corneal surface is measured. Integration and an iterative search algorithm (based on Fermat's principle) allows reconstruction of the elevation data. The distance between the eye under measurement and the first optical element in the system can be measured in order to determine the radius of curvature. In the instrument, the distance can be measured by noting that the radius of curvature calculated from the Helmholtz spots (HHS) is independent of the eye position (since the light is projected through the collecting lens). For the corneal topography (CT) cone spots the pattern may depend on both the radius of curvature and the eye position. The position where the HHS pattern matches the CT pattern can yield the correct distance. The measurement of the corneal gradient can be in two directions. The corneal topography measurement data can be mapped onto the same axis as used for the aberrometry measurement (e.g. line of sight, or LOS), and the results can be presented to the operator following this mapping process. Sampling at the cornea can be 215 microns square (e.g. for an 8 mm radius of curvature cornea), and the sampling pattern may be slightly less dense in the central corneal region. The aberrometry and the corneal topography measurements may not be exactly simultaneous. In some cases, the time separation between these measurements is less than a tenth of a second. Each measurement can include multiple images, including for example a wavefront spot image, a corneal topography spot image, a scotopic iris (SI), and a photopic iris (PI). The latter three images (CT, SI and PI) can be recorded with the same camera but with different illumination. Both the aberrometry and topography systems may use a prerecorded reference to subtract any small residual errors in the optical systems. These can be optically recorded using ideal wavefront and cornea surface standards. The instrument's software can map the aberrometry and topography data sets onto a mutual coordinate system, and by exporting the raw corneal elevation data it is possible to retain the CT data in a format with its coordinate system centered along the VK axis.

In a patient having high cylinder, a standard surgery may improve the cylinder without improving the sphere. Relatedly, a standard surgery may increase the amount of high order aberration in a patient. However, various couplings have been determined to exist between certain low order aberrations, high order aberrations, and other optical properties. Such couplings can be used for improving final visual acuity, and other optical performance characteristics. For example, couplings have been observed between cylinder (pre-operative) and net sphere (post-operative). Hence, in some cases, both sphere and cylinder terms may be included in the analysis. For example, the multivariate techniques disclosed herein can be used to generate a treatment vector and/or influence matrix that corrects or compensates for this coupling, as well as those for the higher order terms. In some cases, this may involve a treatment vector that corrects or compensates for the coupling by adjusting a cylinder value so as to achieve a desired effect for sphere. Thus, according to embodiments of the present invention, it is possible to use an influence matrix or other effective treatment vector function to identify and/or compensate for a coupling between cylinder and sphere, and hence provide a solution that increases the overall accuracy of treatment. In another example, optical data from patients was analyzed, and correlations between cylinder (e.g. pre-treatment) and sphere (e.g. post-treatment) increased when keratometry data (e.g. pre-treatment K-values) was also considered. For example, a correlation coefficient of about 19% between cylinder and sphere was observed without using keratometry data, and a correlation coefficient of about 59% was observed when using keratometry data. In many cases, treatments were applied using the same treatment instrument, and preoperative and postoperative data was obtained using the same measurement instrument. According to embodiments of the present invention, improved correlations can be obtained when considering an array of optical properties, for example low order aberrations, high order aberrations, corneal topography measurements, optical coherence tomography measurements, corneal keratometry values, and related elements such as anterior and/or posterior chamber length or depth values, anterior and/or posterior corneal curvature values, axial length values, crystalline lens thickness values, radii of curvature values, tilt values (e.g. natural lens), lens decentration values (e.g. natural lens), induced astigmatism (or related corneal incision parameters such as incision orientation), pupil centration or decentration values (e.g. location of pupil center), pupil state (e.g. dilation), lighting levels (e.g. mesopic or photopic), physician-specific factors (e.g. surgical technique, previous history), planned treatment data (e.g. planned induced astigmatism), resulting treatment data (e.g. outcome or changed observed following treatment), Purkinje images, corneal flap dimension data (e.g. flap diameter or area), corneal hydration data, and the like. Such techniques can be applied in the context of laser-assisted in situ keratomileusis (LASIK), photorefractive keratectomy (PRK), laser-assisted sub-epithelial keratectomy (LASEK), radial keratometry, arcuate keratometry, and other laser refractive and/or corneal surgeries, as well as for intra-ocular lens treatments, contact lenses, spectacles, and the like.

In another example, optical parameter measurements were obtained directly from measurement instruments, in the absence of any physician adjustments, and similar correlations were observed. In some cases, for each diopter of cylinder, a corresponding ⅛ diopter of sphere was observed. Hence, in a patient having a high cylinder value (e.g. −3 D, −4 D), a corresponding difference in sphere of about ⅜ D or ⅘ D was observed.

In some instances, strong couplings have been observed between K-values and one or more higher order aberrations. Hence, for example, it is possible to determine a correction or adjustment in K-values that would result in a desired result for spherical aberration. In this way, a result may be more predictable when considering both the K-values and the aberrations. For example, the multivariate techniques disclosed herein can be used to generate a treatment vector and/or influence matrix that corrects or compensates for this coupling. In some cases, this may involve a treatment vector that corrects or compensates for the coupling by adjusting a K-value so as to achieve a desired effect for spherical aberration.

In some cases, it may be possible to reduce high order aberrations that may otherwise be induced as a result of surgery. For example, where a particular corneal incision or relaxation cut may induce an amount of cylinder or astigmatism, it may be possible to plan an ocular treatment that incorporates the formation of such incisions, before or in addition to performing the surgery. In this way, it may be possible to use techniques described herein to compensate in advance for the effect of a surgery.

The principles described above for improved treatment planning for laser refractive surgery may also be applied to cataract surgery to provide improved treatment planning for laser refractive surgery may also be applied to devices, systems, and methods for diagnosing and/or treating cataracts to increase the overall accuracy with which intraocular lenses for cataract surgery are specified, selected, and located within an eye.

Exemplary embodiments of optical measurement systems and methods for cataract diagnostics to illustrate various aspects and advantages of these devices and methods are described below. However, it should be understood that the principles involved in these devices and methods can be employed in a variety of other contexts, and therefore the novel devices and method disclosed and claimed here should not be construed as being limited to the example embodiments described below.

Figure 17A:
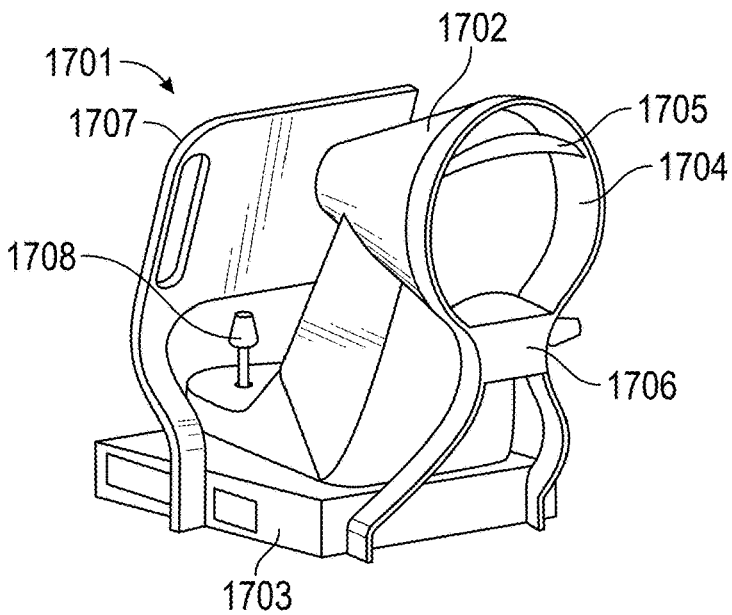
FIG. 17A illustrates a front perspective view showing an optical measurement system according to some embodiments.
Figure 17B:
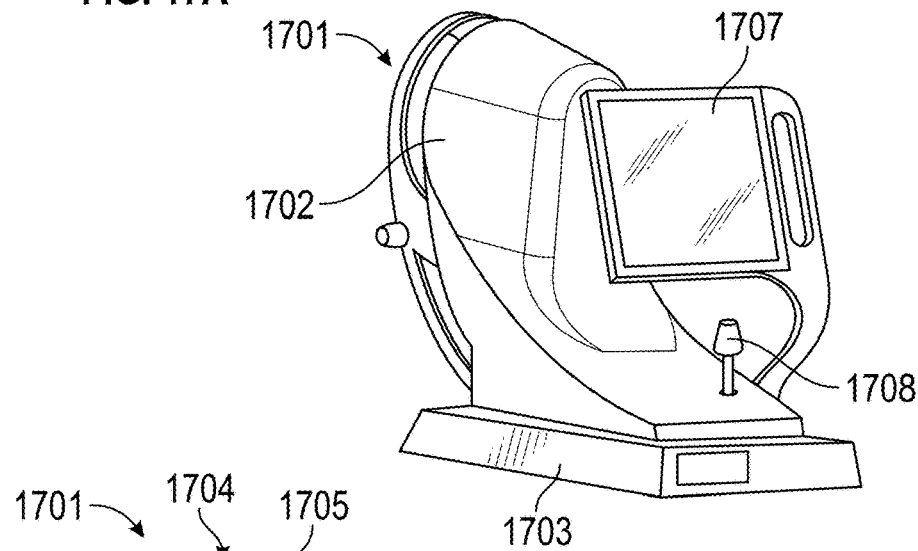
FIG. 17B illustrates a rear perspective view showing an optical measurement system according to some embodiments.
Figure 17C:
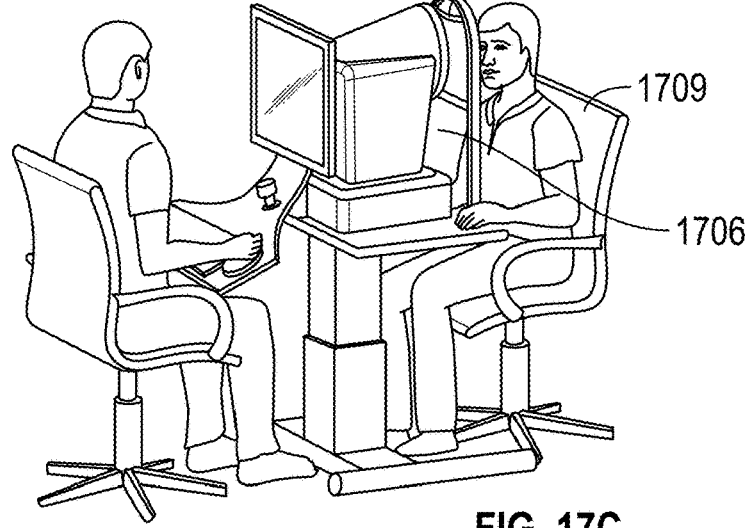
FIG. 17C illustrates a side perspective view showing an optical measurement system according to some embodiments.

As shown in FIGS. 17A-17C, an optical measurement system 1701, according to many embodiments, is operable to provide for a plurality of measurements of the human eye, including measurements of the cornea, the lens capsule, the lens and the retina. The main unit 1702 comprises a base 1703 and includes many primary subsystems of many embodiments of the system 1701. For example, externally visible subsystems include a touch-screen display control panel 1707, a patient interface assembly 1704 and a joystick 1708.

The patient interface assembly 1704 beneficially includes one or more structures configured to hold a patient's head in a stable, immobile and preferably comfortable position during the measurement measurements while also maintaining the eye of the patient in a suitable alignment with the measurement system. In a particularly preferred embodiment, the eye of the patient remains in substantially the same position relative to the measurement system for all measurement and imaging measurements performed by the system 1701.

In one embodiment the patient interface includes a chin support 1706 and/or a forehead rest 1704 configured to hold the head of the patient in a single, uniform position suitably aligned with respect to the system 1701 throughout the measurement. As shown in FIG. 18C, the optical measurement system 1701 is preferably disposed so that the patient may be seated in a patient chair 1709. The patient chair 1709 can be configured to be adjusted and oriented in three axes (x, y, and z) so that the patent's head can be at a suitable height and lateral position for placement on the patient interface.

In many embodiments, the system 1701 may include external communication connections. For example, the system 1701 can include a network connection (e.g., an RJ45 network connection) for connecting the system 1701 to a network. The network connection can be used to enable network printing of measurement reports, remote access to view patient measurement reports, and remote access to perform system diagnostics. The system 1701 can include a video output port (e.g., HDMI) that can be used to output video of measurements performed by the system 1702. The output video can be displayed on an external monitor for, for example, viewing by physicians or users. The output video can also be recorded, for example, for archival purposes. The system 1702 can include one or more data output ports (e.g., USB) to enable export of patient measurement reports to, for example, a data storage device or a computer readable medium, for example a non-volatile computer readable medium, coupled to a laser cataract surgery device for use of the measurements in conducting laser cataract surgeries. The measurement reports stored on the data storage device or computer readable medium can then be accessed at a later time for any suitable purpose such as, for example, printing from an external computer in the case where the user without access to network based printing or for use during cataract surgery, including laser cataract surgery.

Figure 18:
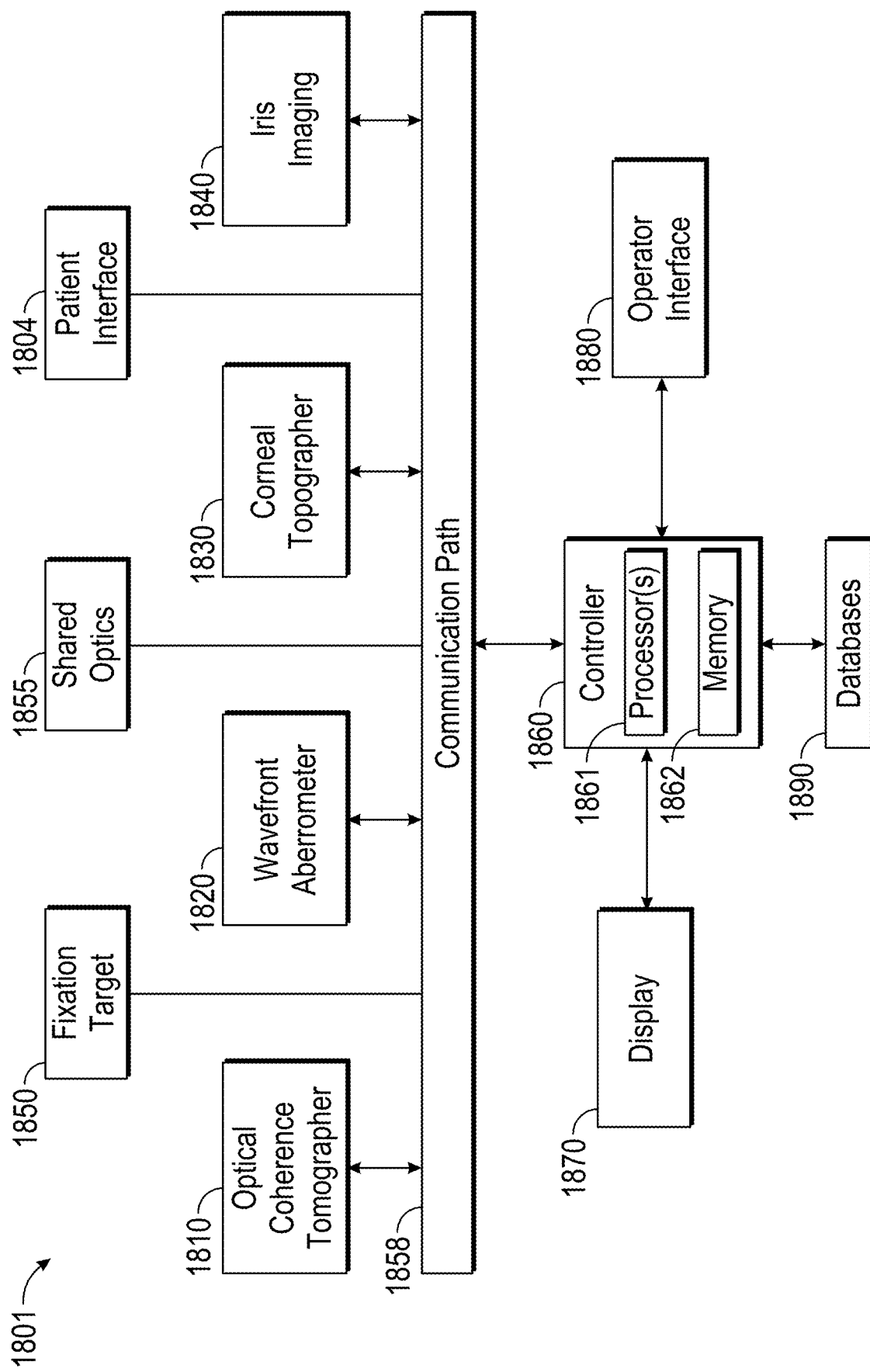
FIG. 18 is a block diagram of a system including an optical measurement instrument, and a position of an eye relative to the system according to one or more embodiments described herein which may be used by the optical measurement.

FIG. 18 is a block diagram of a system including an optical measurement instrument 1801 according to one or more embodiments described herein. Optical measurement instrument 1801 includes: an optical coherence tomographer (OCT) subsystem 1810, a wavefront aberrometer subsystem 1820, and a corneal topographer subsystem 1830 for measuring one or more characteristics of a subject's eye. Optical measurement instrument 1801 may further include an iris imaging subsystem 1840, a fixation target subsystem 1850, a controller 1860, including one or more processor(s) 1861 and memory 1862, a display 1870 and an operator interface 1880. Optical measurement instrument 1801 further includes a patient interface 1804 for a subject to present his or her eye for measurement by optical measurement instrument 1801.

The optical coherence tomography subsystem 1810 is configured to measure the spatial disposition (e.g., three-dimensional coordinates such as X, Y, and Z of points on boundaries) of eye structures in three dimensions. Such structures of interest can include, for example, the anterior surface of the cornea, the posterior surface of the cornea, the anterior portion of the lens capsule, the posterior portion of the lens capsule, the anterior surface of the crystalline lens, the posterior surface of the crystalline lens, the iris, the pupil, the limbus, an implanted intraocular lens, and/or the retina. The spatial disposition of the structures of interest and/or of suitable matching geometric modeling such as surfaces and curves can be generated and/or used by the controller 1860 for a number of purposes, including, in some embodiment to program and control a subsequent laser-assisted surgical procedure, or the specification of an intraocular lens and its placement location within an eye. The spatial disposition of the structures of interest and/or of suitable matching geometric modeling can also be used to determine a wide variety of parameters.

As a non-limiting example, the system 1801 can be configured to use a swept source OCT imaging system employing wavelengths of around 1060 nm with an 8 mm scan depth. The spatial disposition of the eye structures using optical coherence tomography should generally be measured while the patient is engaged with patient interface 1804. The OCT scan depth is preferably between 8 and 50 mm, and the scan depth is preferably greater than about 24 mm or even 30 mm to achieve a full eyescan depth. The swept source wavelengths can be centered at wavelengths from 840 nm to 1310 nm.

Optical coherence tomographer subsystem 1810 is only one example of an eye structure imaging subsystem which may be employed in optical measurement instrument 1801. In other embodiments, a different eye structure imaging subsystem may be employed, for example a Scheimpflug Imager, a fluorescence imager, a structured lighting imager, a wavefront tomographer, an ultrasound imager and a plenoptic imager.

The wavefront aberrometer subsystem 1820 is configured to measure ocular aberrations, preferably including low and high order aberrations, by measuring the wavefront emerging from the eye by, for example a Hartmann-Shack wavefront sensor The corneal topographer subsystem 1830 may apply any number of modalities to measure the shape of the cornea including one or more of a keratometry reading of the eye, a corneal topography of the eye, an optical coherence tomography of the eye, a Placido disc topography of the eye, a reflection of a plurality of points from the cornea topography of the eye, a grid reflected from the cornea of the eye topography, a Hartmann-Shack measurement of the eye, a Scheimpflug image topography of the eye, a confocal tomography of the eye, a Helmholtz source topographer, or a low coherence reflectometry of the eye. The shape of the cornea should generally be measured while the patient is engaged with patient interface 1804.

Fixation target system 1850 is configured to control the patient's accommodation, because it is often desired to measure the refraction and wavefront aberrations when eye 1901 (see FIG. 19A) is focused at its far point Images captured by the corneal topographer subsystem 1810, the wavefront aberrometer 1820, the optical coherence tomographer subsystem 1830 or the camera 1840 may be displayed with a display of the operator interface 1880 of the optical measurement system 1801 or the display 1870 of the optical measurement system, respectively. The operator interface may also be used to modify, distort, or transform any of the displayed images.

The shared optics 1855 provide a common propagation path that is disposed between the patient interface 1804 and each of the optical coherence tomography (OCT) subsystem 1810, the wavefront aberrometer subsystem 1820, the corneal topographer subsystem 1830, and in some embodiments, the camera 1840, and the fixation target 1850. In many embodiments, the shared optics 1855 may comprise a number of optical elements, including mirrors, lenses and beam combiners to receive the emission from the respective subsystem to the patient's eye and, in some cases, to redirect the emission from a patient's eye along the common propagation path to an appropriate director.

The controller 1860 controls the operation of the optical measurement instrument 1801 and can receive input from any of the optical coherence tomographer (OCT) subsystem 1810, the wavefront aberrometer subsystem 1820, the corneal topographer subsystem 1830 for measuring one or more characteristics of a subject's eye, the camera 1840, the fixation target 1850, the display 1870 and the operator interface 1880 via the communication paths 1858. The controller 1860 can include any suitable components, such as one or more processors, one or more field-programmable gate array (FPGA), and one or more memory storage devices. In many embodiments, the controller 1860 controls the display 1870 to provide for user control over a laser eye surgery procedure, for pre-cataract procedure planning according to user specified treatment parameters as well as to provide user control over laser eye surgery procedure. The communication paths 1858 can be implemented in any suitable configuration, including any suitable shared or dedicated communication paths between the controller 1860 and the respective system components.

The operator interface 1880 can include any suitable user input device suitable to provide user input to the controller 1860. For example, the user interface devices 1880 can include devices such as joystick 1808, a keyboard or a touchscreen display 1870.

Figure 19A:
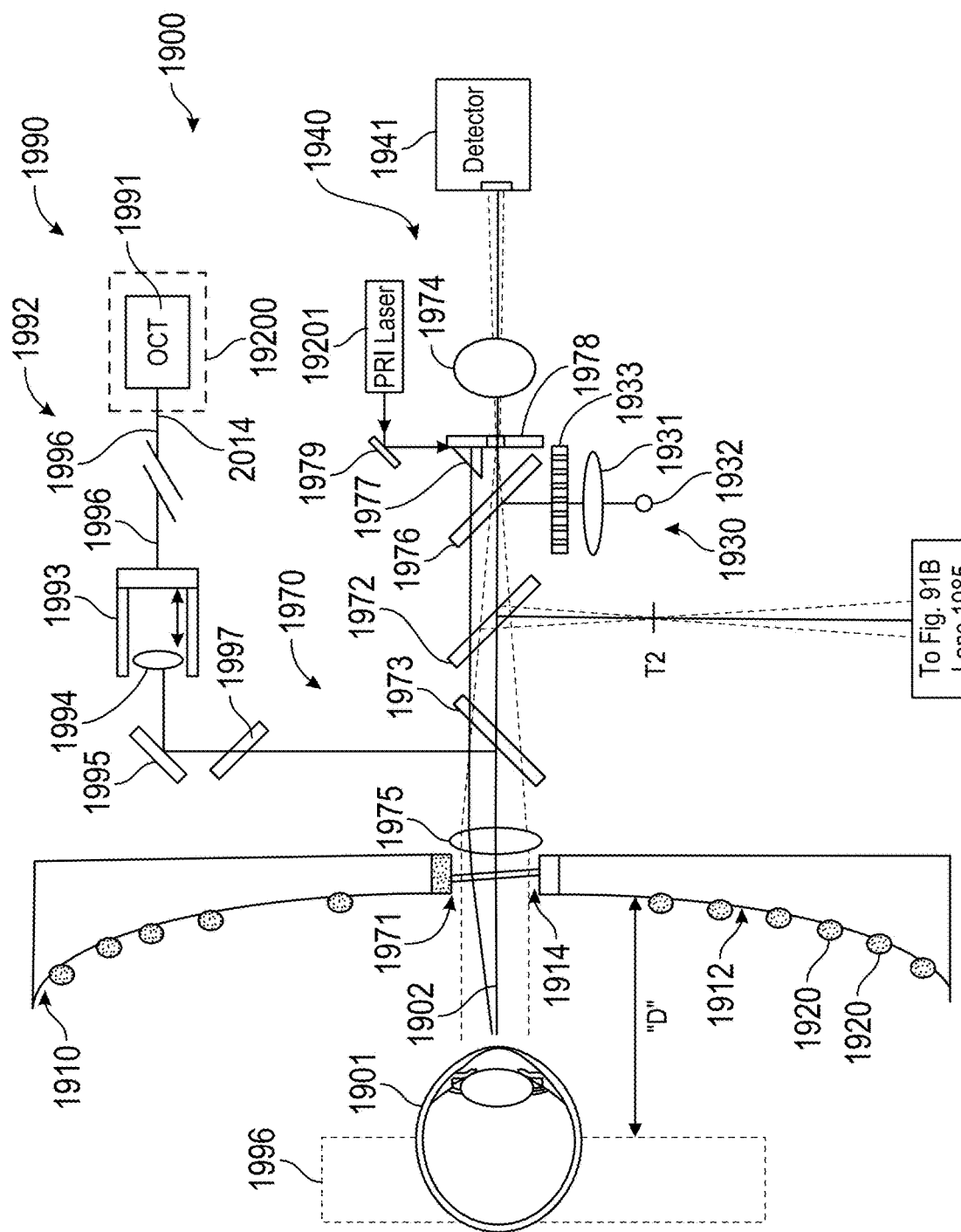
FIGS. 19A and 19B illustrate together an assembly of a suitable configuration and integration of an optical coherence tomographer subsystem, a wavefront aberrometer subsystem, a corneal topographer subsystem, an iris imaging subsystem, a fixation target subsystem according to a non-limiting embodiment of the present invention.
Figure 19B:
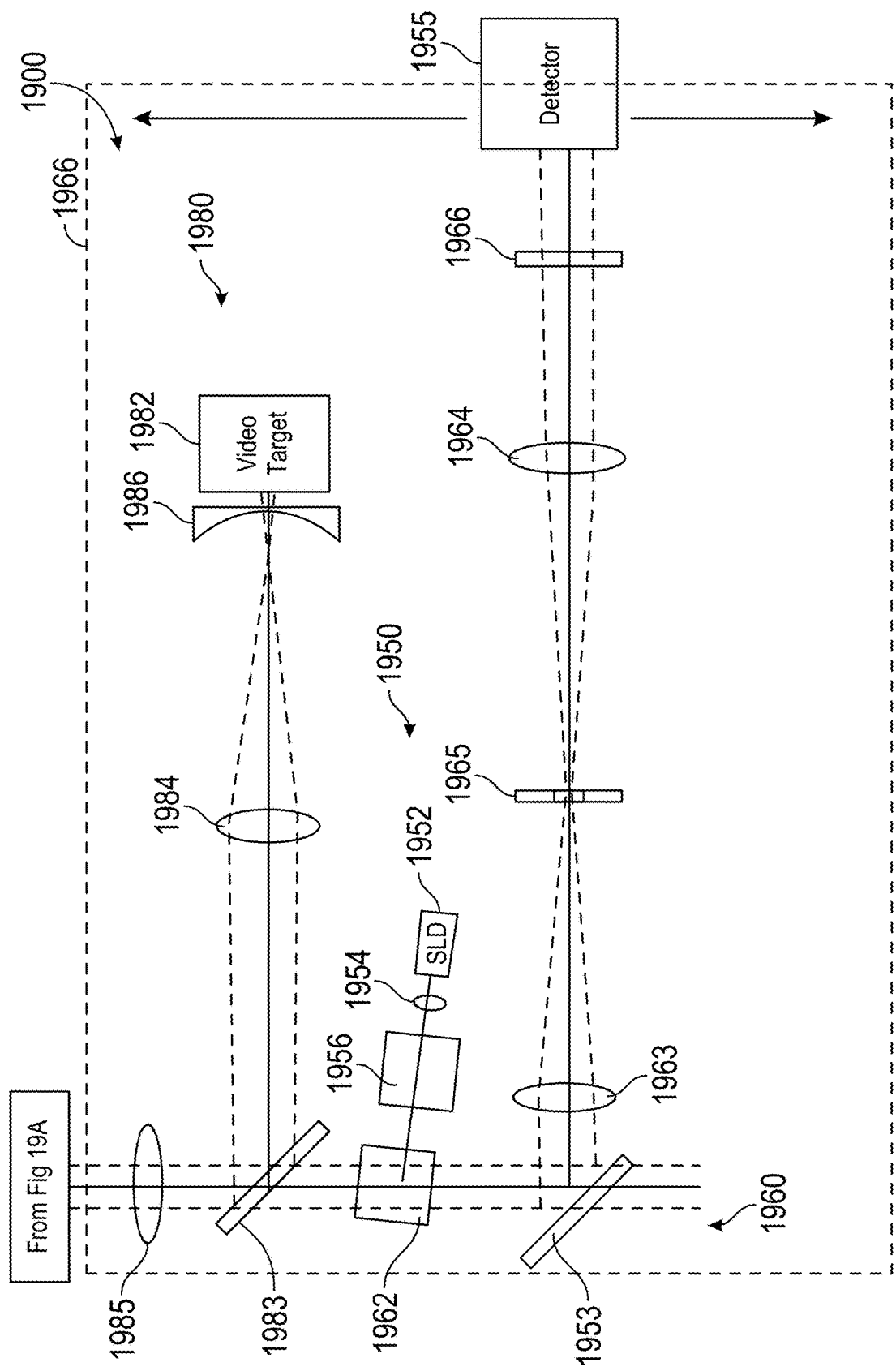

FIGS. 19A and 19B are simplified block diagrams illustrating an assembly 1900 according to many embodiments, which can be included in the system 1801. The assembly 1900 is a non-limiting example of suitable configurations and integration of the optical coherence tomographer (OCT) subsystem 1890, the wavefront aberrometer subsystem 1850, the corneal topographer subsystem 1810 for measuring one or more characteristics of a subject's eye, a camera 1840, the fixation target subsystem 1850 and the shared optics 1855.

The shared optics generally comprise one or more components of a first optical system 1970 disposed along a central axis 1902 passing through the opening or aperture 1914 of the structure 1910. A first optical system 1970 directs light from the various light sources along the central axis 1902 towards the eye and establishes a shared or common optical path along which the light from the various light sources travel to the eye 1901. In one embodiment, optical system 1970 comprises a quarter wave plate 1971, a first beamsplitter 1972, a second beamsplitter 1973, an optical element (e.g., a lens) 1974, a second lens 1975, a third beamsplitter 1976, and a structure including an aperture 1978. Additional optical systems may be used in assembly 1900 to direct light beams from one or more light sources to the first optical system 1970. For example, a second optical system 1960 directs light to the first optical system 1970 from the wavefront aberrometer subsystem 1950 and comprises mirror 1953, beamsplitter 1962 and beamsplitter 1983 and lens 1985.

Other configurations of the assembly 1900 may be possible and may be apparent to a person of skill in the art.

The corneal topographer subsystem 1940 comprises a structure 1910 having a principal surface 1912 with an opening or aperture 1914 therein; a plurality of first (or peripheral) light sources 1920 provided on the principal surface 1912 of the structure 1910; a Helmholtz light source 1930; and a detector, photodetector, or detector array 1941.

In one embodiment, structure 1910 has the shape of an elongated oval or "zeppelin" with openings or apertures at either end thereof. An example of such a structure is disclosed in Yobani Meji'a-Barbosa et al., "Object surface for applying a modified Hartmann test to measure corneal topography," APPLIED OPTICS, Vol. 40, No. 31 (Nov. 1, 2001) ("Meji'a-Barbosa"). In some embodiments, principal surface 1912 of structure 1910 is concave when viewed from the cornea of eye 1901, as illustrated in FIG. 19A.

In one embodiment where principal surface 1912 is concave, principal surface 1912 has the shape of a conical frustum. Alternatively, principal surface 1912 may have a shape of hemisphere or some other portion of a sphere, with an opening or aperture therein. Also alternatively, principal surface 1912 may have the shape of a modified sphere or conical frustum, with a side portion removed. Beneficially, such an arrangement may improve the ergonomics of assembly 1900 by more easily allowing structure 1910 to be more closely located to a subject's eye 1901 without being obstructed by the subject's nose. Of course, a variety of other configurations and shapes for principal surface 1912 are possible.

In the embodiment of FIG. 19A, the plurality of first light sources 1920 are provided on the principal surface 1912 of structure 1910 so as to illuminate the cornea of eye 1901. In one embodiment, light sources 1922 may comprise individual light generating elements or lamps, such as light emitting diodes (LEDs) and/or the tips of the individual optical fibers of a fiber bundle. Alternatively, principal surface 1912 of structure 1910 may have a plurality of holes or apertures therein, and one or more backlight lamps, which may include reflectors and/or diffusers, may be provided for passing lighting through the holes to form the plurality of first light sources 1920 which project light onto the cornea of eye 1901. Other arrangements are possible.

In another embodiment, structure 1910 is omitted from assembly 1900, and the first light sources 1920 may be independently suspended (e.g., as separate optical fibers) to form a group of first light sources 1920 arranged around a central axis, the group being separated from the axis by a radial distance defining an aperture in the group (corresponding generally to the aperture 1914 in the structure 1910 illustrated in FIG. 19A).

In operation, a ray (solid line) from one of the first light sources 1920 is reflected by the cornea and passes through optical system 1970 (including aperture 1978) to appear as a light spot on detector array 1941. It will be appreciated that this ray is representative of a small bundle of rays that make it through optical system 1970 and onto detector array 1941, all of which will focus to substantially the same location on detector array 1941. Other rays from that first light source 1920 are either blocked by the aperture 1978 or are otherwise scattered so as to not pass through the optical system 1970. In similar fashion, light from the other first light sources 1920 are imaged onto detector array 1941 such that each one of first light sources 1920 is imaged or mapped to a location on detector array 1941 that may be correlated to a particular reflection location on the cornea of eye 1901 and/or the shape of the cornea. Thus, detector array 1941 detects the light spots projected thereon and provides corresponding output signals to a processor of controller 1860 (FIG. 18). The processor determines the locations and/or shape of the light spots on detector array 1941, and compares these locations and/or shapes to those expected for a standard or model cornea, thereby allowing the processor of controller 1860 to determine the corneal topography. Alternatively, other ways of processing the spot images on detector array 1941 may be used to determine the corneal topography of eye 1901, or other information related to the characterization of eye 1901.

Detector array 1941 comprises a plurality of light detecting elements arranged in a two dimensional array. In one embodiment, detector array 1941 comprises such a charge-coupled device (CCD), such as may be found in a video camera. However, other arrangements such as a CMOS array, or another electronic photosensitive device, may be employed instead. Beneficially, the video output signal(s) of detector array 1941 are provided to processor 1861 which processes these output signals as described in greater detail below.

Assembly 1900 also comprises a Helmholtz light source 1930 configured according to the Helmholtz principle. As used herein, the term "Helmholtz source" or "Helmholtz light source" means one or a plurality of individual light sources disposed such that light from each of the individual light sources passes through an optical element having optical power, reflects off of a reference or test object, passes through the optical element, and is received by a detector, wherein light from the Helmholtz source is used to determine geometric and/or optical information of at least a portion of a surface of the reference or test object. In general, it is a characteristic of Helmholtz sources that the signal at the detector is independent of the relative position of the test or reference object relative to the Helmholtz source. As used herein, the term "optical element" means an element that refracts, reflects, and/or diffracts light and has either positive or negative optical power.

In such embodiments, the Helmholtz light source 1930 is located at optical infinity with respect to eye 1901. The Helmholtz principle includes the use of such infinite sources in combination with a telecentric detector system: i.e., a system that places the detector array at optical infinity with respect to the surface under measurement, in addition to insuring that the principal measured ray leaving the surface is parallel to the optical axis of the instrument. The Helmholtz corneal measurement principle has the Helmholtz light source at optical infinity and the telecentric observing system so that detector array 1941 is also optically at an infinite distance from the images of the sources formed by the cornea. Such a measurement system is insensitive to axial misalignment of the corneal surface with respect to the instrument.

In one embodiment, the Helmholtz light source 1930 comprises a second light source 1932 which may comprise a plurality of lamps, such as LEDs or optical fiber tips. In one embodiment, second light source 1932 comprises an LED and a plate 1933 with plurality of holes or apertures in a surface that are illuminated by one or more backlight lamps with an optical element 1931, which may comprise diffusers.

In one embodiment, second light sources 1932 are located off the central optical axis 1902 of assembly 1900, and light from second light sources 1932 is directed toward optical element 1971 by third beamsplitter 1976.

The operation of the topographer portion of assembly 1900 may be conducted with the combined use of first light source 1920 and the Helmholtz light source 1930. In operation, detector array 1941 detects the light spots projected thereon from both Helmholtz light source 1930 (detected at a central portion of detector array 1941) and first light sources 1920 (detected at a peripheral portion of detector array 1941) and provides corresponding output signals to processor. In general, the images of first light sources 1920 that appear on detector array 1940 emanate from an outer region of the surface of the cornea, and the images of Helmholtz light source 1930 that appear on detector array 1941 emanate from a central or paraxial region of the surface of the cornea. Accordingly, even though information about the central region of the corneal surface (e.g., surface curvature) cannot be determined from the images of first light sources 1920 on detector array 1941, such information can be determined from the images of Helmholtz light source 1930 on detector array 1941. A processor of controller 1860 determines the locations and/or shapes of the light spots on detector array 1941, and compares these locations and/or shapes to those expected based for a standard or model cornea, thereby allowing the processor to determine the corneal topography of eye 1901. Accordingly, the topography of the entire corneal surface can be characterized by assembly 1900 without a "hole" or missing data from the central corneal region.

A fourth light source 19201 off the central axis 1902 may be directed along optical axis 1902 by mirrors 1977, 1979 disposed on or near the aperture 1978, perpendicular to the optical axis 1902 are configured as a pupil retroreflection illuminator. The pupil retroreflection illuminator is configured to direct a disc of light toward a patient's eye, whereby the disc of light may be reflected from reflective surfaces within the eye, and the reflected light is transmitted by optical path 1970 to detector 1941. The pupil retroreflection illuminators may optionally be configured such that, when a patient's pupil is dilated, the disc of light from light source 19201 is reflected from an implanted IOL to image the IOL, including any fiducial marks; if IOL is imperfectly placed, detector 1941 may be used to determine IOL edges are decentered. Also, images from detector 1941 using the pupil retroreflection illuminator may see folds, for instance, unfolded edge if the IOL did not unfold properly.

The wavefront aberrometer subsystem 1950 of the assembly 1900 comprises a third light source 1952 providing a probe beam and a wavefront sensor 1955. The Wavefront aberrometer subsystem 1950 preferably further comprises a collimating lens 1954, a polarizing beamsplitter 1956, an adjustable telescope comprising a first optical element, lens 1963 and a second optical element, lens 1964, a movable stage or platform 1966, and a dynamic-range limiting aperture 1965 for limiting a dynamic range of light provided to wavefront sensor 1955 so as to preclude data ambiguity. Light from the wavefront aberrometer subsystem is directed to one of the constituent optical elements of the optical system 1970 disposed along a central axis 1902 passing through the opening or aperture 1914 of the structure 1910. It will be appreciated by those of skill in the art that the lenses 1963, 1964, or any of the other lenses discussed herein, may be replaced or supplemented by another type of converging or diverging optical element, such as a diffractive optical element.

Light source 1952 is preferably an 840 nm SLD (super luminescent laser diode). An SLD is similar to a laser in that the light originates from a very small emitter area. However, unlike a laser, the spectral width of the SLD is very broad, about 40 nm. This tends to reduce speckle effects and improve the images that are used for wavefront measurements.

Preferably, wavefront sensor 1955 is a Hartmann-Shack wavefront sensor comprising a detector array and a plurality of lenslets for focusing received light onto its detector array. In that case, the detector array may be a CCD, a CMOS array, or another electronic photosensitive device. However, other wavefront sensors may be employed instead. Embodiments of wavefront sensors which may be employed in one or more systems described herein are described in U.S. Pat. No. 6,550,917, issued to Neal et al. on Apr. 22, 2003, and U.S. Pat. No. 5,777,719, issued to Williams et al. on Jul. 7, 1998, both of which patents are hereby incorporated herein by reference in their entirety.

The aperture or opening in the middle of the group of first light sources 1920 (e.g., aperture 1914 in principal surface 1912 of structure 1910) allows assembly 1900 to provide a probe beam into eye 1901 to characterize its total ocular aberrations. Accordingly, third light source 1952 supplies a probe beam through a light source polarizing beamsplitter 1956 and polarizing beamsplitter 1962 to first beamsplitter 1972 of optical system 1970. First beamsplitter 1972 directs the probe beam through aperture 1914 to eye 1901. Preferably, light from the probe beam is scattered from the retina of eye 1901, and at least a portion of the scattered light passes back through aperture 1914 to first beamsplitter 1972. First beamsplitter 1972 directs the back scattered light back through beamsplitter 1972 to polarizing beamsplitter 1962, mirror 1953 to wavefront sensor 1955.

Wavefront sensor 1955 outputs signals to a processor 1861 of controller 1860 which uses the signals to determine ocular aberrations of eye 1901. Preferably, processor 1861 is able to better characterize eye 1901 by considering the corneal topography of eye 1901 measured by the corneal topography subsystem, which may also be determined by processor 1861 based on outputs of detector array 1941, as explained above.

In operation of the wavefront aberrometer subsystem 1950, light from light source 1952 is collimated by lens 1954. The light passes through light source polarizing beamsplitter 1956. The light entering light source polarizing beamsplitter 1956 is partially polarized. Light source polarizing beamsplitter 1956 reflects light having a first, S, polarization, and transmits light having a second, P, polarization so the exiting light is 100% linearly polarized. In this case, S and P refer to polarization directions relative to the hypotenuse in light source polarizing beamsplitter 1956.

Light from light source polarizing beamsplitter 1956 enters polarizing beamsplitter 1962. The hypotenuse of polarizing beamsplitter 1962 is rotated 90 degrees relative to the hypotenuse of light source polarizing beamsplitter 1956 so the light is now S polarized relative the hypotenuse of polarizing beamsplitter 1962 and therefore the light reflects upwards. The light from polarizing beamsplitter 1962 travels upward and passes through toward beamsplitter 1972, retaining its S polarization, and then travels through quarter wave plate 1971. Quarter wave plate 1971 converts the light to circular polarization. The light then travels through aperture 1914 in principal surface 1912 of structure 1910 to eye 1901. Preferably, the beam diameter on the cornea is between 1 and 2 mm. Then the light travels through the cornea and focuses onto the retina of eye 1901.

The focused spot of light becomes a light source that is used to characterize eye 1901 with wavefront sensor 1955. Light from the probe beam that impinges on the retina of eye 1901 scatters in various directions. Some of the light reflects back as a semi-collimated beam back towards assembly 1900. Upon scattering, about 90% of the light retains its polarization. So the light traveling back towards assembly is substantially still circularly polarized. The light then travels through aperture 1914 in principal surface 1912 of structure 1910, through quarter wave plate 1971, and is converted back to linear polarization. Quarter wave plate 1971 converts the polarization of the light from the eye's retina so that it is P polarized, in contrast to probe beam received from third light source 1950 having the S polarization. This P polarized light then reflects off of first beamsplitter 1972, and then reaches polarizing beamsplitter 1962. Since the light is now P polarized relative the hypotenuse of polarizing beamsplitter 1962, the beam is transmitted and then continues onto mirror 1953. After being reflected by mirror 1953, light is sent to an adjustable telescope comprising a first optical element 1964 and a second optical element (e.g., lens) 1963 and a movable stage or platform 1966. The beam is also directed through a dynamic-range limiting aperture

1965 for limiting a dynamic range of light provided to wavefront sensor 1955 so as to preclude data ambiguity.

When wavefront sensor 1955 is a Hartmann-Shack sensor, the light is collected by the lenslet array in wavefront sensor 1955 and an image of spots appears on the detector array (e.g., CCD) in wavefront sensor 1955. This image is then provided to a process of the controller 1860 and analyzed to compute the refraction and aberrations of eye 1901.

An OCT subsystem 1990 of assembly 1900 preferably comprises an OCT assembly 1991, and a third optical path 1992 which directs the OCT beam of the OCT light source to the first optical path 1970. The third optical path 1992 preferably comprises a fiber optic line 1996, for conducting the OCT beam from the OCT light source, a z-scan device 1993 operable to alter the focus of the beam in the z-direction (i.e., along the direction of propagation of the OCT beam) under control of the controller 1860, and x-scan device 1995, and a y-scan device 1997 operable to translate the OCT beam in the x and y directions (i.e., perpendicular to the direction of propagation of the of the OCT beam), respectively, under control of the controller 1860. The OCT light source and reference arm may be incorporated into the main unit 4 of the optical measurement instrument 1701 shown in FIG. 17A. Alternatively, the OCT assembly 1991 may be housed in a second unit 19200 and the OCT beam from the OCT source may be directed from the second housing 19200 to the main unit by optical pathway 1992.

The OCT systems and methods of the present invention are preferably FD-OCT (Fourier domain optical coherence tomography) systems, including either an SD-OCT (spectral domain optical coherence tomography) system or, more preferably, an SS-OCT (swept source optical coherence tomography) system. In conventional FD-OCT systems, the interference signal is distributed and integrated over numerous spectral wavelength intervals, and is inverse Fourier transformed to obtain the depth-dependent reflectivity profile of the sample. The profile of scattering as a function of depth is referred to as an A-scan (Axial-scan). The beam can be scanned laterally to produce a set of A-scans that can be combined together to form a tomogram of the sample (a B-scan).

In an SD-OCT system, various spectral wavelength intervals of the combined returned light from the reference and sample arms are spatially encoded using, for instance, a collimator, diffraction grating, and a linear detector array. Resampling of the data obtained from the linear detector array is performed in order to correct for the nonlinear spatial mapping of wavenumbers. After resampling and subtraction of the dc background, the depth profile structural information is obtained by performing the inverse Fourier transform operation. In swept-source OCT, the broad bandwidth optical source is replaced by a rapid-scanning laser source. By rapidly sweeping the source wavelength over a broad wavelength range, and collecting all the scattering information at each wavelength and at each position, the composition of the collected signal is equivalent to the spectral-domain OCT technique. The collected spectral data is then inverse Fourier transformed to recover the spatial depth-dependent information.

FD-OCT suffers from an inherent sample-independent limited depth range, typically between 1 and 5 mm. One limitation flows from the fact that FD-OCT extracts depth information from the inverse Fourier transform of a spectral interferogram. Since the spectral interferogram can only be recorded as a real signal, its Fourier transform is necessarily Hermitian symmetric about the zero path length difference (ZPD) position. As a result, the positive and negative displacements about the ZPD cannot be unambiguously resolved, which gives rise to mirror image artifacts and generally halves the useable range. This is referred to as the complex conjugate ambiguity. Another limitation is a sensitivity fall-off which results in reduced sensitivity with increasing depth. Moreover, since the signal in OCT is derived only from backscattered photons, optical attenuation from absorption and scattering generally result in a useable imaging depth of about 1-4 mm.

Several "full range" OCT techniques have been developed that eliminate the complex conjugate artifacts to effectively double the measurement range around the ZPD position. These full range OCT techniques result in useable imaging depths of up to about 5 mm up to about 8 mm. Suitable full range techniques are methods utilizing a dithering reference lag to break the phase ambiguity, methods that use phase distortion, and other suitable methods.

Figure 20:
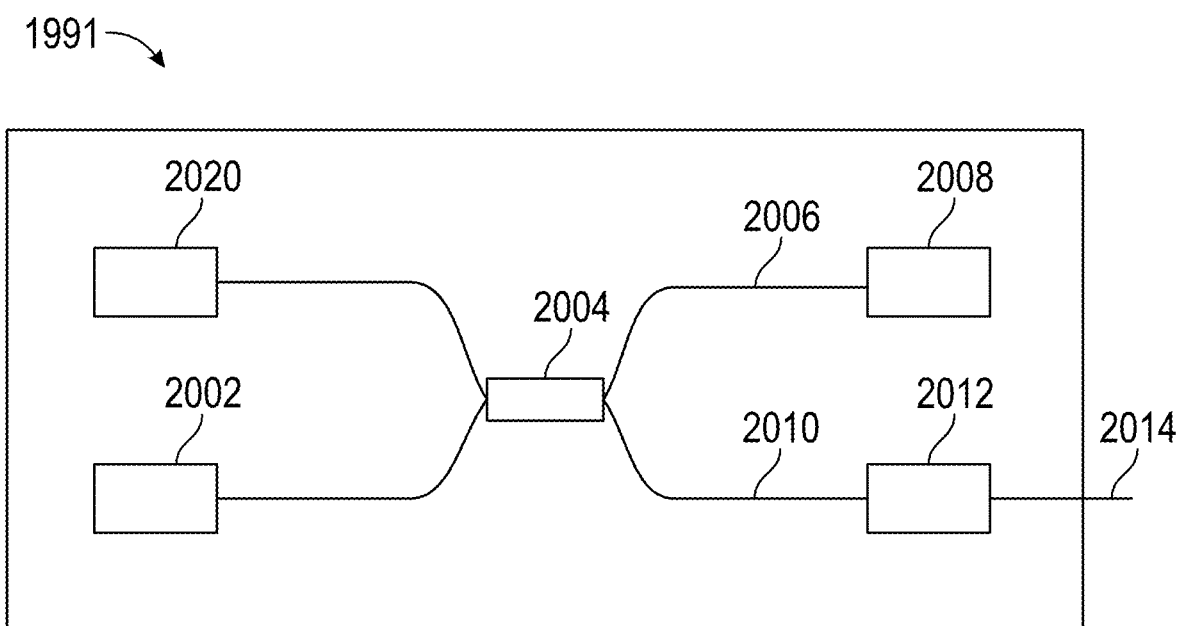
FIG. 20 is a block diagram of an OCT assembly according to many embodiments of the present invention.

As shown in FIG. 20, the OCT assembly 1991 of OCT subsystem 1990 includes a broadband or a swept light source 202 that is split by a coupler 204 into a reference arm 206 and a sample arm 210. The reference arm 106 includes a module 108 containing a reference reflection along with suitable dispersion and path length compensation. The sample arm 110 of the OCT assembly 191 has an output connector 212 that serves as an interface to the rest of the optical measurement instrument. The return signals from both the reference and sample arms 206, 210 are then directed by coupler 204 to a detection device 220, which employs either time domain, frequency or single point detection techniques. In FIG. 20, a swept source technique is used with a laser wavelength of 1060 nm swept over a range of 8-50 mm depth.

Figure 21:
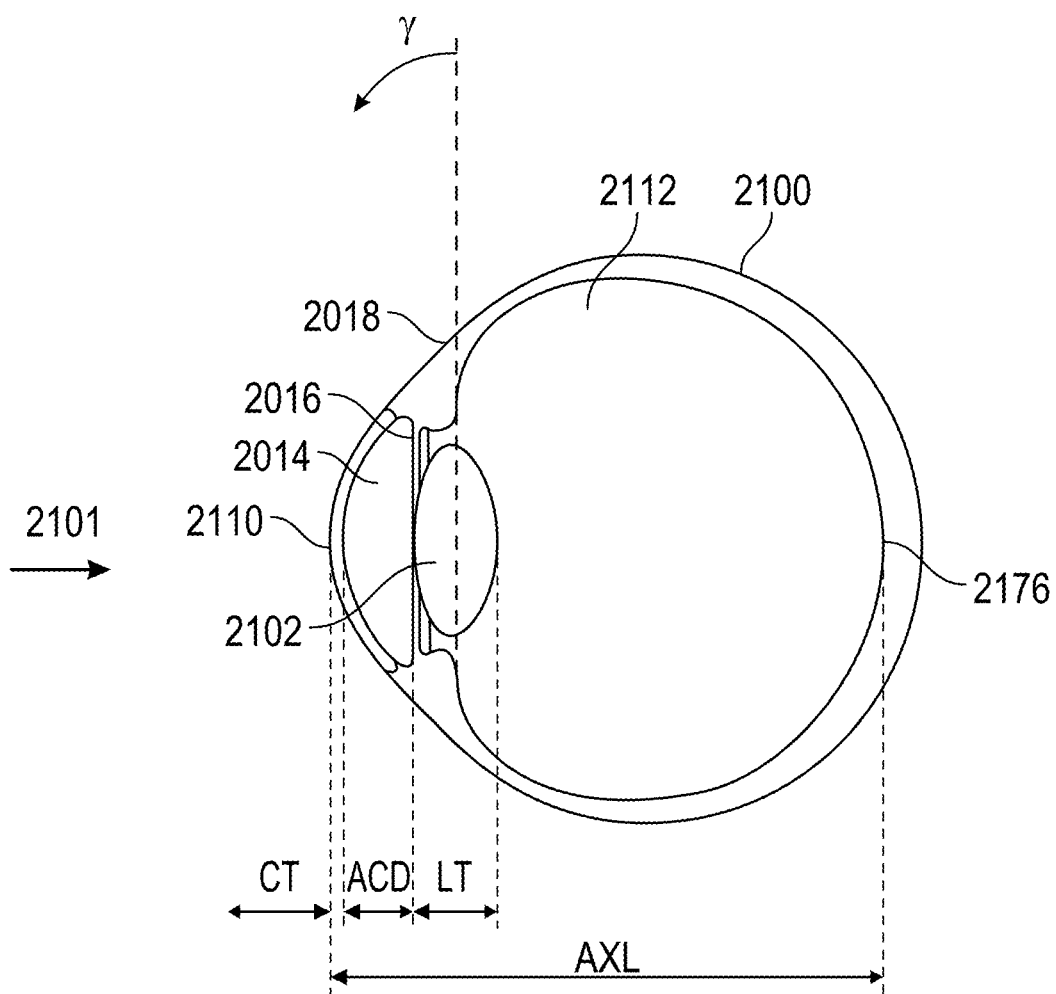
FIG. 21 is a schematic drawing of a human eye.

FIG. 21 is a schematic drawing of a human eye 2100. In many embodiments, a light beam 2101 from a light source enters the eye from the left of FIG. 21, refracts into the cornea 2110, passes through the anterior chamber 2104, the iris 2106 through the pupil, and reaches lens 2102. After refracting into the lens, light passes through the vitreous chamber 2112, and strikes the retina 2176, which detects the light and converts it to an electric signal transmitted through the optic nerve to the brain (not shown). The vitreous chamber 2112 contains the vitreous humor, a clear liquid disposed between the lens 2102 and retina 2176. As indicated in FIG. 21, cornea 2110 has corneal thickness (CT), here considered as the distance between the anterior and posterior surfaces of the cornea. Anterior chamber 2104 has anterior chamber depth (ACD), which is the distance between the anterior surface of the cornea and the anterior surface of the lens. Lens 2102 has lens thickness (LT) which is the distance between the anterior and posterior surfaces of the lens. The eye has an axial length (AXL) which is the distance between the anterior surface of the cornea and the retina 2176. F 1G. 21 also illustrates that, in many subjects the lens, including the lens capsule, may be tilted at one or more angles relative to the optical axis, including an angle γ relative to the optical axis of the eye.

The optical system may also be arranged so that the movement pattern of the scan mirrors provides a lateral motion across the retina so that the shape of the retina may be determined. It is of particular interested to measure the shape and location of the depressed region of the retina named the foveal pit. When the patient is looking directly into the instrument, with their line of sight aligned to the fixation target, the foveal pit will be in center of the OCT lateral scan. This information is beneficial in that it informs the instrument operator if the patient was looking directly at the target when the measurement was made. Retinal scans are also useful in detecting disease conditions. In some cases there may be an absence of a foveal pit that also is considered an indication of a corneal abnormality.

The average axial length of the adult human eye is about 24 mm. Since the full range imaging depth of the OCT measurements are only about 5 mm to 8 mm, then OCT scanning of the present invention preferably provides for OCT scans at different depths of the eye that can be combined together to form a combined OCT image of the eye. The OCT measurements of the present invention preferably includes OCT imaging at various depths of the patient's eye for imaging 1) at least a portion of the retina, 2) at least a portion of the anterior portion of the eye, including at least a portion of the cornea (anterior and posterior), iris, and lens (anterior and posterior), and 3) performing axial eye length measurements.

Figure 22A:
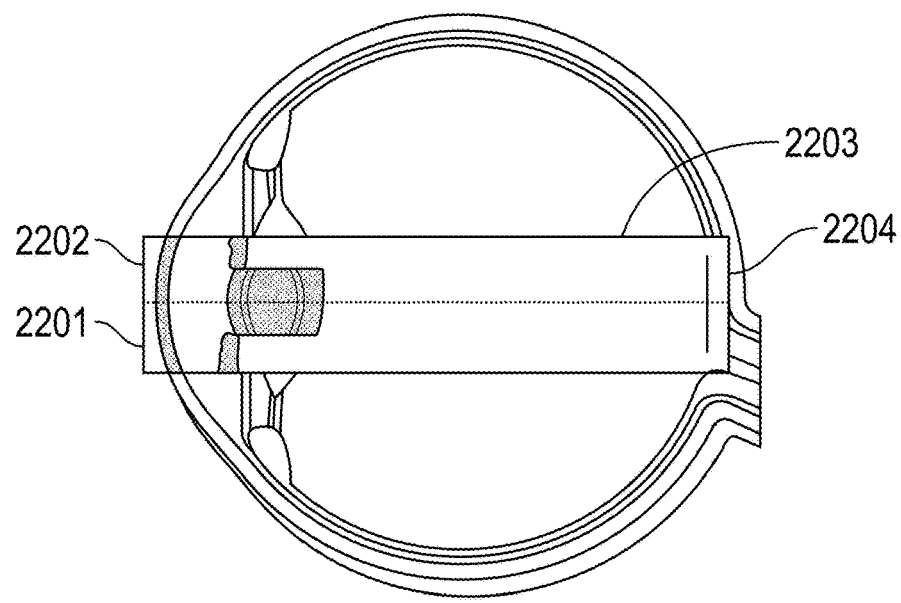
FIG. 22A illustrates a preferred scanning region for the OCT subsystem according to many embodiments of the present invention.
Figure 22B:
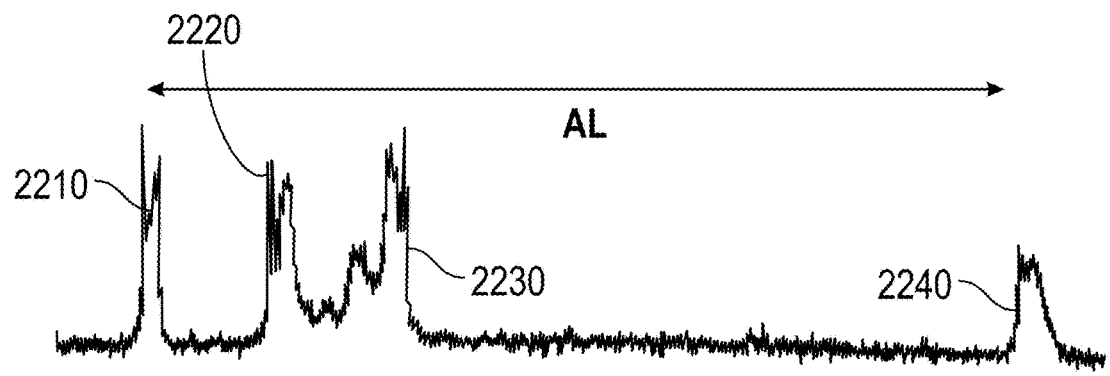
FIG. 22B shows a representative graph of an intensity of an OCT signal of an OCT subsystem 190 according to many embodiments as a function of depth along the axis defining the axial length of the eye.
Figure 22C:
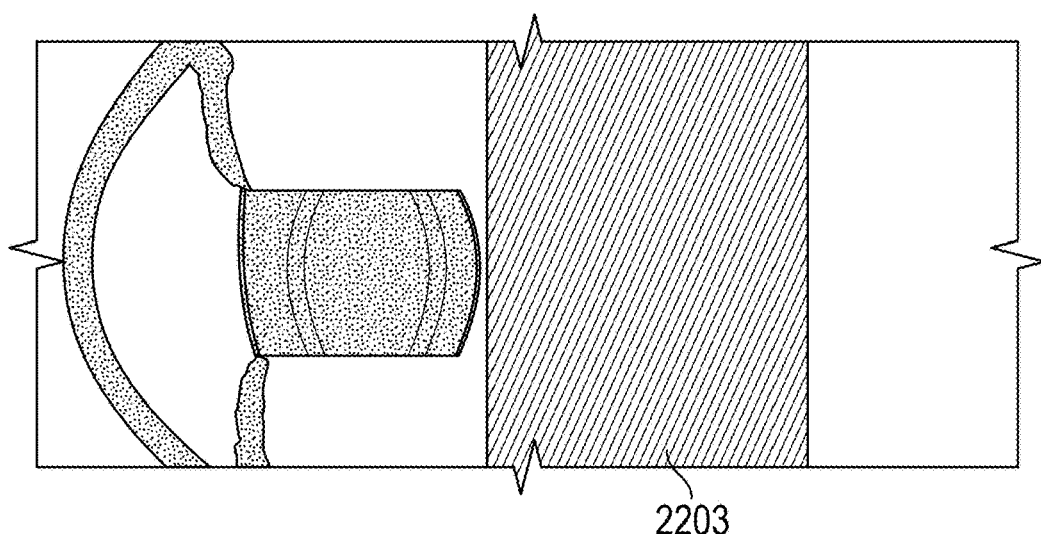
FIG. 22C shows a cross-section of an eye obtained by an optical measurement system of the present invention using an OCT subsystem according to the present invention

FIGS. 22A-22C illustrate various aspects of the OCT subsystem 1990 according to various aspects of the present invention. FIG. 22A illustrates a preferred scanning region for the OCT subsystem according to many embodiments of the present invention. The scanning region may be defined from starting point 2201 to ending point 2202 at the anterior portion of the eye extending in a direction transverse the direction of propagation of the OCT beam and also extending in a direction parallel to an axis defining the axial length of the eye to the posterior portion 2204 of the eye. The lateral scanning region should generally be sufficiently large in the lateral direction to permit imaging of the central portion of the cornea, at least a portion of the iris, at least a portion of the lens and at least of the retina. It should be noted that a region 303 between the posterior portion of the lens and the surface of the retina may optionally not be scanned by OCT subsystem 1990 because the portion 2230 does not contain anatomical structure for 3D analysis.

FIG. 22B shows a representative graph of an intensity of an OCT signal of an OCT subsystem 1990 according to many embodiments as a function of depth along the axis defining the axial length of the eye. The graph generally exhibits approximately four peaks having a complex structure: (1) a peak 2210 having a doublet-like structure and generally corresponding to a location of the cornea; (2) a peak 2220 having a doublet-like structure and generally corresponding to a location of an anterior surface of the lens; (3) a peak 2230 having a complex structure generally corresponding to a location of a posterior surface of the lens; and (4) a peak 2240 generally corresponding to a location of a retina. A distance between peak 310 and peak 2240 can be used to calculate the axial length (AL) of the eye. Preferably, an OCT scan by OCT subsystem 1990, including both an A-scan and B-scan, is conducted at least one location in the anterior portion of the eye (e.g., a location of a cornea, a location of an anterior surface of a lens and/or a location of a posterior surface of the lens) and at least one location in the posterior portion of the eye (e.g., at a location of a retina). In some embodiments, an OCT scan by the OCT subsystem 1990, including both an A-Scan and a B-scan is performed at a location corresponding to each of a location of the cornea, a location of an anterior surface of the lens, a location of a posterior surface of the lens, and a location corresponding to a retina.

It should be noted that because the OCT subsystem 1990 provides for the detection of various structures of the eye, including a location of the cornea, the OCT subsystem 1990 may be used as a ranging system to precisely align the patient in relation to the optical measurement system 1 of the present invention. The use of the OCT as a ranging system can significantly improve accuracy of corneal topography measurements, including keratometry measurements, which are sensitive to misalignment of the corneal structures.

FIG. 22C shows a cross-section of an eye obtained by an optical measurement system of the present invention using an OCT subsystem according to the present invention.

Figure 23:
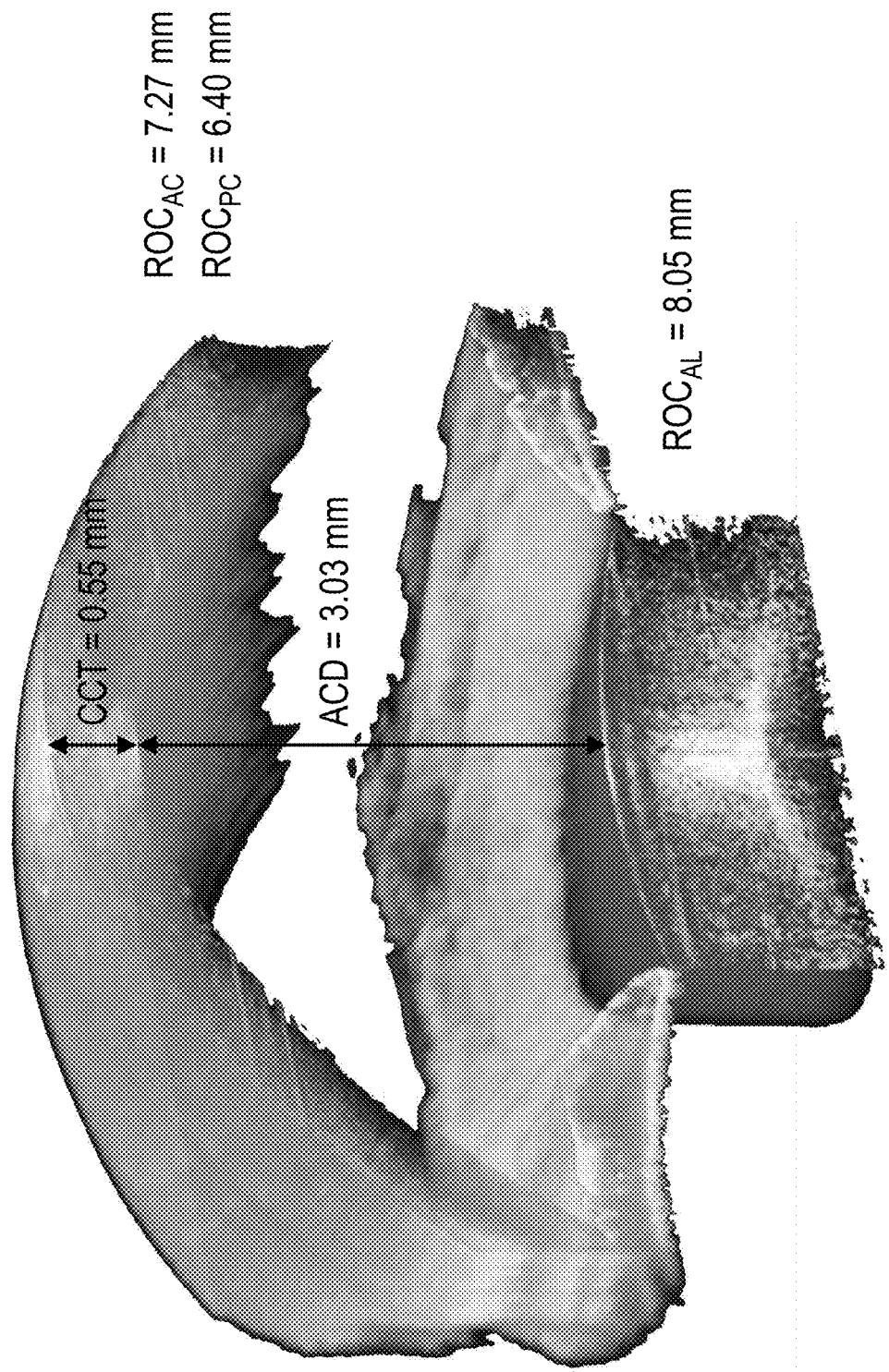
FIG. 23 is a 3-dimensional representation of an anterior portion of an eye obtained using the optical measurement system according to many embodiments.

FIG. 23 shows a 3 dimensional view of an eye obtained by an optical measurement system of the present invention using an OCT subsystem according to the present invention. FIG. 23 evidences that the OCT subsystem of the present invention is operable to obtain biometry measurements according to the present invention, including the central corneal thickness (CCT), the anterior chamber depth (ACD), the radius of curvature of the anterior cornea (ROCAC), the radius of curvature of the Posterior cornea (ROCPC) and the Radius of curvature of the axial length (ROCAL).

Preferably, the OCT subsystem 1990 provides sufficiently resolved structural information to provide a structural assessment that may provide a user with an indication of suitability of a particular patient for a laser cataract procedure. In one embodiment, an OCT scan performed by the OCT subsystem 1990 at or near the retina (i.e., a retina scan) is sufficiently resolved to identify the foveal pit location and depth, wherein a lack of depression indicates an unhealthy retina.

In another embodiment, the optical measurement instrument 1801 of the present invention provides one or more measurements sufficient to provide an assessment of the tear film of a patient. In one embodiment, the tear film assessment comprises a comparison of a wavefront aberrometry map and a corneal topography map or OCT map of the patient's eye, by, for instance, subtracting the corneal topography map from the wavefront aberrometry map, to obtain a difference map. A determination of whether the tear film is broken (if not smooth); an assessment of the tear film, including tear film breakup, can be obtained by reviewing the shape of spots on the topographer. For instance, a finding or indication that the tear film is disrupted, or broken, may be based upon the shape of a spot in that, if the spots are not round, and have, for instance, an oblong or broken up shape, it indicates that tear film is disrupted. The existence of such a disrupted tear film may indicate that K value, and other ocular measurements may not be reliable In operation, as shown in FIG. 20, after exiting connector 2012, the OCT beam 2014 is collimated, preferably using a collimating optical fiber 1996. Following collimating fiber 1996 the OCT beam 2014 is directed to an z-scan device 1993 operable to change the focal point of the OCT beam in a z-direction, and x- and y-scan devices 1995 and 1997, which are operable to scan the OCT beam in x and y-directions perpendicular to the z-direction.

Following the collimating optical fiber 1996, the OCT beam 2014 continues through a X-scan device 1993, 1994. Preferably, the z-scan device is a Z-telescope 1993, which is operable to scan focus position of the OCT beam 2014 in the patient's eye 1901 along the Z axis. For example, the Z-telescope 1993 can include a Galilean telescope with two lens groups (each lens group includes one or more lenses). One of the lens groups moves along the Z axis about the collimation position of the Z-telescope 1993. In this way, the focus position in the patient's eye 1901 moves along the Z axis. In general, there is a relationship between the motion of lens group and the motion of the focus point. The exact relationship between the motion of the lens and the motion of the focus in the z axis of the eye coordinate system does not have to be a fixed linear relationship. The motion can be nonlinear and directed via a model or a calibration from measurement or a combination of both. Alternatively, the other lens group can be moved along the Z axis to adjust the position of the focus point along the Z axis. The Z-telescope 1993 functions as a z-scan device for changing the focus point of the OCT beam 2014 in the patient's eye 1901. The Z-scan device can be controlled automatically and dynamically by the controller 1860 and selected to be independent or to interplay with the X and Y scan devices described next.

After passing through the z-scan device, the OCT beam 2014 is incident upon an X-scan device 1995, which is operable to scan the OCT beam 2014 in the X direction, which is dominantly transverse to the Z axis and transverse to the direction of propagation of the OCT beam 2014. The X-scan device 1995 is controlled by the controller 60, and can include suitable components, such as a lens coupled to a MEMS device, a motor, galvanometer, or any other well-known optic moving device. The relationship of the motion of the beam as a function of the motion of the X actuator does not have to be fixed or linear. Modeling or calibrated measurement of the relationship or a combination of both can be determined and used to direct the location of the beam.

After being directed by the X-scan device 1995, the OCT beam 2014 is incident upon a Y scan device 1997, which is operable to scan the OCT beam 2014 in the Y direction, which is dominantly transverse to the X and Z axes. The Y-scan device 1997 is controlled by the controller 1860, and can include suitable components, such as a lens coupled to a MEMS device, motor, galvanometer, or any other well-known optic moving device. The relationship of the motion of the beam as a function of the motion of the Y actuator does not have to be fixed or linear. Modeling or calibrated measurement of the relationship or a combination of both can be determined and used to direct the location of the beam. Alternatively, the functionality of the X-Scan device 1995 and the Y-Scan device 1997 can be provided by an XY-scan device configured to scan the OCT beam 2014 in two dimensions transverse to the Z axis and the propagation direction of OCT beam 2014. The X-scan and Y scan devices 1995, 1997 change the resulting direction of the OCT beam 2014, causing lateral displacements of OCT beam 2014 located in the patient's eye 1901.

The OCT sample beam 2014 is then directed to beamsplitter 1973 through lens 1975 through quarter wave plate 1971 and aperture 1914 and to the patient eye 1901. Reflections and scatter off of structures within the eye provide return beams that retrace back through the patient interface quarter wave plate 1971, lens 175, beamsplitter 1973, y-scan device 1997, x-scan device 1995, z-scan device 1993, optical fiber 1996 and beam combiner 2004 (FIG. 20), and back into the OCT detection device 2020. The returning back reflections of the sample arm 201 are combined with the returning reference portion 2006 and directed into the detector portion of the OCT detection device 2020, which generates OCT signals in response to the combined returning beams. The generated OCT signals that are in turn interpreted by the controller 1860 to determine the spatial disposition of the structures of interest in the patient's eye 1901. The generated OCT signals can also be interpreted by the controller to measure to determine the spatial disposition of the structures of interest in the patient's eye 1901. The generated OCT signals can also be interpreted by the control electronics to align the position and orientation of the patient eye within the patient interface.

The optical measurement systems according to the present invention preferably comprise an iris imaging subsystem 40. The imaging subsystem 1840 generally comprises an infrared light source, preferably infrared light source 1952, and detector 1941. In operation light from the light source 1952 is directed along second optical path 1960 to first optical path 1970 and is subsequently directed to eye 1901 as described above. Light reflected from the iris of eye 1901 is reflected back along first optical path 1970 to detector 1941. In normal use, an operator will adjust a position or alignment of assembly 1900 in X, Y and Z directions to align the patient according to the image detector array 1941. In one embodiment of the iris imaging subsystem, eye 1901 is illuminated with infrared light from light source 1952. In this way, the wavefront obtained by wavefront sensor 1955 will be registered to the image from detector array 1941.

The image that the operator sees is the iris of eye 1901. The cornea generally magnifies and slightly displaces the image from the physical location of the iris. So the alignment that is done is actually to the entrance pupil of the eye. This is generally the desired condition for wavefront sensing and iris registration.

Iris images obtained by the iris imaging subsystem may be used for registering and/or fusing the multiple data sets obtained by the various subsystems of the present invention, by methods described for instance in "Method for registering multiple data sets," U.S. patent application Ser. No. 12/418,841, which is incorporated herein by reference. As set forth in application Ser. No. 12/418,841, wavefront aberrometry may be fused with corneal topography, optical coherence tomography and wavefront, optical coherence tomography and topography, pachymetry and wavefront, etc. For instance, with image recognition techniques it is possible to find the position and extent of various features in an image. Regarding iris registration images, features that are available include the position, size and shape of the pupil, the position, size and shape of the outer iris boundary (OIB), salient iris features (landmarks) and other features as are determined to be needed. Using these techniques, both patient movement between measurements (and/or during a measurement sequence) can be identified, as well as changes in the eye itself (including those induced by the measurement, such as changes in the size of the pupil, changes in pupil location, etc.).

In many embodiments, an optical measurement system according to the present includes a target fixation subsystem 1850 (FIG. 18), and an assembly 1900 shown in FIGS. 19A and 19B includes a fixation target subsystem 1980 which includes a fixation target 1982 for the patient to view. Fixation target subsystem 1980 is used to control the patient's accommodation, because it is often desired to measure the refraction and wavefront aberrations when eye 1901 is focused at its far point (e.g., because LASIK treatments are primarily based on this). In the target fixation subsystem, a projection of a target, for instance a cross-hair pattern is projected onto the eye of the patient, the cross hair pattern being formed by a backlit LED and a film.

In operation, light originates from the light source 1952 or, alternatively, from video target backlight 1982 and lens 1986. Lens 1985 collects the light and forms an aerial image T2. This aerial image is the one that the patient views. The patient focus is maintained on aerial image 1982 during measurement so as to maintain the eye in a fixed focal position.

The operating sequence, the optical measurement system, and methods of the present invention are not particularly limited. A scan of the patient's eye may comprise one or more of a wavefront aberrometry measurement of a patient's eye utilizing the wavefront aberrometry subsystem, a corneal topography measurement of a patient's eye and an OCT scan of the patient's eye using the OCT subsystem, wherein the OCT scan includes a scan at each or one or more locations within the eye of the patient. These locations of the OCT scan may correspond to the location of the cornea, the location of the anterior portion of the lens, the location of the posterior portion of the lens and the location of the retina. In a preferred embodiment, the operating sequence includes each of a wavefront aberrometry measurement, a corneal topography measurement and an OCT scan, wherein the OCT scan is taken at least at the retina, the cornea and one of anterior portion of the patient's lens. Preferably, an iris image is taken simultaneously with or sequentially with an each of measurements taken with wavefront aberrometry subsystem the corneal topography subsystem and the OCT subsystem, including an iris image take simultaneously with or sequentially with the location of each OCT scan. This results in improved accuracy in the 3-dimensional modeling of the patient's eye by permitting the various data sets to be fused and merged into a 3-dimensional model.

Figure 24:
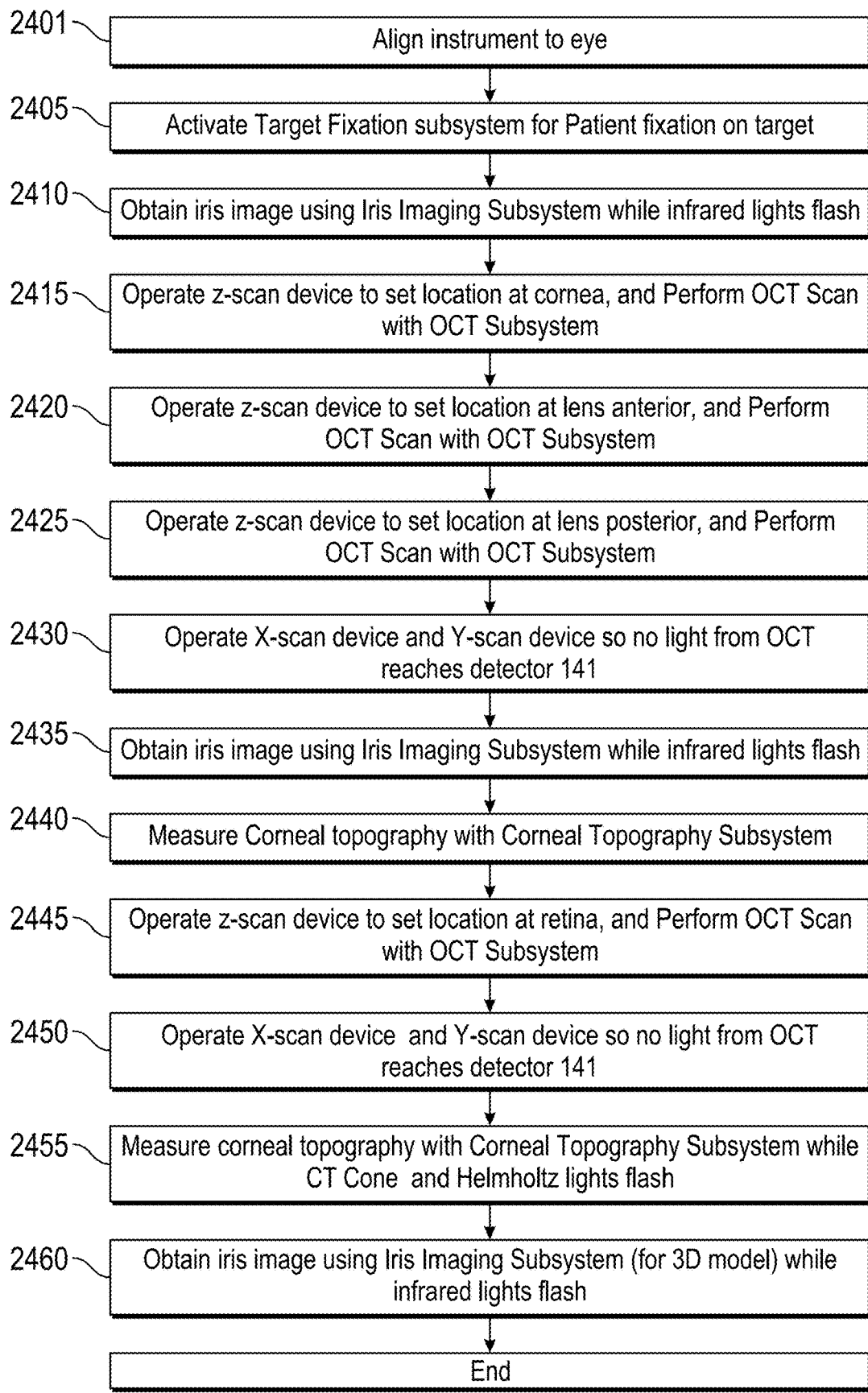
FIG. 24 is a flowchart of an example embodiment of a method for performing cataract diagnostics for an eye with an optical measurement instrument according to one embodiment described herein, including wavefront aberrometry, corneal topography and OCT measurements at various locations with the eye along the axial length of the eye.

FIG. 24 shows one embodiment of an operating sequence and method in which wavefront aberrometry measurements, corneal topography measurements and OCT measurements are all taken. The optical measurement apparatus, including the method of FIG. 24 may be used preoperatively, intra-operatively and/or postoperatively. In the method of FIG. 24, a step 2401 comprises aligning the optical measurement system to the eye of the patent. A step 2405 comprises activating the Target Fixation subsystem for patient fixation on target. A step 2410 comprises activating the wavefront aberrometer subsystem such that the wavefront aberrometer light source 2410 is activated and the eye refraction is measured via the wavefront sensor. A step 2415 comprises activating the target fixation system to move the target to an optimum position and activate the wavefront aberrometer subsystem such that the wavefront aberrometer light source 1952 is activated and the eye refraction is measured via the wavefront sensor 1955. A step 2420 comprises obtaining an iris image using Iris Imaging Subsystem while infrared light source 1952 is operating. A step 2425 comprises operating the z-scan device to set OCT scan location at or near cornea, and performing an OCT Scan with the OCT Subsystem. A step 2430 comprises operating the z-scan device to set the OCT location at a location at or near the lens anterior and performing an OCT Scan with the OCT Subsystem. A step 2435 comprises operating the Z-scan device to set the OCT location at a location at or near the lens posterior and performing an OCT Scan with the OCT Subsystem. A step 2440 comprises operating the X-scan device and Y-scan device so no light from OCT reaches detector 1941. A step 2445 comprises obtaining an iris image using the Iris Imaging Subsystem while the infrared light source 1952 flashes. A step 2450 comprises obtaining an iris image using the Iris Imaging Subsystem while the light sources 1920 and Helmholz source flash. A step 2450 comprises measuring the corneal topography with the Corneal Topography Subsystem. A step 2455 comprises operating the z-scan device to set the OCT location at a location at or near the retina and performing an OCT Scan with the OCT Subsystem. A step 2460 comprises operating the X-scan device and Y-scan device so no light from OCT reaches detector 1941. An optional step 2465 comprises measure corneal topography with a Corneal Topography Subsystem, which may provide for an improved 3D model of the patient eye. An optional step 2470 comprises obtaining an iris image using Iris Imaging Subsystem (for 3D model).

Figure 25:
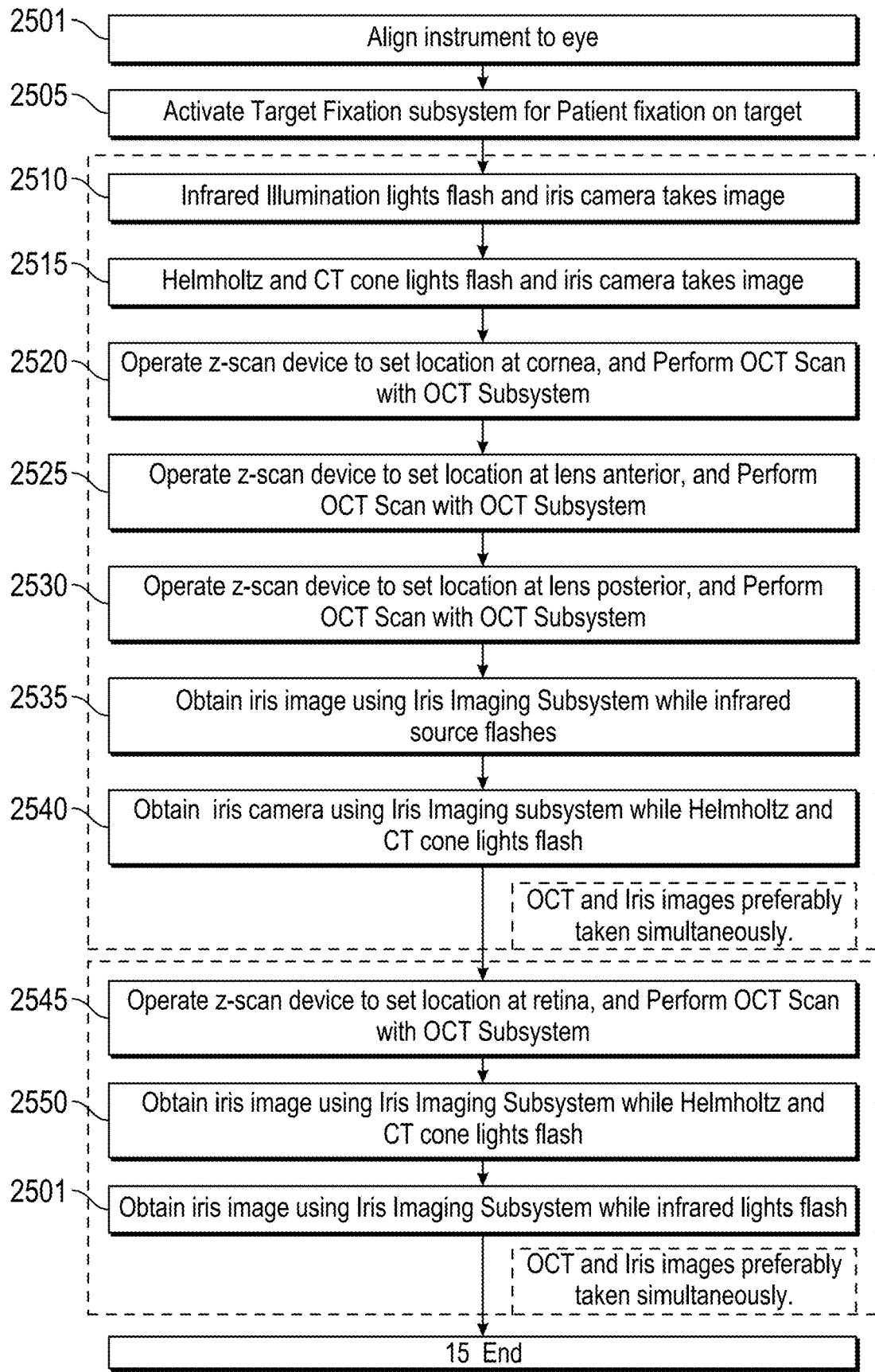
FIG. 25 is a flowchart of another example embodiment of a method for performing cataract diagnostics for an eye with an optical measurement instrument.

FIG. 25 shows one embodiment of an operating sequence and method in which no wavefront aberrometry measurements are taken. The optical measurement apparatus, including the method of FIG. 24 may be used preoperatively, intra-operatively and/or postoperatively. In the embodiment of FIG. 25, a step 2501 comprises aligning the optical measurement system to the eye of the patent. A step 2505 comprises activating the Target Fixation subsystem for patient fixation on target. A step 2510 comprises obtaining an iris image using Iris Imaging Subsystem while infrared light source 1952 is operating. A step 2515 comprises operating the z-scan device to set OCT scan location at or near cornea, and performing an OCT Scan with the OCT Subsystem. A step 2520 comprises operating the Z-scan device to set the OCT location at a location at or near the lens anterior and performing an OCT Scan with the OCT Subsystem. A step 2525 comprises operating z-scan device to set the OCT location at a location at or near the lens posterior and performing an OCT Scan with the OCT Subsystem. A step 2530 comprises operating the X-scan device and Y-scan device so no light from OCT reaches detector 1941. A step 2535 comprises obtaining an iris image using the Iris Imaging Subsystem while the infrared light source 1952 flashes. A step 2540 comprises measuring the corneal topography with the Corneal Topography Subsystem. A step 2545 comprises operating the z-scan device to set the OCT location at a location at or near the retina and performing an OCT Scan with the OCT Subsystem. A step 2550 comprises operating the X-scan device and Y-scan device so no light from OCT reaches detector 141. An optional step 2555 comprises measure corneal topography with Corneal Topography Subsystem, which may provide for an improved 3D model of the patient eye. An optional step 2560 comprises obtaining an iris image using Iris Imaging Subsystem.

Figure 26:
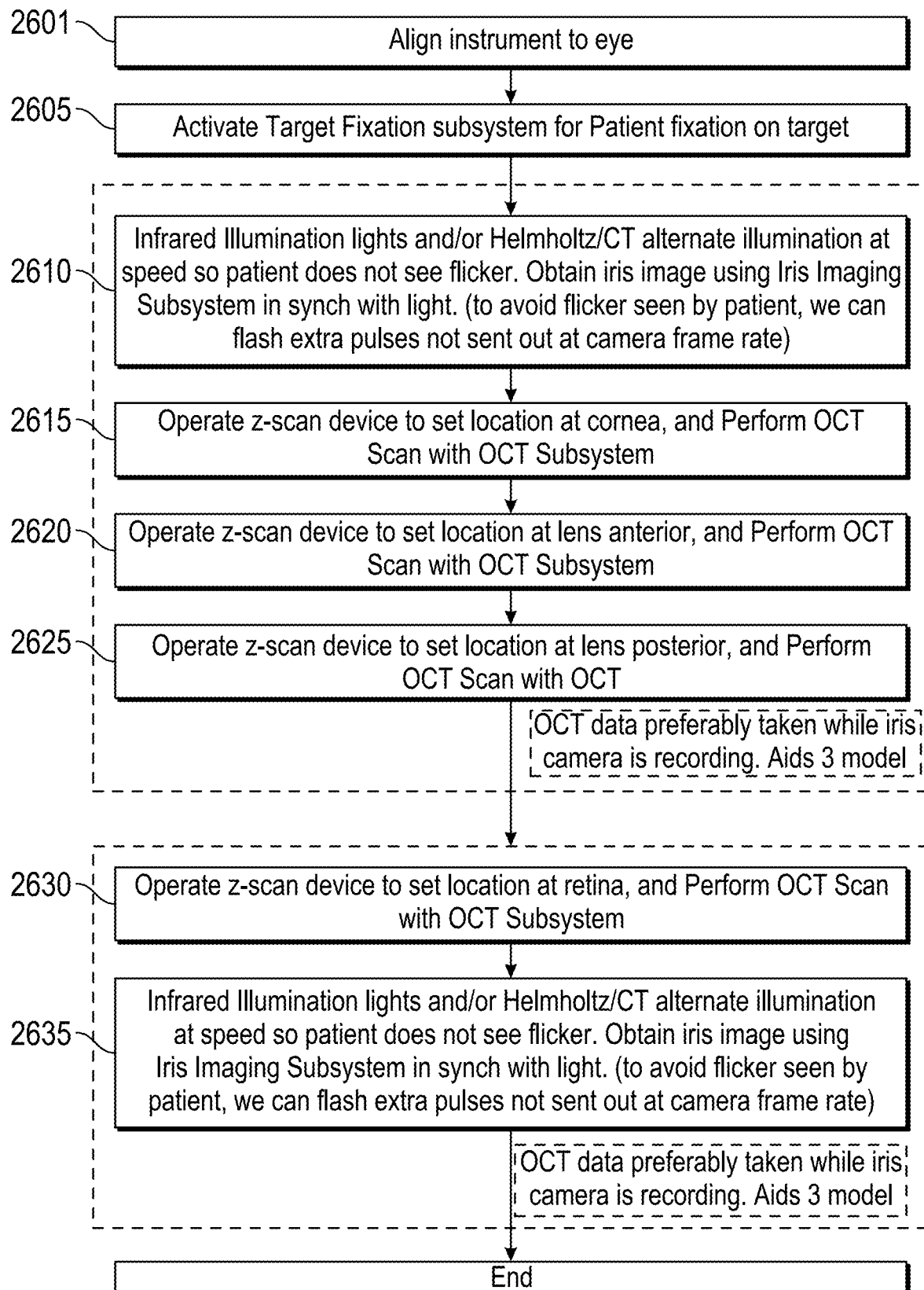
FIG. 26 is a flowchart of another example embodiment of a method for performing cataract diagnostics for an eye with an optical measurement instrument in which OCT measurements and iris imaging may be performed simultaneously.

FIG. 26 shows an embodiment of an operational sequence and method in which OCT measurements utilizing the OCT subsystem and Iris images using the iris imaging subsystem may be taken simultaneously in order to improve three dimensional modeling of the patient's eye and improved iris registration of the measurement data sets. The operational sequence of FIG. 26 may be applied to or incorporated into either of the operational sequences and methods of FIG. 24 or 25 as would be readily understood by those ordinarily skilled. In order to effectuate the operating sequence and method of FIG. 26, a lens is inserted into optical path 170 between beamsplitter 1973 and detector 1941. The inserted lens is selected to preferentially pass infrared light used for iris imaging but to block an OCT beam from the OCT light source from reaching detector 1941. In this configuration, OCT measurements and iris images may be taken simultaneously. Further, in the embodiment of FIG. 26 a regular speed global shutter iris camera is used operating at 12 frames/second. The operating sequence and method of FIG. 10 may be used preoperatively, intra-operatively and/or postoperatively.

In the embodiment of FIG. 26, a step 2601 comprises aligning the optical measurement system to the eye of the patent. A step 2605 comprises activating the Target Fixation subsystem for patient fixation on target. A step 2610 comprises obtaining an iris image using Iris Imaging Subsystem while infrared light source 1952 is operating. A step 2615 comprises obtaining an iris image using Iris Imaging Subsystem while corneal topography light sources 1920 and Helmholz light source 1932 are operating. A step 2620 comprises operating the z-scan device to set OCT scan location at or near cornea, and performing an OCT Scan with the OCT Subsystem. A step 2625 comprises operating the z-scan device to set the OCT location at a location at or near the lens anterior and performing an OCT Scan with the OCT Subsystem. A step 2630 comprises operating z-scan device to set the OCT location at a location at or near the lens posterior and performing an OCT Scan with the OCT Subsystem. A step 2635 comprises obtaining an iris image using Iris Imaging Subsystem while infrared light source 1952 is operating. A step 2640 comprises obtaining an iris image using Iris Imaging Subsystem while corneal topography light sources 1920 and Helmholz light source 1932 are operating. A step 2645 comprises operating the z-scan device to set the OCT location at a location at or near the retina and performing an OCT Scan with the OCT Subsystem. A step 2650 comprises obtaining an iris image using Iris Imaging Subsystem while corneal topography light sources 120 and Helmholz light source 1932 are operating. A step 2655 comprises obtaining an iris image using Iris Imaging Subsystem while infrared light source 1952 is operating.

Figure 27:
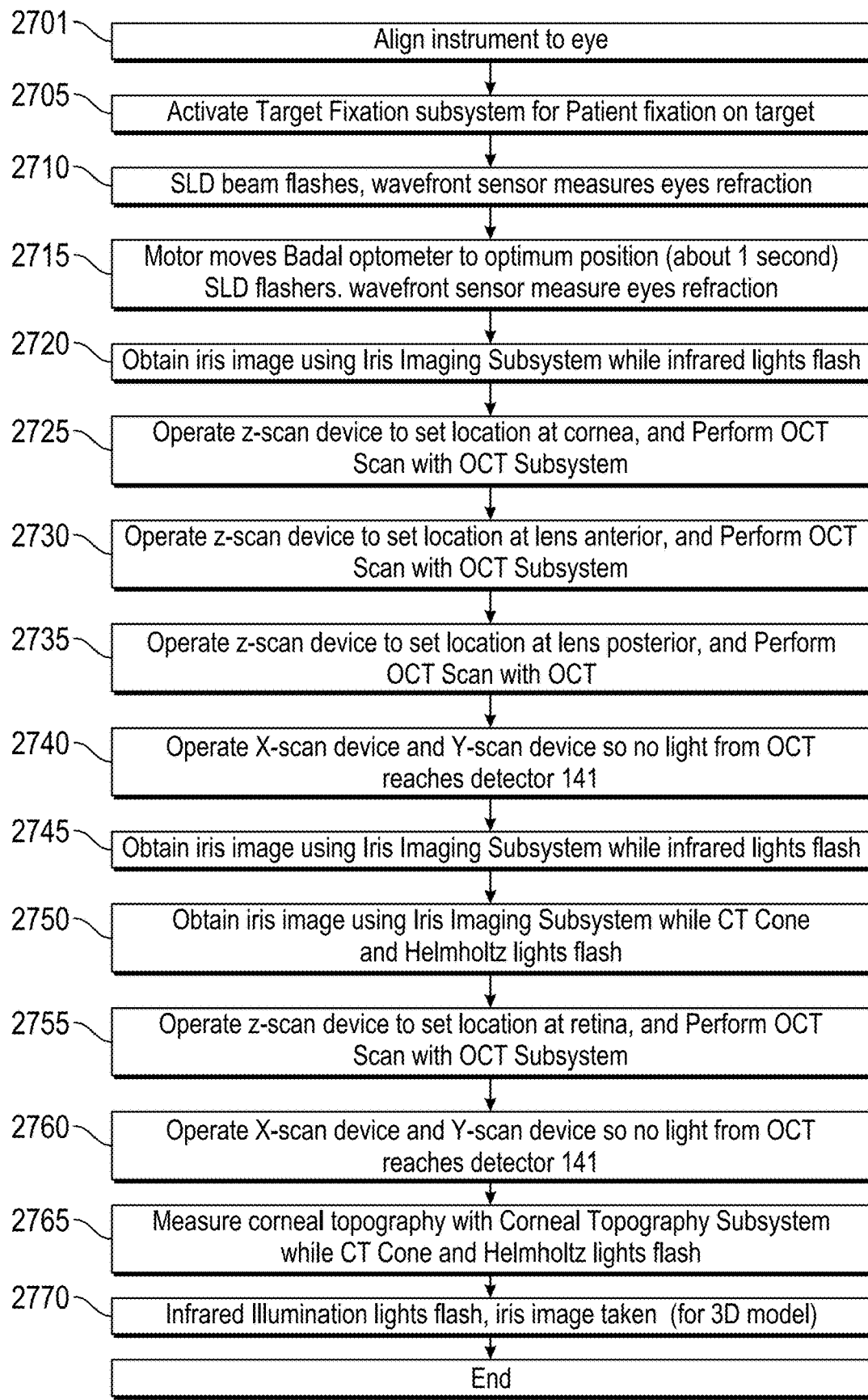
FIG. 27 is a flowchart of yet another example embodiment of a method for performing cataract diagnostics for an eye with an optical measurement instrument in which OCT measurements and iris imaging may be performed simultaneously.

FIG. 27 shows another embodiment of an operational sequence and method in which OCT measurements utilizing the OCT subsystem and Iris images using the iris imaging subsystem may be taken simultaneously in order to improve three dimensional modeling of the patient's eye and improved iris registration of the measurement data sets. The operational sequence of this embodiment may be applied to or incorporated into either of the operational sequence and methods of FIG. 24 or 25 as would be readily understood by those ordinarily skilled. As with the method of FIG. 26, in order to effectuate the operating sequence and method of FIG. 27, a lens is inserted into optical path 1970 between beamsplitter 1973 and detector 1941. The inserted lens is selected to preferentially pass infrared light used for iris imaging but to block an OCT beam from the OCT light source from reaching detector 1941. In this configuration, OCT measurements and iris images may be taken simultaneously. Further, in the embodiment of FIG. 26 a high speed global shutter iris camera, or fast frame rate, is used operating at 60 frames/second. Under the fast frame rate conditions of this embodiment, an infrared illumination source, such as a wavefront aberrometry source, may be used with a one or more second light sources, such as a combination of the corneal topography sources 1920 and the Helmholz source, to alternately illuminate a patient's eye repeatedly at short intervals (i.e., alternative short flashes). Under these conditions, the iris imaging subsystem may be synched to the flash from each source so as to capture iris images under both illumination conditions. The operating sequence and method of FIG. 27 may be used preoperatively, intraoperatively and/or postoperatively.

In the embodiment of FIG. 27, a step 2701 comprises aligning the optical measurement system to the eye of the patient. A step 2705 comprises activating the Target Fixation subsystem for patient fixation on target. A step 2710 comprises obtaining an iris image using Iris Imaging Subsystem while infrared light source 152 is operating and obtaining an iris image using Iris Imaging Subsystem while corneal topography light sources 120 and Helmholz light source 132 are operating. This is done by alternately operating the infrared light source and a combination of the corneal topography/Helmholz light sources so as to alternately illuminate the patient's eye with the infrared light source and the combined light sources, preferably at a rate that a patient's eye cannot resolve the "flicker." In this step, the Iris imaging subsystem is in synch with the respective illuminate lights. A step 2715 comprises operating the z-scan device to set OCT scan location at or near cornea, and performing an OCT Scan with the OCT Subsystem. A step 2720 comprises operating the Z-scan device to set the OCT location at a location at or near the lens anterior and performing an OCT Scan with the OCT Subsystem. A step 2725 comprises operating z-scan device to set the OCT location at a location at or near the lens posterior and performing an OCT Scan with the OCT Subsystem. A step 2730 comprises operating the z-scan device to set the OCT location at a location at or near the retina and performing an OCT Scan with the OCT Subsystem. A step 2735 comprises obtaining an iris image using Iris Imaging Subsystem while infrared light source 1952 is operating and obtaining an iris image using Iris Imaging Subsystem while corneal topography light sources 120 and Helmholz light source 132 are operating as described above for Step 2710.

The optical measurement instrument 1801 and the optical measurements obtained therewith may be used pre-operatively, i.e. before a cataract surgery or other surgical procedure, for, e.g., eye biometry and other measurements, diagnostics and surgical planning Surgical planning may include one or more predictive models. In the one or more predictive models, one or more characteristics of the postoperative condition of the patient's eye or vision is modeled based on one or more selected from the group consisting of pre-operative measurements obtained from the optical measurement instrument 1801, a contemplated surgical intervention, and on or more algorithms or models stored in the memory of the optical measurement system 1 and executed by the processor. The contemplated surgical intervention may include the selection of an IOL for placement, the selection of an IOL characteristic, the nature or type of incision to be used during surgery (e.g., relaxation incision), or one or more post-operative vision characteristics requested by the patient.

The optical measurement instrument 1801 and the optical measurements obtained therewith may be used intra-operatively, i.e., during a cataract surgery or other surgical procedure, for, e.g., intraoperative eye diagnostics, determining IOL placement and position, surgical planning, and control/or of a laser surgical system. For instance, in the case of laser cataract surgical procedure, any measurement data obtained preoperatively by the optical measurement instrument may be transferred to a memory associated with a cataract laser surgical system for use before, during or after either the placement of a capsulotomy, fragmentation or a patient's lens or IOL placement during the cataract surgery. In some embodiments, measurements using optical measurement instrument 1801 may be taken during the surgical procedure to determine whether the IOL is properly placed in the patient's eye. In this regard, conditions measured during the surgical procedure may be compared to a predicted condition of the patient's eye based on pre-operative measurements, and a difference between the predicted condition and the actual measured condition may be used to undertake additional or corrective actions during the cataract surgery or other surgical procedure.

The optical measurement instrument 1801 and the optical measurements obtained therewith may be used postoperatively, i.e., after a cataract surgery or other surgical procedure, for, e.g., post-operative measurement, postoperative eye diagnostics, postoperative IOL placement and position determinations, and corrective treatment planning if necessary. The postoperative testing may occur sufficiently after the surgery that the patient's eye has had sufficient time to heal and the patient's vision has achieved a stable, postsurgical state. A postoperative condition may be compared to one or more predicted condition performed pre-operatively, and a difference between the preoperatively predicted condition and the postoperatively measured condition may be used to plan additional or corrective actions during the cataract surgery or other surgical procedure.

The optical measurement instrument 1801, including the corneal topography subsystem, the OCT subsystem and the wavefront aberrometry subsystem, utilizing a suitable operating sequence as disclosed herein, is operable to measure one, more than one or all of the following: ocular biometry information, anterior corneal surface information, posterior corneal surface information, anterior lens surface information, posterior lens surface information, lens tilt information, lens position information, and intra-ocular lens surface and thickness information in cases where an intraocular lens was previously implanted. In some embodiments, the ocular biometry information may include a plurality of central corneal thicknesses (CCT), an anterior chamber depth (ACT), a pupil diameter (PD), a white to white distance (WTW), a lens thickness (LT), an axial length (AL) and a retinal layer thickness. This measurement data may be stored in memory 1862 associated with controller 1860. The plurality of characteristics may be measured preoperatively, and where appropriate, intra-operatively, and postoperatively.

In many embodiments, memory 1862 associated with controller 1860 may store intraocular lens (IOL) model data for a plurality of IOL models, each of the IOL models having associated with it a plurality of predetermined parameters selected from the group consisting of dioptic power, refractive index, asphericity, toricity, haptic angulation and lens filter. The IOL data may be used by one or more processors of optical measurement instrument 1801, in conjunction with measurement data of a subject's eye obtained by optical measurement instrument 1801, for cataract diagnostics or cataract treatment planning, which may include specifying and/or selecting a particular IOL for a subject's eye. For example, one or more processors of optical measurement instrument 1801 may execute an algorithm which includes: accessing the plurality of IOL models stored in, and for each of the IOL models: (1) modeling the subject's eye with an intraocular lens corresponding to the IOL model and the measured characteristics of the subject's eye; (2) simulating the subject's eye based on the plurality of IOL predetermined parameters and the predicted IOL position; (3) performing one of a ray tracing and a power calculation based on said model of the subject's eye; and (4) selecting an IOL for the subject's eye from the plurality of IOL models corresponding to the optimized IOL based on a predetermined criteria.

In many embodiments, one or more processors of optical measurement instrument 1801 may execute an algorithm comprising: determining a desired postoperative condition of the subject's eye; empirically calculating a post-operative condition of the eye based at least partially on the measured eye characteristics; and predictively estimating, in accordance with an output of said empirically calculating and the eye characteristics, at least one parameter of an intraocular lens for implantation into the subject's eye to obtain the desired postoperative condition.

In many embodiments, the eye imaging and measurement system further comprises a memory operable to store Intraocular Lens ("IOL") Data, the IOL Data including a plurality of dioptic power, anterior and posterior radius, IOL thickness, refractive index, asphericity, toricity, echelette features, haptic angulation and lens filter.

In many embodiments, the eye imaging and measurement system further comprises a memory operable to store intraocular lens ("IOL") model data for a plurality of IOL models, IOL model having associated with a plurality of predetermined parameters selected from the group consisting of dioptic power, anterior and posterior radius, IOL thickness, refractive index, asphericity, toricity, echelette features, haptic angulation and lens filter.

In many embodiments, methods such as those described above with respect to FIGS. 10 and 12-15 may be performed with optical measurement instrument 1801 (for example including assembly 1900) with respect to cataract surgery, in particular the selection and placement of an intraocular lens (IOL) for implantation into the subject's eye to obtain the desired postoperative condition. In that case, in some embodiments the pre-treatment vectors may be replaced by pre-surgery vectors, the post-treatment vectors may be replaced by post-surgery vectors, and the effective treatment vector functions may be replaced by effective surgery vector functions. In some embodiments, such methods may be applied to a patient's eye which has previously undergone one or more refractive treatments, for example via laser surgery.

For example in some embodiments, measurement of one or more pre-surgery values for various parameters of a patient's eye may be combined with pre-surgery eye data (e.g., including high order aberrations) and post-surgery eye data measured (e.g., by optical measurement instrument 1801) from previous cataract surgeries to derive one or more parameters of an IOL to be implanted into the patient's eye during a subsequent cataract surgery on the patient's eye in order to better achieve a desired outcome, which may be defined in terms of an intended refractive correction vector (IRC), as discussed above. In particular, in some embodiments optical measurement instrument 1801 may be used to perform a method for planning a cataract surgery on an eye of a patient, the method comprising: determining an effective treatment vector function based on a plurality of prior corrective surgeries by: for each prior corrective surgery on an associated eye: defining a pre-surgery vector characterizing measured pre-surgery high-order aberrations of the associated eye; defining a post-surgery vector characterizing measured post-surgery high-order aberrations of the associated eye; deriving the effective surgery vector function using a correlation between the pre-surgery vectors and the post-surgery vectors; defining an input vector based on measured pre-surgery high-order aberrations of the eye of the patient; and deriving one or more parameters of an intraocular lens (IOL) to be implanted into the eye of the patient by applying the effective surgery vector function to the input vector. In some embodiments, the parameters of the IOL may include a power of the IOL and a location within patient's eye where the IOL is to be located. In some embodiments, one or more parameters of an IOL which would be selected based only on measured characteristics of an eye into it is to be implanted are modified based on the results of previous cataract surgeries by taking into consideration the measured pre-surgery and post-surgery characteristics of the eyes on which the previous cataract surgeries were performed. For example, if a number of cataract surgeries were performed previously on eyes having the same or nearly the same measured characteristics as an eye for which a cataract surgery is to be performed, the systems and methods described herein allow the results of those previous cataract surgeries to be taken into account when selecting an IOL to be implanted and a location in the eye for the IOL to be positioned, in order to improve the outcome of the cataract surgery to more closely achieve a desired outcome (e.g., a target refraction of the eye). In some embodiments, the results of previous cataract surgeries may be defined in terms of differences between intended refractive correction vectors (IRCs) of the associated eyes and the surgically induced refractive correction vectors (SIRCs) of the associated eyes.

In some embodiments, the methods such as those described above with respect to FIGS. 10 and 12-15 may be performed with optical measurement instrument 1801 (for example including assembly 1900) with respect to a patient's eye where an IOL has previously been implanted, and where it is now desired to plan and perform a refractive treatment of the eye, for example via laser surgery. In some embodiments, optical measurement instrument 1801 may define an input vector based on pre-surgery characteristics of the eye of the patient which includes an implanted IOL which are measured by measurement instrument 1801, and may derive an effective treatment vector function using a correlation between the pre-treatment vectors and the post-treatment vectors for each of a plurality of prior eye treatments. In some embodiments, the set of prior eye treatments may be limited to treatments of eyes which had an IOL previously implanted.

Embodiments of the present invention further encompass systems and methods for collecting, storing, analyzing, and transmitting information related to pre-operative and post-operative parameters. For example, when a physician or operator performs pre-operative and/or post-operative measurements of a patient at the doctor's office or hospital, such information can be transmitted to a computer system. A processor of the computer system may be configured to analyze that information and build a nomogram for the physician. Similarly, information from a plurality of physicians or information from a plurality of patients can be provided to an analyzed by the computer processor. The computer process may also be configured to determine influence matrices, effective treatment vector functions, and/or patient-specific treatment parameters using the techniques described elsewhere herein. In some cases, it may be possible to selectively chose which parameters are used when determining the influence matrices, effective treatment vector functions, and/or patient-specific treatment parameters. For example, a particular physician may wish to determine a patient treatment parameter without using data associated with a particular parameter. Likewise, a physician may wish to use only data that is associated with a particular range of values for a particular parameter (e.g. selecting data only for eyes that are treated in a dry climate). In some cases, physicians may obtain treatment output from the computer system, and adjust that treatment output before providing the patient with the treatment. Optionally, such adjustments may be transmitted to the computer system for additional analysis. Further optionally, treatment information provided by the computer may be based on or factor in such adjustments. In some cases, techniques may include providing a physician with a predicted outcome based on a suggested treatment, and the physician may compare that predicted outcome with the actual outcome obtained. Hence, techniques may involve obtaining measured pre-treatment and/or post-treatment optical properties of an associated eye, or other related parameters as discussed elsewhere herein, optionally obtained from database, such as a database located in a doctor office, hospital, or some other centralized location (optionally networked with multiple doctor office and/or hospital databases or computer systems). In some instance, embodiments encompass techniques for tracking recommended procedures as well as procedures eventually performed based on recommended procedures, for comparing or analyzing such recommended and performed procedures, for archiving such recommended and performed procedures (and their comparisons), and for adjusting recommendations based on the comparisons.

With regard to arcuate corneal surgeries, incisions can be used to relax corneal astigmatism, and related techniques can be used in IOL surgery. For example, a surgeon may place the corneal incision on the steep axis of the cornea to relax the corneal astigmatism and reduce the need for toric IOLs in patients with less than 1 Diopter of astigmatism. In some cases, the preoperative astigmatism magnitude and axis, the number, angular arc and radial position of incision(s) relative to the optical zone, and age can be considered as parameters for this type of surgery. Use of femtosecond (FS) lasers in arcuate surgery can increase the precision with which the incisions can be made and may result in better outcomes for patients. In addition, FS lasers can be applied to correct corneal astigmatism following corneal transplants. As in the case of other refractive surgeries, it is possible to apply the techniques described herein to improve patient outcomes by using historical outcome data. In the case of arcuate surgery, it is possible to use the parameters noted above (e.g. preoperative astigmatism magnitude and axis, the number, angular arc and radial position of incision(s) relative to the optical zone, and age) in a pre-operative vector. More advanced predictive modeling may include corneal topography based keratometry values, pachymetry and corneal hydration when available to improve the model accuracy. The case of FS arcuate laser surgery may add other options to the incision characteristics as well. These may include partial incisions that don't perforate or break the surface of the cornea, profiled incisions rather than purely normal to the cornea, and incisions other than straight lines and circular arcs (e.g. undulating wave-like or squiggly lines). In some cases, techniques may include completely intrastromal incisions or disruptions. In some cases, techniques may include incisions or disruptions which reach a corneal surface. In some cases, the parameters describing the details of the incision and preoperative parameters may be included in the pre-operative vector.

All patents, patent applications, journal articles, technical references, and the like mentioned herein are hereby incorporated herein by reference for all purposes.

Different arrangements of the components depicted in the drawings or described above, as well as components and steps not shown or described are possible. Similarly, some features and sub combinations are useful and may be employed without reference to other features and sub combinations. Embodiments of the invention have been described for illustrative and not restrictive purposes, and alternative embodiments will become apparent to readers of this patent. Accordingly, the present invention is not limited to the embodiments described above or depicted in the drawings, and various embodiments and modifications can be made without departing from the scope of the claims below.

While the exemplary embodiments have been described in some detail for clarity of understanding and by way of example, a number of adaptations, changes, and modifications will be obvious to those of skill in the art. Hence, the scope of the present invention is solely limited by the claims associated herewith.

What is claimed is:
1. A system, comprising:
    a wavefront measurement device configured to measure pre-surgery values for at least some high order aberra- tions of an eye of a current patient, wherein the at least some high order aberrations have an order greater than two;

an optical coherence tomographer (OCT) configured to measure a value for at least one parameter of the eye of the current patient;

a pupil retroreflector illuminator configured to direct a disc shaped pattern of light to the eye of the current patient;

a processor coupled to the wavefront measurement device and the OCT, the processor having an input configured to receive an effective surgery vector function which minimizes differences between: (1) sets of intended refractive corrections to be applied to eyes of previous patients, and (2) sets of measured surgically induced refractive corrections for the eyes of previous patients as a result of previous surgeries, wherein the processor is configured to:
  establish a set of target post-surgery values for the at least some high order aberrations of the eye of the current patient which have an order greater than two;
  determine a set of intended refractive corrections to be applied to the eye of the current patient as differences between the target post-surgery values for the at least some high order aberrations of the eye of the current patient which have an order greater than two and the pre-surgery values for the at least some high order aberrations of the eye of the current patient which have an order greater than two, using the measured pre-surgery values for the at least some high order aberrations of the eye of the current patient and the value for the at least parameter of the eye of the current patient measured by the OCT, wherein the set of intended refractive corrections to be applied to the eye of the current patient include intended refractive corrections to the at least some high order aberrations of the eye of the current patient which have an order greater than two;
  apply the effective surgery vector function, physician adjustments, chromatic corrections, and cosine corrections to the intended refractive corrections to be applied to the eye of the current patient, to produce a set of adjusted intended refractive corrections to be applied to the eye of the current patient, including adjusted values for the intended refractive corrections to the at least some high order aberrations of the eye of the current patient which have an order greater than two; and
  select one or more parameters of an intraocular lens (IOL) to be implanted into the eye of the current patient, based on the set of adjusted intended refractive corrections to be applied to the eye so as to transform the eye of the current patient to exhibit the target post-surgery values for the at least some high order aberrations of the eye of the current patient which have an order greater than two, wherein the selected one or more parameters of the IOL to be implanted into the eye of the current patient include a selected optical power of the IOL and a selected location in the eye of the current patient where the IOL is to be implanted;

a custom IOL lens fabrication system for receiving the one or more parameters of the IOL to be implanted into the eye of the current patient, and in response thereto fabricating a custom IOL satisfying the one or more parameters so as to transform the eye of the current patient to exhibit the target post-surgery values for the at least some high order aberrations of the eye of the current patient which have an order greater than two; and a detector configured to detect reflected light from the disc shaped pattern of light, reflected by the IOL implanted into the eye of the current patient, to determine if edges of the IOL are decentered and to determine if the IOL unfolded properly when the IOL was implanted into the eye of the current patient.

2. The system of claim 1, wherein a plurality of values of the set of adjusted intended refractive corrections to be applied to the eye of the current patient are each altered by a plurality of values of the effective surgery vector function.

3. The system of claim 1, wherein the processor is further configured to control the wavefront measurement device to measure a set of post-surgery values for the at least some high order aberrations of the eye of the current patient after implantation of the IOL, having the selected one or more parameters, into the eye of the current patient and the processor produces therefrom a set of measured surgically induced refractive corrections for the eye of the current patient as a result of the implantation of the IOL.

4. The system of claim 3, wherein the processor is further configured to, after implantation of the IOL having the selected one or more parameters into the eye of the current patient:
  include the set of adjusted intended refractive corrections to be applied to the eye of the current patient in the sets of intended refractive corrections to be applied to eyes of previous patients; and
  include the set of measured surgically induced refractive corrections for the eye of the current patient as a result of the implantation of the IOL in the sets of surgically induced refractive corrections for eyes of previous patients as a result of previous surgeries.

5. The system of claim 1, wherein the selected one or more parameters of the IOL to be implanted into the eye of the current patient further include a dioptic power, a refractive index, an asphericity, a toricity, a haptic angulation and a lens filter.

6. The system of claim 1, wherein the OCT is configured to act as a ranging device to align the current patient in relation to the system while measuring the set of pre-surgery values for the plurality of optical properties of the eye of the current patient.

* * * * *